United States Patent
Pagliuca et al.

(10) Patent No.: US 11,466,256 B2
(45) Date of Patent: Oct. 11, 2022

(54) STEM CELL DERIVED ISLET DIFFERENTIATION

(71) Applicant: Vertex Pharmaceuticals Incorporated, Boston, MA (US)

(72) Inventors: Felicia J. Pagliuca, Boston, MA (US); George Harb, Boston, MA (US); Lillian Ye, Billerica, MA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 17/472,220

(22) Filed: Sep. 10, 2021

(65) Prior Publication Data

US 2021/0403875 A1 Dec. 30, 2021

Related U.S. Application Data

(63) Continuation of application No. 17/171,497, filed on Feb. 9, 2021, which is a continuation of application No. PCT/US2019/045985, filed on Aug. 9, 2019.

(60) Provisional application No. 62/717,665, filed on Aug. 10, 2018.

(51) Int. Cl.
*C12N 5/071* (2010.01)

(52) U.S. Cl.
CPC ........ *C12N 5/0678* (2013.01); *C12N 2500/46* (2013.01); *C12N 2501/11* (2013.01); *C12N 2501/117* (2013.01); *C12N 2501/119* (2013.01); *C12N 2501/15* (2013.01); *C12N 2501/155* (2013.01); *C12N 2501/16* (2013.01); *C12N 2501/19* (2013.01); *C12N 2501/415* (2013.01); *C12N 2501/999* (2013.01)

(58) Field of Classification Search
CPC .................................................. C12N 5/0678
See application file for complete search history.

(56) References Cited

U.S. PATENT DOCUMENTS

| | | | |
|---|---|---|---|
| 4,378,016 | A | 3/1983 | Loeb |
| 4,391,909 | A | 7/1983 | Lim |
| 5,674,289 | A | 10/1997 | Fournier et al. |
| 5,843,780 | A | 12/1998 | Thomson |

(Continued)

FOREIGN PATENT DOCUMENTS

| | | | |
|---|---|---|---|
| EP | 1456356 A2 | 9/2004 | |
| EP | 1676574 A2 | 7/2006 | |

(Continued)

OTHER PUBLICATIONS

Eberhardt et al., Multipotent nestin and ISL-1 positive mesenchymal stem cells isolated from human pancreatic islets. Biochemical and Biophysical Research Communications, vol. 345, No. 3 (Jul. 7, 2006) pp. 1167-1176. (Year: 2006).*

(Continued)

*Primary Examiner* — Kara D Johnson
(74) *Attorney, Agent, or Firm* — Wilson Sonsini Goodrich & Rosati

(57) ABSTRACT

Provided herein are methods of producing β cells and precursors thereof utilizing a Wnt signaling inhibitor or PKC activator, or both. Also provided herein are in vitro cultures comprising said cells, methods of treating a subject with a disease characterized by high blood sugar levels over a prolonged period of time by administering said cells, and devices for encapsulating said cells.

30 Claims, 44 Drawing Sheets

(56) References Cited

U.S. PATENT DOCUMENTS

| | | |
|---|---|---|
| 6,090,622 A | 7/2000 | Gearhart et al. |
| 6,200,806 B1 | 3/2001 | Thomson |
| 6,436,704 B1 | 8/2002 | Roberts et al. |
| 6,667,176 B1 | 12/2003 | Funk et al. |
| 6,800,480 B1 | 10/2004 | Bodnar et al. |
| 7,029,913 B2 | 4/2006 | Thomson |
| 7,033,831 B2 | 4/2006 | Fisk et al. |
| 7,153,684 B1 | 12/2006 | Hogan |
| 7,157,278 B2 | 1/2007 | Jin |
| 7,163,918 B2 | 1/2007 | Piccariello et al. |
| 7,297,539 B2 | 11/2007 | Mandalam et al. |
| 7,326,572 B2 | 2/2008 | Fisk et al. |
| 7,410,798 B2 | 8/2008 | Mandalam et al. |
| 7,432,104 B2 | 10/2008 | Mitalipova et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 7,625,753 B2 | 12/2009 | Kelly et al. |
| 7,695,963 B2 | 4/2010 | Agulnick et al. |
| 7,695,965 B2 | 4/2010 | Martinson et al. |
| 7,704,738 B2 | 4/2010 | D'Amour et al. |
| 7,964,402 B2 | 6/2011 | Terskikh et al. |
| 7,985,585 B2 | 7/2011 | D'Amour et al. |
| 7,993,916 B2 | 8/2011 | Agulnick et al. |
| 7,993,920 B2 | 8/2011 | Martinson et al. |
| 8,008,075 B2 | 8/2011 | Green et al. |
| 8,129,182 B2 | 3/2012 | D'Amour et al. |
| 8,153,429 B2 | 4/2012 | Robins et al. |
| 8,187,878 B2 | 5/2012 | Dalton et al. |
| 8,211,699 B2 | 7/2012 | Robins et al. |
| 8,216,836 B2 | 7/2012 | D'Amour et al. |
| 8,278,106 B2 | 10/2012 | Martinson et al. |
| 8,334,138 B2 | 12/2012 | Robins et al. |
| 8,338,170 B2 | 12/2012 | Kelly et al. |
| 8,415,153 B2 | 4/2013 | Majumdar et al. |
| 8,445,273 B2 | 5/2013 | Green et al. |
| 8,603,811 B2 | 12/2013 | D'Amour et al. |
| 8,623,645 B2 | 1/2014 | D'Amour et al. |
| 8,647,873 B2 | 2/2014 | D'Amour et al. |
| 8,658,151 B2 | 2/2014 | Kelly et al. |
| 8,785,184 B2 | 7/2014 | Xu |
| 8,785,185 B2 | 7/2014 | Xu et al. |
| 8,859,286 B2 | 10/2014 | Agulnick |
| 9,096,832 B2 | 8/2015 | Xu |
| 9,109,245 B2 | 8/2015 | Agulnick et al. |
| 9,186,381 B2 | 11/2015 | Zender et al. |
| 9,650,610 B2 | 5/2017 | Agulnick |
| 9,974,784 B2 | 5/2018 | Groppe |
| 9,982,235 B2 | 5/2018 | Agulnick et al. |
| 10,030,229 B2 | 7/2018 | Peterson et al. |
| 10,138,465 B2 | 11/2018 | Rezania |
| 10,190,096 B2 | 1/2019 | Melton et al. |
| 10,253,298 B2 | 4/2019 | Melton et al. |
| 10,443,042 B2 | 10/2019 | Melton et al. |
| 10,457,916 B2 | 10/2019 | Kume et al. |
| 10,655,106 B2 | 5/2020 | Peterson et al. |
| 2001/0049130 A1 | 12/2001 | Spielberg |
| 2002/0094569 A1 | 7/2002 | Yu et al. |
| 2003/0138948 A1 | 7/2003 | Fisk et al. |
| 2004/0047837 A1 | 3/2004 | Fong et al. |
| 2004/0121460 A1 | 6/2004 | Lumelsky et al. |
| 2004/0191901 A1 | 9/2004 | Assady et al. |
| 2004/0259244 A1 | 12/2004 | Scharp et al. |
| 2005/0053588 A1 | 3/2005 | Yin |
| 2006/0040385 A1 | 2/2006 | Itskovitz-Eldor et al. |
| 2006/0040387 A1 | 2/2006 | Fisk et al. |
| 2006/0194321 A1 | 8/2006 | Colman et al. |
| 2007/0142376 A1 | 6/2007 | Fleenor et al. |
| 2008/0145889 A1 | 6/2008 | Fisk et al. |
| 2008/0299582 A1 | 12/2008 | Mandalam et al. |
| 2009/0047263 A1 | 2/2009 | Yamanaka et al. |
| 2009/0068742 A1 | 3/2009 | Yamanaka |
| 2009/0170198 A1 | 7/2009 | Rezania |
| 2009/0186076 A1 | 7/2009 | Kataoka et al. |
| 2009/0191159 A1 | 7/2009 | Sakurada et al. |
| 2009/0227032 A1 | 9/2009 | Yamanaka et al. |
| 2009/0246875 A1 | 10/2009 | Yamanaka et al. |
| 2009/0263896 A1 | 10/2009 | Kelly et al. |
| 2009/0298178 A1 | 12/2009 | D'Amour |
| 2009/0304646 A1 | 12/2009 | Sakurada et al. |
| 2009/0325180 A1 | 12/2009 | Fisk et al. |
| 2010/0015100 A1 | 1/2010 | Xu |
| 2010/0015711 A1 | 1/2010 | Davis et al. |
| 2010/0112693 A1 | 5/2010 | Rezania et al. |
| 2010/0144033 A1 | 6/2010 | Mandalam et al. |
| 2010/0240130 A1 | 9/2010 | Majumdar et al. |
| 2010/0255580 A1 | 10/2010 | Rezania |
| 2010/0260728 A1 | 10/2010 | Martinson et al. |
| 2010/0267731 A1 | 10/2010 | Nakamura |
| 2010/0311166 A1 | 12/2010 | Florio et al. |
| 2011/0008819 A1 | 1/2011 | Chipperfield et al. |
| 2011/0014702 A1 | 1/2011 | Xu |
| 2011/0053930 A1 | 3/2011 | Yu et al. |
| 2011/0151560 A1 | 6/2011 | Xu |
| 2011/0280842 A1 | 11/2011 | Melton et al. |
| 2011/0281355 A1 | 11/2011 | Xu |
| 2011/0305672 A1 | 12/2011 | Dalton et al. |
| 2012/0009675 A1 | 1/2012 | Martinson et al. |
| 2012/0021519 A1 | 1/2012 | Ichida et al. |
| 2012/0052571 A1 | 3/2012 | Fryer |
| 2012/0052575 A1 | 3/2012 | Rezania |
| 2012/0052576 A1 | 3/2012 | Rezania |
| 2012/0135015 A1 | 5/2012 | Noguchi et al. |
| 2012/0141436 A1 | 6/2012 | Bonner-Weir et al. |
| 2013/0034526 A1 | 2/2013 | Itskovitz-Eldor et al. |
| 2013/0071931 A1 | 3/2013 | Ishikawa |
| 2013/0189777 A1 | 7/2013 | Rezania |
| 2013/0316357 A1 | 11/2013 | Damour et al. |
| 2013/0330823 A1 | 12/2013 | Rezania |
| 2013/0337564 A1 | 12/2013 | Davis et al. |
| 2014/0029704 A1 | 1/2014 | Becker |
| 2014/0080210 A1 | 3/2014 | Davis et al. |
| 2014/0134726 A1 | 5/2014 | D'Amour et al. |
| 2014/0154801 A1 | 6/2014 | D'Amour et al. |
| 2014/0154802 A1 | 6/2014 | Robins et al. |
| 2014/0162359 A1 | 6/2014 | Rezania |
| 2014/0186305 A1 | 7/2014 | Rezina |
| 2014/0186948 A1 | 7/2014 | Schulz et al. |
| 2014/0186953 A1 | 7/2014 | Rezania |
| 2014/0193902 A1 | 7/2014 | D'Amour et al. |
| 2014/0193904 A1 | 7/2014 | D'Amour et al. |
| 2014/0242693 A1 | 8/2014 | Fryer et al. |
| 2014/0271566 A1 | 9/2014 | Agulnick |
| 2014/0287944 A1 | 9/2014 | Hrvatin et al. |
| 2014/0329704 A1 | 11/2014 | Melton et al. |
| 2014/0335611 A1 | 11/2014 | Chen et al. |
| 2015/0017135 A1 | 1/2015 | Agulnick |
| 2015/0104430 A1 | 4/2015 | Keller et al. |
| 2015/0218522 A1 | 8/2015 | Peterson et al. |
| 2015/0240212 A1 | 8/2015 | Peterson et al. |
| 2015/0247123 A1 | 9/2015 | Ekberg et al. |
| 2015/0329828 A1 | 11/2015 | Rezania |
| 2015/0376574 A1 | 12/2015 | Talavera-Adame et al. |
| 2016/0022742 A1 | 1/2016 | Zender et al. |
| 2016/0040130 A1 | 2/2016 | Rezania |
| 2016/0152950 A1 | 6/2016 | Zhang et al. |
| 2016/0175363 A1 | 6/2016 | Melton et al. |
| 2016/0177267 A1 | 6/2016 | Melton et al. |
| 2016/0177268 A1 | 6/2016 | Melton et al. |
| 2016/0177269 A1 | 6/2016 | Melton et al. |
| 2016/0186143 A1 | 6/2016 | Melton et al. |
| 2016/0208215 A1 | 7/2016 | Doehn et al. |
| 2016/0326495 A1 | 11/2016 | Ekberg et al. |
| 2016/0369239 A1 | 12/2016 | Agulnick et al. |
| 2017/0029778 A1 | 2/2017 | Peterson et al. |
| 2017/0233700 A1 | 8/2017 | Kunisada |
| 2017/0240866 A1 | 8/2017 | Wells et al. |
| 2017/0349884 A1 | 12/2017 | Karp et al. |
| 2017/0362572 A1 | 12/2017 | Rieck et al. |
| 2018/0087033 A1 | 3/2018 | Xu et al. |
| 2018/0153941 A1 | 6/2018 | Melton et al. |
| 2018/0179593 A1 | 6/2018 | Melton et al. |
| 2019/0017031 A1 | 1/2019 | Peterson et al. |
| 2019/0085295 A1 | 3/2019 | Christophersen et al. |

(56) References Cited

U.S. PATENT DOCUMENTS

| | | | |
|---|---|---|---|
| 2019/0119649 A1 | 4/2019 | Melton et al. | |
| 2019/0185817 A1 | 6/2019 | Melton et al. | |
| 2019/0338250 A1 | 11/2019 | Melton et al. | |
| 2020/0199539 A1 | 6/2020 | Melton et al. | |
| 2020/0332262 A1 | 10/2020 | Poh et al. | |
| 2020/0347355 A1 | 11/2020 | Melton et al. | |
| 2020/0347356 A1 | 11/2020 | Melton et al. | |
| 2020/0347357 A1 | 11/2020 | Melton et al. | |
| 2020/0347358 A1 | 11/2020 | Peterson et al. | |
| 2020/0385681 A1 | 12/2020 | Peterson et al. | |
| 2021/0017157 A1 | 1/2021 | Thiel et al. | |
| 2021/0198632 A1 | 7/2021 | Pagliuca et al. | |
| 2021/0198633 A1* | 7/2021 | Nostro | C12N 5/0678 |
| 2021/0238553 A1 | 8/2021 | Pagliuca et al. | |
| 2021/0403876 A1 | 12/2021 | Pagliuca et al. | |

FOREIGN PATENT DOCUMENTS

| | | |
|---|---|---|
| EP | 2267116 A1 | 12/2010 |
| EP | 2292734 A1 | 3/2011 |
| EP | 2341147 A2 | 7/2011 |
| EP | 2377922 A2 | 10/2011 |
| EP | 2283117 B1 | 10/2013 |
| EP | 2650359 A1 | 10/2013 |
| EP | 2650360 A2 | 10/2013 |
| EP | 2664669 A1 | 11/2013 |
| EP | 2674485 A1 | 12/2013 |
| JP | 2006506047 A | 2/2006 |
| JP | 2016503654 A | 2/2016 |
| JP | 2016506246 A | 3/2016 |
| RU | 2011121843 A | 12/2012 |
| WO | WO-9631242 A1 | 10/1996 |
| WO | WO-9920740 A2 | 4/1999 |
| WO | WO-9920741 A1 | 4/1999 |
| WO | WO-0151616 A2 | 7/2001 |
| WO | WO-0188104 A2 | 11/2001 |
| WO | WO-0242445 A2 | 5/2002 |
| WO | WO-03020920 A1 | 3/2003 |
| WO | WO-03050249 A2 | 6/2003 |
| WO | WO-03100026 A2 | 12/2003 |
| WO | WO-2004058764 A1 | 7/2004 |
| WO | WO-2007002136 A2 | 1/2007 |
| WO | WO-2007075807 A2 | 7/2007 |
| WO | WO-2007103282 A2 | 9/2007 |
| WO | WO-2007127927 A2 | 11/2007 |
| WO | WO-2008083331 A2 | 7/2008 |
| WO | WO-2008102000 A1 | 8/2008 |
| WO | WO-2009012428 A2 | 1/2009 |
| WO | WO-2009018453 A1 | 2/2009 |
| WO | WO-2009070592 A2 | 6/2009 |
| WO | WO-2010057039 A2 | 5/2010 |
| WO | WO-2010059778 A1 | 5/2010 |
| WO | WO-2011059725 A2 | 5/2011 |
| WO | WO-2011079017 A2 | 6/2011 |
| WO | WO-2011109279 A2 | 9/2011 |
| WO | WO-2011123572 A1 | 10/2011 |
| WO | WO-2011139628 A1 | 11/2011 |
| WO | WO-2011143299 A2 | 11/2011 |
| WO | WO-2012020845 A1 | 2/2012 |
| WO | WO-2012021698 A2 | 2/2012 |
| WO | WO-2012025725 A1 | 3/2012 |
| WO | WO-2012030540 A2 | 3/2012 |
| WO | WO-2012168930 A2 | 12/2012 |
| WO | WO-2013057164 A1 | 4/2013 |
| WO | WO-2013095953 A1 | 6/2013 |
| WO | WO-2014033322 A1 | 3/2014 |
| WO | WO-2014062138 A1 | 4/2014 |
| WO | WO-2014105543 A1 | 7/2014 |
| WO | WO-2014105546 A1 | 7/2014 |
| WO | WO-2014106141 A1 | 7/2014 |
| WO | WO-2014151871 A2 | 9/2014 |
| WO | WO-2014160413 A1 | 10/2014 |
| WO | WO-2014201167 A1 | 12/2014 |
| WO | WO-2015002724 A2 | 1/2015 |
| WO | WO-2015013653 A1 | 1/2015 |
| WO | WO-2015028614 A1 | 3/2015 |
| WO | WO-2015173576 A1 | 11/2015 |
| WO | WO-2015175307 A1 | 11/2015 |
| WO | WO-2016100035 A1 | 6/2016 |
| WO | WO-2016100898 A1 | 6/2016 |
| WO | WO-2016100909 A1 | 6/2016 |
| WO | WO-2016100921 A1 | 6/2016 |
| WO | WO-2016100925 A1 | 6/2016 |
| WO | WO-2016100930 A1 | 6/2016 |
| WO | WO-2016101010 A1 | 6/2016 |
| WO | WO-2016172564 A1 | 10/2016 |
| WO | WO-2017019702 A1 | 2/2017 |
| WO | WO-2017091943 A1 | 6/2017 |
| WO | WO-2017144695 A1 | 8/2017 |
| WO | WO-2017177163 A1 | 10/2017 |
| WO | WO-2017222879 A1 | 12/2017 |
| WO | WO-2018159805 A1 | 9/2018 |
| WO | WO-2019018818 A1 | 1/2019 |
| WO | WO-2019099725 A1 | 5/2019 |
| WO | WO-2019169351 A1 | 9/2019 |
| WO | WO-2020033879 A1 | 2/2020 |
| WO | WO-2020264072 A1 | 12/2020 |

OTHER PUBLICATIONS

Korytnikov, Roman., Role of tankyrase inhibitors in the generation of NKX6-1+ endoderm. Dissertation, University of Toronto (2016). (Year: 2016).*

Brolen et al., Signals from the embryonic mouse pancreas induce differentiation of human embryonic stem cells into insulin-producing β-cell-like cells. Diabetes, vol. 54, No. 10 (Oct. 2005) pp. 2867-2874. (Year: 2005).*

Aguayo-Mazzucato, et al., "Mafa Expression Enhances Glucose-Responsive Insulin Secretion in Neonatal Rat Beta Cells," Diabetologia, 54(3):583-593, (Mar. 2011).

Aguayo-Mazzucato, et al., "Thyroid Hormone Promotes Postnatal Rat Pancreatic β-Cell Development and Glucose-Responsive Insulin Secretion Through MAFA," Diabetes, 62:1569-1580, (2013).

"Agulnick, et al., "Insulin-Producing Endocrine Cells Differentiated In Vitro From Human Embryonic Stem Cells Function in Macroencapsulation Devices In Vivo" (2015) Cells Translation Medicine 4:1214-1222".

Amariglio, et al., "Donor-Derived Brain Tumor Following Neural Stem Cell Transplantation in an Ataxia Telangiectasia Patient," PLOS Medicine, 6(2):1-3, (2009). (2 pages of translation of relevance).

Apelqvist, et al., Notch Signaling Controls Pancreatic Cell Differentiation, Nature 400, (1999): 877-881.

Ashery-Padan, et al. Conditional inactivation of Pax6 in the pancreas causes early onset of diabetes. Developmental Biology, 269 (2004): 479-488.

Assady, et al. Insulin Production by Human Embryonic Stem Cells. Diabetes, 50 (2001): 1691-1697.

Axxora.com Product Search Results for "Alk5 Inhibitor." Retrieved from URL: https://www.axxora.com/product-listing/ on Oct. 21, 2020 [1-2](Year: 2020).

Baetge, E. E., Production of β-cells from human embryonic stem cells, Diabetes, Obesity and Metabolism 10 (2008): 186-194.

Basford, et al., The Functional and molecular Characterisation of Human Embryonic Stem Cell-Derived Insulin-Positive Cells Compared with Adult Pancreatic Beta Cells, Diabetologia, 55 (2012): 358-371.

Beattie, et al., Sustained proliferation of PDX-1+ cells derived from human islets, Diabetes, 1999, 48:1013-9.

Bellin, et al. Potent induction immunotherapy promotes long-term insulin independence after islet transplantation in type 1 diabetes. Am J Transplant. Jun. 2012;12(6):1576-83. doi: 10.1111/j.1600-6143.2011.03977.x. Epub Apr. 11, 2012.

Bennett, et al. SP600125, An Anthrapyrazolone Inhibitor of Jun N-Terminal Kinase. PNAS, vol. 98, No. 24, 20, 2001, pp. 13681-13686.

Blazhevich, et al., "Cell Culturing: Lecture Course," 6 pages (1 page of translation of relevance) (2004).

(56) References Cited

OTHER PUBLICATIONS

Boretti, et al., Induced cell clustering enhances islet beta cell formation from human cultures enriched for pancreatic ductal epithelial cells, 2003 Summer Bioengineering Conference, Jun. 25-29, Sonesta Beach Res ort in Ke Bisca ne, Florida.
Boretti, et al. Induced cell clustering enhances islet beta cells formation from human cultures enriched for pancreatic ductal epithelial cells, Tissue Engg. 12.4 (2006): 939-948.
Bose, et al., Human embryonic stem cell differentiation into insulin secreting beta-cells for diabetes, Cell Bioi Int., 3611 (2012): 1013-1020.
Brolen, et al. Signals From the Embryonic Mouse Pancreas Induce Differentiation of Human Embryonic Stem Cells Into Insulin-Producing r3-cell-like Cells. Diabetes 54 (2005): 2867-2874.
Cai, et al., Generation of Homogeneous PDX1þ Pancreatic Progenitors from Human ES Cell-derived Endoderm Cells, Journal of Molecular Cell Biology (2010), 2:50-60.
Campbell-Thompson, et al., "Collection Protocol for Human Pancreas," Journal of Visualized Experiments, 63:1-5, (May 2012).
Cerf, Transcription factors regulating β-cell function, European Journal of Endocrinology, 155 (2006): 671-679.
Chakrabarti, et al., Transcription factors direct the development and function of pancreatic beta cells, Trends Endocrinol Metab., 14.2 (Mar. 2003): 78-84.
Chen, et al., Scalable GMP complain suspension culture system for human ES cells, Stem Cell Research 8 (2012): 388-402.
Cheng, et al. Self-renewing endodermal progenitor lines generated from human pluripotent stem cells. Cell Stem Cell 10 (2012): 371-384.
"Chiang, et al., Single-Cell Transcript Analysis of Pancreas Development, Developmental Cell, Mar. 2003, 4:383-393".
Choi, et al. A comparison of genetically matched cell lines reveals the equivalence of human iPSCs and ESCs. Nat Biotechnol. Nov. 2015;33(11):1173-81. doi: 10.1038/nbt.3388. Epub Oct. 26, 2015.
"CMRL-1066 Data Sheet. Retrieved online Sep. 30, 17. https://www.sigmaaldrich.com/content/dam/sigma aldich/docs/sigma/datasheet/c0422dat.pdf (1998)."
Cohen, et al., Antibiotics Reduce the Growth Rate and Differentiation of Embryonic Stem Cell Cultures, Tissue Eng., 12.7 (2006): 2025-2030.
Corkey, et al., A Role for Malonyl-CoA in Glucose-Stimulated Insulin Secretion from Clonal Pacreatic β-Cells, J. Bioi. Chem., 254.36 (Dec. 1989): 21608-21612.
D'Amour, et al., Efficient differentiation of human embryonic stem cells to definitive endoderm, Nat. Biotech., 23(12): 1534-41 (2005).
D'Amour, et al. Production of pancreatic hormone-expressing endocrine cells from human embryonic stem cells. Nat Biotechnol. Nov. 2006;24(11):1392-401.
"Docherty, "Pancreatic Stellate Cells Can Form New 13-Like Cells," Biochem, J., 421:e1-e4, (2009)."
Dror,et, al., Notch Signaling Suppresses Apoptosis in Adult Human and Mouse Pancreatic Islet Cells, Diabetlogia 50 (2007): 2504-2515.
Eberhardt, et al. Multipotential nestin and Isl-1 positive mesenchymal stem cells isolated from human pancreatic islets. Biochem Biophys Res Commun. Jul. 7, 2006; 345.3, 1167-76. Epub May 11, 2006.
Extended European search Report for corresponding EP Application No. 18836082.0 dated Feb. 24, 2021.
Falzacappa et al., "3,5,3'-Triiodothyronine (T3) is a Survival Factor for Pancreatic Beta-Cells Undergoing Apoptosis," J. Cell Physiol., 206(2):309-321, (Feb. 2006).
Gotoh et al., Gamma-Irradiation as a Tool to Reduce Immunogenicity of Islet Allo-and-Xeonograpfs, Horm Metab Res Suppl., Jan. 1, 1990, vol. 25, pp. 89-96. Abstract only.
Greggio, et al., Artificial Three-Dimensional Niches Deconstruct Pancreas Development in vitro, Development, 140 (2013): 4452-4462.
Habener, et al., Minireview: transcriptional regulation in pancreatic development Endocrinol., 146:1025-34 (2005).

Hanley, "Closing in on Pancreatic Beta Cells," Nature Biotechnology, 32(11):1100-1102, (Nov. 2014).
Hao, et al., In Vivo Structure Activity Relationship Study of Dorsomorphin Analogs Identifies Selective VEGF and BMP Inhibitors, ACS Chem Biol., Feb. 19, 2010, vol. 5, No. 2, pp. 245-253.
Haycock, John W., 3D Cell Culture: A Review of Current Approaches and Techniques, Molecular Biolo 695 (2011): 1-15.
"Heremans, et al., Recapitulation of embryonic neuroendocrine differentiation in adult human pancreatic duct cells expressing neurogenin 3, The Journal of Cell Biology, Oct. 28, 2002, 159(2):303-311".
Hernandez, et al., Microcapsules and microcarriers for in situ cell delivery, Advanced Drug Deliver Reviews 62 (2010): 711-730.
Hess et al., Bone Marrow-Derived Stem Cells Initiate Pancreatic Regeneration, Nature Biotechnology, Jun. 22, 2003, vol. 21, Issue 7, pp. 763-770.
"Hilderink, et al., "Controlled aggregation of primary human pancreatic islet cells leads to glucose-responsive pseudoislets comparable to native islets" (2015) J. Cell. Mol. Med., vol. 19, No. 8, pp. 1836-1846".
Hrvatin, et al. Differentiated human stem cells resemble fetal, not adult, β-cells. PNAS, 111.8, 3038-3043.
Hrvatin: Exploring the Use of Human Pluripotent Stem Cells to Create Functional Pancreatic β Cells. Harvard University Library, Doctoral Dissertation. [1-165] (2012) https://dash.harvard.edu/bitstream/handle/1/10433470/Hrvatin_gsas.harvard_0084L_10728.pdf ?sequence=3&isAllowed=y.
Hur et al.: New method to differentiate human peripheral blood monocytes into insulinproducing cells: Human hematosphere culture. Biochem Biophys Res Commun. 418(4): 765-769 (2012).
Huynh, et al., "Screening and Identification of a Novel Class of TGF-13 Type 1 Receptor Kinase Inhibitor," Society for Laboratory Automation and Screening, 16(7):724-733, (2011).
International Search Report and Written Opinion for PCT/US2018/043179 dated Oct. 16, 2018.
Isayeva, et al. Characterization and performance of membranes designed for macroencapsulation/implantation of pancreatic islet cells. Biomaterials. Sep. 2003;24(20):3483-91.
Jahansouz, et al., Evolution of β-Cell Replacement Therapy in Diabetes Mellitus: Islet Cell Transplantation, Journal of Transplantation, (2011): 1-21.
Jeon et al.: Differentiation and Transplantation of Functional Pancreatic Beta Cells Generated from Induced Pluripotent Stem Cells Derived from a Type 1 Diabetes Mouse Model. Stem Cells Dev., 21(14): 2642-2655, (2012).
Jiang, et al. In vitro derivation of functional insulin-producing cells from human embryonic stem cells. Cell Res. Apr. 2007;17(4):333-44.
"Kelly, et al., "Cell-surface markers for the isolation of pancreatic cell types derived from human embryonic stem cells" (2011) Nature Biotechnology, p. 1-19".
"Kojima, Nobuhiko "In vitro reconstitution of pancreatic islets" (2014) Organogenesis 10:2, pp. 225-230".
Koshimizu et al.: Functional requirement of gp130-mediated signaling for growth and survival of mouse primordial germ cells in vitro and derivation of embryonic germ (EG) cells. Development 122(4):1235-1242 (1996).
Kozhukharova et al.: Novel Human Embryonic Stem Cell Lines C612 and C910. Cytology, 51(7): 551-558 (2009).
"Kroon, et al., Pancreatic endoderm derived from human embryonic stem cells generates glucose-responsive insulin-secreting cells in vivo, Nat. Biotech, Apr. 2008, 26(4):443-452".
Kumar, et al., Recent Developments in β-Cell Differentation of Pluripotent Stem Cells Induced by Small and Large Molecules, Int. J. Mol. Sci., 15.12 (2014): 23418-23447.
Kumar, et al. Signals from lateral plate mesoderm instruct endoderm toward a pancreatic fate. Dev Bioi. 259.1 (2003): 109-22.
Kunisada, et al., Small molecules induce efficient differentiation into insulinproducing cells from human induces pluripotent stem cells, Stem Cell Research, 2012, 8:274-284.
Lee et al.: All-Trans-Retinoic Acid as a Novel Therapeutic Strategy for Alzheimer's Disease. Expert Rev. Neurother, 9(11): 1615-1621 (2009).

(56) References Cited

OTHER PUBLICATIONS

Lee et al., Differentiation into Endoderm Lineage: Pancreatic differentiation from Embryonic Stem Cells, International Journal of Stem Cells, Apr. 4, 2011, vol. 4, No. 1, pp. 35-42.
Lim et al., Microencapsulated islets as bioartificial endocrine pancreas, Science 210(4472):908-10 (1980).
Lima et al., Generation of Functional Beta-Like Cells from Human Exocrine Pancreas, PLoS One, May 31, 2016, vol. 11, No. 5, pp. 1-19.
Lin et al.: Transforming growth factor-beta/Smad3 signaling regulates insulin gene transcription and pancreatic islet beta-cell function. J Biol Chem. 284(18): 12246-12257 (2009).
Lumelsky, et al., Differentiation of Embryonic Stem Cells to Insulin-Secreting Structures Similar to Pancreatic Islets, Science, 292:1389-94 (May 2001).
Madsen, et al. Towards cell therapy for diabetes. Nat Biotechnol. 24.12 (2006): 1481-3.
Maehr, et al., Generation of pluripotent stem cells from patients with type 1 diabetes, Proc Natl Acad Sci. 106.37 (2009): 15768-15773.
Manning et al. The Protein Kinase Complement of the Human Genome. Science. 298:1912-1934. 2002.
Marzorati, et al., Culture Medium Modulates Proinflammatory Conditions of Human Pancreatic Islets Before Transplantation, Am. J. Transplant, 6.11 (2006): 2791-2795.
Matschinsky, Assessing the potential of glucokinase activators in diabetes therapy, Nature Reviews Drug Discovery, 8 (2009): 399-416.
Matsui, Y., et al., (1992), Derivation of pluripotential embryonic stem cells from murine primordial germ cells in culture, Cell 70:841.
McLean, et al., Activin a Efficiently Specifies Definitive Endoderm from Human Embryonic Stem Cells Only When Phosphatidylinositol 3-Kinase Signaling Is Suppressed. Stem Cells, 2007, 25: 29-38.
McQuilling et al.: New Alginate Microcapsule System for Angiogenic Protein Delivery and Immunoisolation of Islets for Transplantation in the Rat Omentum Pouch. Transplantation Proceedings, 43(9): 3262-3264 (Nov. 2011).
"Smelt, et al., "Pancreatic Beta-Cell Purification by Altering FAD and NAD(P)H Metabolism" (2018) Experimental Diabetes Research vol. 2008, Article ID 165360, pp. 1-11".
Michael, et al., Pancreatic β-Cells Secrete Insulin in Fast- and Slow-Release Forms, Diabetes, 55 (2006): 600-607.
Moens, et al., Dual glucagon recognition by pancreatic beta-cells via glucagon and glucagon-like peptide 1 receptors, Diabetes, 47 (1998): 66-72.
Mollard, et al. Design, Synthesis and Biological Evaluation of a Series of Novel Axl Kinase Inhibitors. ACS Med Chem Lett. Dec. 8, 2011;2(12):907-912.
Morrison et al.: Regulatory Mechanisms in Stem Cell Biology. Cell 88(3):287-298 (1997).
Motte, et al. Composition and function of macroencapsulated human embryonic stem cell-derived implants: comparison with clinical human islet cell grafts. Am J Physiol Endocrinol Metab. Nov. 1, 2014;307(9):E838-46. doi: 10.1152/ajpendo.00219.2014. Epub Sep. 9, 2014.
Mudduluru, et al. Regulation of Axl receptor tyrosine kinase expression by miR-34a and miR-199a/b in solid cancer. Oncogene. Jun. 23, 2011;30(25):2888-99. doi: 10.1038/onc.2011.13. Epub Feb. 14, 2011.
Murua, et al., Cell microencapsulation technology: Towards clinical application, Journal of Controlled Release, 132.2 (2008): 76-83.
Narayanan, et al. Extracellular Matrix-Mediated Differentiation of Human Embryonic Stem Cells: Differentiation to Insulin-Secreting Beta Cells. Tissue Engineering, Part A, 20.1 & 2, 424-433.
Natalicchio et al.: Exendin-4 Protects Pancreatic Beta Cells from Palmitate-Induced Apoptosis by Interfering with GPR40 and the MKK4/7 Stress Kinase Signaling Pathway. Diabetologia, 56: 2456-2466 (2013).
Neely et al., DMH1, a Highly Selective Small Molecule BGMP Inhibitor Promotes Neurogenesis of hiPSCs: Comparison of PAX6 and SOX1 Expression During Neural Induction, ACS Chem Neurosci, Mar. 5, 2012, vol. 3, No. 6, pp. 482-491.
Nishimura, et al., "A Switch from MafB to MafA Expression Accompanies Differentiation to Pancreatic 13-Cells," Developmental Biology, 293:526-539, (2006).
Nostro, et al., Generation of beta cells from human pluripotent stem cells: Potential for regenerative medicine, Seminars in Cell & Developmental Biology, 23 (2012): 701-710.
Nostro, et al. Stage-specific signaling through TGFβ-family members and WNT regulates patterning and pancreatic specification of human pluripotent stem cells. Development 138 (2011): 861-871.
O'Brien, et al., Suspended in culture—Human pluripotent cells for scalable technologies, Stem cell Research 9 (2012): 167-170.
Okazaki et al.: Staurosporine, a novel protein kinase inhibitor, enhances HL-60-cell differentiation induced by various compounds. Exp. Hemtaol. 16(1):42-48 (1988).
Orive, et al., Application of cell encapsulation for controlled delivery of biological therapeutics, Advanced Dru Delive Reviews 1-12 2013.
Pagliuca, et al. Generation of functional human pancreatic β cells in vitro. Cell. Oct. 9, 2014;159(2):428-39. doi: 10.1016/j.cell.2014.09.040.
Pagliuca et al.: How to make a functional β-cell. Development 140, 2472-2483 (2013).
Parsons, et al., Notch-Responsive Cells Initiate the Secondary Transition in Larval Zebrafish Pancreas, Mechanism of Development, 126.10 (2009): 898-912.
PCT/US2019/045985 International Search Report and Written Opinion dated Dec. 17, 2019.
Phillips, et al., Directed Differentiation of Human Embryonic Stem Cells into the Pancreatic Endocrine Lineage, Stem Cells and Dev., 16 (2007): 561-578.
"Spijker, et al., "Conversion of Masture Human B-Cells Into Glucagon-Producing a-Cells" (2013) Diabetes, vol. 62, p. 2471-2480".
Piran, et al., "Pharmacological Induction of Pancreatic Islet Cell Transdifferentiation; Relevance Type I Diabetes," Cell Death and Disease, 5(e1357):1-13, (2014).
Qi et al.: PVA Hydrogel Sheet Macroencapsulation of the Bioartificial Pancreas. Biomaterials, 24(27): 5885-5892 (2004).
"Ramachandran, et al., "Assessment of re-aggregated human pancreatic islets for secondary drug screening" British Journal of Pharmacology (2014) 171 3010-3022".
Ratanasavanh, et al. Immunocytochemical evidence for the maintenance of cytochrome PC33 450 isozymes, NADPH cytochrome C reductase, and epoxide hydrolase in pure and mixed primary cultures of adult human hepatocytes. J Histochem Cytochem. 34.4 (1986): 527-33.
Rathaore, et al., Microencapsulation of Microbial cells, Journal of Food Engineering, 116 (2013): 369-381.
Ravassard, et al. A genetically engineered human practical β cell line exibiting glucose-inducible insulin secretion. The Journal of clinical investigation 121.9 (2011): 3589-3597.
Rezania, et al., Enrichment of Human Embryonic Stem Cell-Derived NKX6.1—Expressing Pancreatic Progenitor Cells Accelerates the Maturation of InsulinSecretin Cells in Vivo, Stem Cells, 31 (2013): 2432-2442.
Rezania, et al. Maturation of human embryonic stem cell-deprived pancreatic progenitors into functional islets capable of treating pre-existing diabetes in mice. Diabetes 61 (2012): 2016-2029.
Rezania, et al. Production of functional glucagon-secreting α-cells from human embryonic stem cells. Diabetes, 60 (Jan. 2011): 239-247.
Rezania, et al. Reversal of diabetes with insulin-producing cells derived in vitro from human pluripotent stem cells. Nat Biotechnol. Nov. 2014;32(11):1121-33. doi: 10.1038/nbt.3033. Epub Sep. 11, 2014.
Roche. Protocols to differentiate embryonic stem cells into insulin producing cells. Av. Diabetol. 24.2 (2008): 128-137.
Ropiquet et al.: FGF7/KGF triggers cell transformation and invasion on immortalised human prostatic epithelial PNT1A cells. Int. J. Cancer 82(2):237-243 (1999).

(56) References Cited

OTHER PUBLICATIONS

Roskoski: A historical overview of protein kinases and their targeted small molecule inhibitors. Pharmalogical Res. 100:1-23 (2015).
Rovira, et al., Chemical Screen Identifies FDA-Approved Drugs and Target Pathways That Induce Precocious Pancreatic Endocrine Differentiation, Proc Natl Acad Sci USA. 108.48 (2011): 19264-19269.
Sander, et al. Homeobox gene Nkx6.1 lies downstream of Nkx2.2 in the major pathway of β-cell formation in the pancreas. Development 127 (2000): 5533-5540.
Sander, et al. The β-cell transcription factors and development of the pancreas. J Mol Med, 75 (1997): 327-340.
Schuldiner, et al., Effects of eight growth factors on the differentiation of cells derive from human embryonic stem cells, Proc. Nat. Acad. Sci., 97:11307-12 (2000).
Schulz, et al., A scalabe system for production of functional pancreatic progenitors from human embryonic stem cells, PLoS One, 7.5 (May 2012): 1-17.
Schumacher et al.: Staurosporine is a Potent Activator of Neuronal, Glial, and "CNS Stem Cell-Like" Neurosphere Differentiation in Murine Embryonic Stem Cells. Molecular and Cellular Neuroscience 23(4): 669-680 (2003).
Segerstople et al.: Single-cell transcriptome profiling of human pancreatic islets in health and type 2 diabetes. Cell Metab. 24(4):593-607 (2016).
Segrev, et al., Differentiation of Human Embryonic Stem Cells into Insulin-Producing Clusters, Stem Cells, 2004, 22:265-274.
Shaer, et al. Differentiation of human-induced pluripotent stem cells into insulin-producing clusters. Exp Clin Transplant. Feb. 2015;13(1):68-75. doi: 10.6002/ect.2013.0131. Epub Jan. 13, 2014.
Shahjalal, et al., Generation of insulin-producing B-like cells from human iPS cells in a defined and completely xeno-free culture system. Journal of Molecular cell biology, Jun. 2014; 6(5):394-408.
Shamblott, et al. Derivation of pluripotent stem cells from cultured human primordial germ cells, Proc. Natl. Acad. Sci. USA, vol. 95, pp. 13726-13731 (1998).
Shamblott, et al. Human embryonic germ cell derivatives express a broad range of developmentally distinct markers and proliferate extensively in vitro, Proc. Natl. Acad. Sci., vol. 98 No. 1, pp. 113-118 (2001).
Shapiro et al.: International trial of the Edmonton protocol for islet transplantation. N Engl J Med. 355(13): 1318-1330 (2006).
Shi, et al. Inducing Embryonic Stem Cells to Differentiate into Pancreatic β-cells by a Novel Three-Step Approach with Activin A and All-Trans Retinoic Acid. Stem Cells 23 (2005): 656-662.
Shim, et al., Directed differentiation of human embryonic stem cells towards a pancreatic cell fate, Diabetologia, 50 (2007): 1128-1138.
Sneddon, et al. Self-renewal of embryonic-stem-cell-derived progenitors by organ-matched mesenchyme. Nature. Nov. 29, 2012;491(7426):765-8. doi: 10.1038/nature11463. Epub Oct. 7, 2012.
Sorelle, et al., Beta Cell Replacement Therapy, Type 1 Diabetes-Pathogenesis, Genetics and Immunothera 22 (2011): 503-526.
Soria, et al., In-Vitro Differentiation of Pancreatic Beta-Cells, Differentiation, 68(4-5):205-19 (Oct. 2001).
Spence, et al. Sox17 regulates organ lineage segregation of ventral foregut progenitor cells. Dev Cell. Jul. 2009;17(1):62-74. doi: 10.1016/j.devcel.2009.05.012.
Sui et al.: Stem Cell Therapy for Diabetes: A Call for Efficient Differentiation of Pancreatic Progenitors. J. Regen. Med. 2(1):1-4 (2013).
Takahashi, et al. Induction of pluripotent stem cells from adult human fibroblasts by defined factors. Cell. Nov. 30, 2007;131(5):861-72.
Taylor, et al. NKX6.1 Is Essential for Maintaining the Functional State of Pancreatic Beta Cells. Cell Rep 4 (2013): 1262-275.
Thatava, et al., Indolactam V/GLP-1-mediated Differentiation of Human iPS Cells into Glucose-Responsive Insulin-Secreting Progeny, 18.3 (2011): 283-293.
Thermo Fisher Scientific, B-27 Serum-Free Supplement (50X) liquid, ThermoFisher Scientific Website, Retrieved from the Internet: URL: thermofisher.com/order/catalog/product/17504044?SID-srch-srp-17504044#/17504044?SID=srch-srp-17504044, on Sep. 15, 2021.
Thomson et al. Embryonic stem cell lines derived from human blastocysts. Science. Nov. 6, 1998;282(5391):1145-7.
Thomson, et al. Isolation of a primate embryonic stem cell line. Proc Natl Acad Sci U S A. Aug. 15, 1995;92(17):7844-8.
Thomson et al., Pluripotent Cell Lines Derived from Common Marmoset (*Callithrix jacchus*) Blastocysts, (1996) Biol. Reprod. 55:254-259.
Thowfeequ, et al., Betacellulin inhibits amylase and glucagon production and promotes beta cell differentiation in mouse embryonic pancreas, Diabetologia, 50 (2007): 1688-1697.
Tian et al.: Protein kinase C and calcium regulation of adenylyl cyclase in isolated rat pancreatic islets. Diabetes 50(11):2505-2513 (2001).
Treff, et al., Differentiation of Embryonic Stem Cells Conditionally Expressing Neurogenin 3, Stem Cells, 24.11 (1999): 2529-37.
Trott et al. "Long-Term Culture of Self-renewing Pancreatic Progenitors Derived from Human Pluripotent Stem Cells," Stem Cell Reports, Jun. 6, 2017 (Jun. 6, 2017), vol. 8, No. 6, pp. 1675-1688. entire document.
Tsaniras, et al., "Generating Pancreatic Beta-Cells from Embryonic Stem Cells by Manipulating Signaling Pathways," Journal of Endocrinology, 206:13-26, (2010).
Tsuchida, et al., Activin signaling as an emerging target for therapeutic interventions, Cell Communication & Signaling, 7.15 (2009): 1-11.
Veres et al.: Charting cellular identity during human in vitro β-cell differentiation. Nature 569(7756):368-373 [1-36] (2019).
Wachs, et al., High Efficacy of Clonal Growth and Expansion of Adult Neural Stem Cells, Laboratoryinvestigation, 83.7 (Jul. 2003): 949-962.
Xie, et al. Dynamic chromatin remodeling mediated by polycomb proteins orchestrates pancreatic differentiation of human embryonic stem cells. Cell Stem Cell 12 (2013): 224-237.
Xu et al.: Revealing a core signaling regulatory mechanism for pluripotent stem cell survival and self-renewal by small molecules. PNAS 107(18):8129-8134 (2010).
Yu, et al. Induced pluripotent stem cell lines derived from human somatic cells. Science. Dec. 21, 2007;318(5858):1917-20. Epub Nov. 20, 2007.
Zanin, et al., The development of encapsulated cell technologies as therapies for neurological and sensor diseases, Journal of Controlled Release 160 (2012): 3-13.
Zhang et al.: Highly efficient differentiation of human ES cells and iPS cells into mature pancreatic insulin-producing cells. Cell Research 19(4):429-438 (2009).
Zhdanov, et al., "The Secrets of the Third Kingdom," Publishing House "Znanie" Moscow:pp. 124-125, (1975). (2 pages of translation).
Zhu, et al., Generation of Pancreatic Insulin-Producing Cells from Rhesus Monkey Induced Pluripotent Stem Cells, Diabetologia, 54 (2011): 2325-2336.
Zhu et al.: Preventive effect of Notch signaling inhibition by a gamma-secretase inhibitor on peritoneal dialysis fluid-induced peritoneal fibrosis in rats. Am J Pathol. 176(2): 650-659 (2010).
Zulewski, Stem Cells with potential to generate insulin-producing cells in man, Swiss Med. Wkly, 136 (2006): 647-654.
Zweigerdt, et al., Scalable expansion of human pluripotent stem cells in suspension culture, Nature Protocols, 6.5 (2011): 689-700.
EP18879005.9 Extended European Search Report dated Jul. 13, 2021.
PCT/US2019/020430 International Search Report and Written Opinion dated May 8, 2019.
DW Engers, et al., Synthesis and structure-activity relationships of a novel and selective bone morphogenetic protein receptor (BMP) inhibitor derived from the pyrazolo[1,5-a]pyrimidine scaffold of dorsomorphin: the discovery of ML347 as an ALK2 versus ALK3 selective MLPCN probe. Bioorg. Med. Chem. Lett. 2013, 23, 3248-3252.

(56) References Cited

OTHER PUBLICATIONS

Massumi et al.: An abbreviated protocol for in vitro generation of functional human embryonic stem cell-derived beta-like cells. PLoS One 11(10):e0164457 DOI:10.1371/journal.pone.0164457 [1-24] (2016).
PCT/US2018/061364 International Search Report and Written Opinion dated Apr. 29, 2019.
PCT/US2020/039487 International Search Report and Written Opinion dated Sep. 22, 2020.
Russ et al.: Controlled induction of human pancreatic progenitors produces functional beta-like cells in vitro. EMBO J. 34(13):1759-1772 (2015).
Vegas, et al., Long term glycemic control using polymer encapsulated, human stem-cell derived B-cells in immune competent mice, Nat Med. Jan. 25, 2016, vol. 22, No. 3, pp. 306-311.
Abraham et al.: Glucagon action in the brain. Diabetologia 59(7):1367-1371 doi:10.1007/s00125-016-3950-3 (2016).
Biressi et al.: The homeobox gene Arx is a novel positive regulator of embryonic myogenesis. Cell Death Differentiation 15(1):94-104 doi:10.1038/sj.cdd.4402230 (2008).
Cai et al.: Isl1 identifies a cardiac progenitor population that proliferates prior to differentiation and contributes a majority of cells to the heart. Dev. Cell 2003 5(6):877-889 doi:10.1016/s1534-5807(03)00363-0 (2003).
Eisenberg et al.: Establishment of the mesodermal cell line QCE-6. A model system for cardiac cell differentiation. Circ Res. 78(2):205-216 (1996).
Hamamoto et al.: Lack of evidence for recipient precursor cells replenishing β-cells in transplanted islets. Cell Transplant 19(12):1563-1572 doi:10.3727/096368910X515881 (2010).
Kieffer et al.: Beta-cell replacement strategies for diabetes. J Diabetes Investig. 9(3):457-463 doi:10.1111/jdi.12758 (2017).
Kim et al.: Functional Diversification of Motor Neuron-specific Isl1 Enhancers during Evolution. PLoS Genetics 11(10):e1005560, pp. 1-27 doi:10.1371/journal.pgen.1005560 (2015).
Lopez et al.: Staurosporine-derived inhibitors broaden the scope of analog-sensitive kinase technology. J Am Chem Soc. 135(48):18153-18159 doi:10.1021/ja408704u (2013).
Moore et al.: Noninvasive in vivo measurement of beta-cell mass in mouse model of diabetes. Diabetes 50(10):2231-2236 doi:10.2337/diabetes.50.10.2231 (2001).
Papas et al.: Islet assessment for transplantation. CurrOpin Organ Transplant 14(6):674-682 doi:10.1097/MOT.0b013e328332a489 (2009).
Prakash et al.: Nkx6-1 controls the identity and fate of red nucleus and oculomotor neurons in the mouse midbrain. Development 136(15):2545-2555 doi:10.1242/dev.031781 (2009).
Reyes et al.: (Retracted)Purification and ex vivo expansion of postnatal human marrow mesodermal progenitor cells. Blood 98:2615-2625 [1-1] (2001).
Takahashi et al.: Induction of pluripotent stem cells from fibroblast cultures. Nat Protoc. 2(12):3081-3089 (2007).
U.S. Appl. No. 17/472,263 Non-Final Office Action dated Jan. 6, 2022.
Wimalasena: Vesicular monoamine transporters: structure-function, pharmacology, and medicinal chemistry. Med. Res. Rev.31(4):483-519 doi:10.1002/med.20187 (2011).

\* cited by examiner

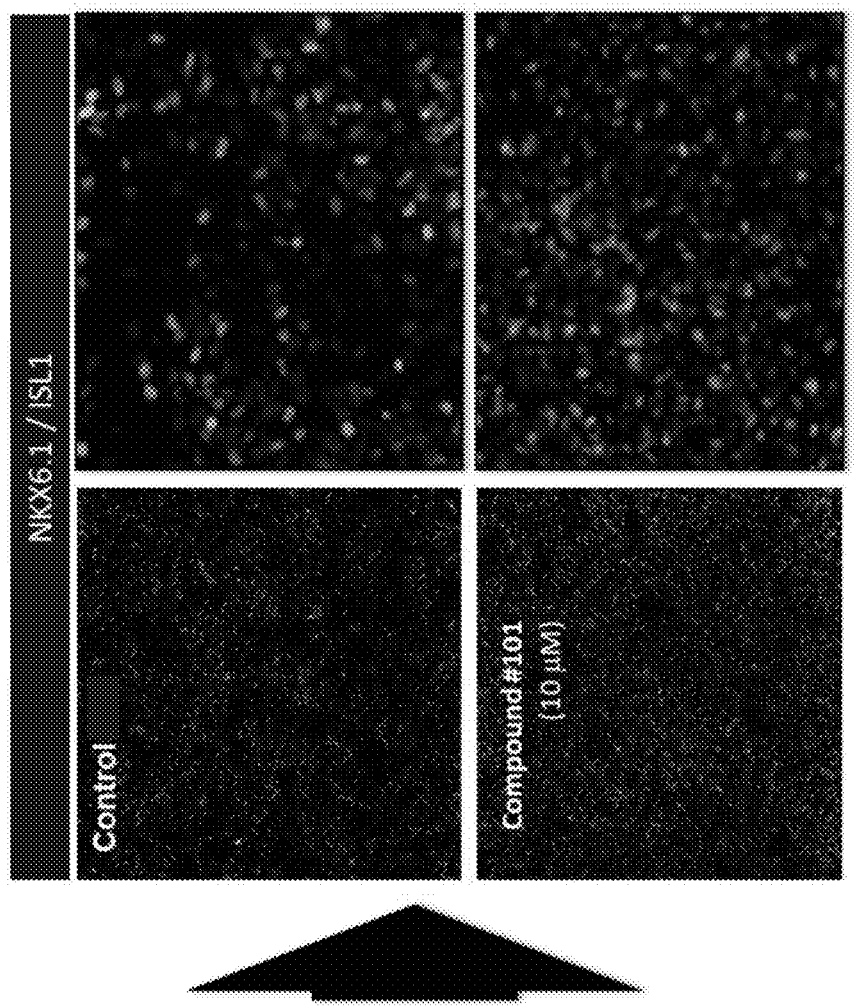
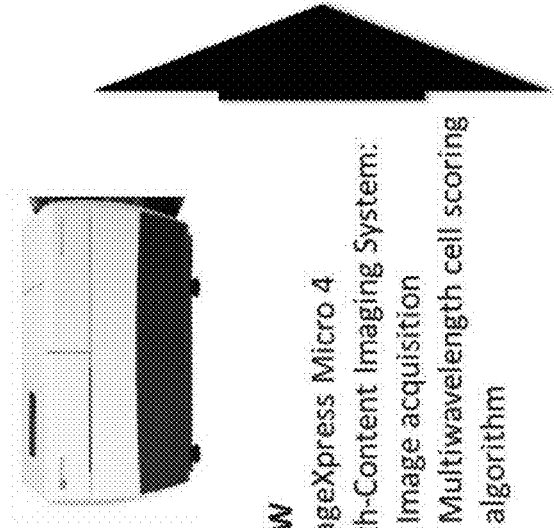
FIG. 2

| Cell Type | Screen hit | Drug targets (all inhibitors) | Primary screen result (format: 2D) | Hit validation experiment (format: 6 well) |
|---|---|---|---|---|
| b-cells | | Fold-increase in NKX6.1+/ISL1+ | | |
| | Hit #101 | Tankyrase 2 | 2.2 | 1.2 |
| | Hit #102 | Tankyrase 2 | 1.7 | 1.3 |
| | | Fold-increase in NKX6.1-/ISL1+ | | |
| | Hit #103 | BET bromodomain | 1.5 | 3.7 |
| | Hit #104 | BET bromodomain | 1.3 | 3.7 |
| a-cells | Hit #105 | BET bromodomain | 1.5 | 3.3 |
| | Hit #106 | BET bromodomain | 1.9 | 2.8 |
| | Hit #107 | Histone deacetylase | 1.4 | 2.3 |

FIG. 4

|  | Control | Hit #105 (5uM) | Hit #103 (1uM) | Hit #107 (1uM) | Hit #106 (10uM) | Hit #104 (10uM) |
|---|---|---|---|---|---|---|
| Arx+ | 7.1 | 22.8 | 31.6 | 19.2 | 22.8 | 32.9 |
| GCG+ | 4.3 | 11.1 | 2.4 | 7.7 | 7.6 | 5.1 |
| Arx+/GCG+ | 2.6 | 8.3 | 2.1 | 6.2 | 6.0 | 4.1 |

FIG. 38

STEM CELL DERIVED ISLET DIFFERENTIATION

CROSS-REFERENCE TO RELATED APPLICATION

This application is a continuation of U.S. patent application Ser. No. 17/171,497, filed on Feb. 9, 2021, which is a continuation of International Application No. PCT/US2019/045985, filed on Aug. 9, 2019, which claims the benefit of U.S. Provisional Patent Application No. 62/717,665, filed on Aug. 10, 2018, each of which is incorporated herein by reference in its entirety.

BACKGROUND

Transplantation of pancreas or pancreatic islets has been used for treating diabetes, such as type I diabetes. Pancreatic islet transplantation does not need major surgery and the function of the islet grafts can be maintained for years in a recipient. However, a shortage of pancreatic islets donors prevents this therapy from being effectively implemented. Artificial pancreas or pancreatic islets provide an alternative source of transplantable islets. Thus, there is a need for methods of in vitro restitution of pancreatic islets whose function and characteristics resemble endogenous pancreatic islets.

SUMMARY

Provided herein are methods comprising: differentiating at least a portion of a population of Pdx1 expressing pancreatic progenitor cells into a population of Pdx1 expressing, NKX6.1 expressing pancreatic progenitor cells by contacting said population of Pdx1 expressing pancreatic progenitor cells in vitro with a composition that comprises a WNT signaling inhibitor or a protein kinase C (PKC) activator, or both.

In some embodiments, the methods further comprise differentiating at least a portion of said population of Pdx1 expressing, NKX6.1 expressing pancreatic progenitor cells into a population of pancreatic endocrine progenitor cells in vitro.

In some embodiments, said composition comprises a WNT signaling inhibitor. In some embodiments, said population of pancreatic endocrine progenitor cells comprises a higher percentage of in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 30%, 35%, 40%, 45%, 50%, 55%, 60%, 65%, 70%, 75%, 80%, or 90% in vitro differentiated NKX6.1 expressing, ISL1 expressing β cells, wherein said percentage of said in vitro differentiated NKX6.1 expressing, ISL1 expressing β cells is determined prior to performance of an optional selection step. In some embodiments, said population of pancreatic endocrine progenitor cells comprises a lower percentage of in vitro differentiated cells that express neither NKX6.1 nor ISL1, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated cells that express neither NKX6.1 nor ISL1, relative to a comparable population of pancreatic endocrine progenitor cells produced by a method in which said population of Pdx1-expressing pancreatic progenitor cells are not contacted in vitro with a WNT signaling inhibitor. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated cells that express neither NKX6.1 nor ISL1, wherein said percentage of said in vitro differentiated cells that express neither NKX6.1 nor ISL1 is determined prior to performance of an optional selection step.

In some embodiments, said composition comprises a PKC activator. In some embodiments, said population of pancreatic endocrine progenitor cells comprises a higher percentage of in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated NKX6.1 non-expressing, ISL1 expressing α cells, wherein said percentage of said in vitro differentiated NKX6.1 non-expressing, ISL1 expressing α cells is determined prior to performance of an optional selection step. In some embodiments, said population of pancreatic endocrine progenitor cells comprises a higher percentage of in vitro differentiated glucagon expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated glucagon expressing α cells, relative to a comparable population of pancreatic endocrine progenitor cells produced by a method in which said population of Pdx1-expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated glucagon expressing α cells, wherein said percentage of said in vitro differentiated glucagon expressing α cells is determined prior to performance of an optional selection step. In some embodiments, said population of pancreatic endocrine progenitor cells comprises a higher percentage of in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated ARX expressing α cells, wherein said percentage of said in vitro differentiated ARX expressing α cells is determined prior to performance of an optional selection step. In some embodiments, said population of pancreatic endocrine progenitor cells comprises a lower percentage of in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated VMAT1 expressing enterochromaffin cells, wherein said percentage of said in vitro differentiated VMAT1 expressing enterochromaffin cells is determined prior to performance of an optional selection step.

In some embodiments, at least a portion of said population of pancreatic endocrine progenitor cells are matured in vitro into β cells that exhibit glucose stimulated insulin secretion (GSIS) in vitro.

In some embodiments, said WNT signaling inhibitor is a tankyrase inhibitor that inhibits expression or activity of at least one tankyrase (TNKS) protein. In some embodiments, said at least one tankyrase protein is tankyrase 1 or tankyrase 2. In some embodiments, said WNT signaling inhibitor inhibits binding of a substrate to a nicotinamide subsite or an adenosine subsite, or both, of a tankyrase protein. In some embodiments, said tankyrase inhibitor is AZ 6102, JW55, MN64, IWR-1-endo, TC-E5001, WIKI4, TNKS 22, TNKS 49, 2X-121 (E7449), XAV-939, G007-LK, NVP-TNKS656, decemotinib, (VX-509), vismodegib (GDC-0449), IM-12, GSK429286A, INO-1001, Ofloxacin, TG101209, FG-4592, I-BET-762, LY2157299, MK-0752, Wnt-C59 (C59), MC1568, Pacritinib (SB1518), SB415286, Drocinostat, IWR-1-endo, Norfloxacin, SH-4-54, Nexturastat A, SB216763, UNC0.79, dephnetin, GF109203X, RepSox, Sotrastaurin, SB431542, tofacitinib (CP-690550, Tasocitinib), AG-14361, CI994 (tacedinaline), Ro 31-8220 mesylate, resveratrol, NVP-TNKS656, or YO-01027. In some embodiments, said tankyrase inhibitor is AZ 6102, NVP-TNKS656, or IWR-1-endo.

In some embodiments, said population of Pdx1 expressing pancreatic progenitor cells are contacted in vitro with said composition that comprises a WNT signaling inhibitor for at least about 1 day, 2 days, 3 days, 4 days, 5 days, 6 days, 7 days, or 8 days. In some embodiments, said population of Pdx1 expressing pancreatic progenitor cells are contacted in vitro with said composition that comprises a WNT signaling inhibitor for from about 1-8 days, 1-7 days, 1-6 days, 1-5 days, 1-4 days, 1-3 days, or 1-2 days. In some embodiments, said population of Pdx1 expressing pancreatic progenitor cells are contacted in vitro with said composition that comprises a WNT signaling inhibitor for no more than about 1 day, 2 days, 3 days, 4 days, 5 days, 6 days, at least about 7 days, or 8 days.

In some embodiments, said population of Pdx1 expressing, NKX6.1 expressing pancreatic progenitor cells are contacted in vitro with said composition that comprises a WNT signaling inhibitor for at least about 1 day, 2 days, 3 days, 4 days, 5 days, 6 days, 7 days, or 8 days. In some embodiments, said population of Pdx1 expressing, NKX6.1 expressing pancreatic progenitor cells are contacted in vitro with said composition that comprises a WNT signaling inhibitor for from about 1-8 days, 1-7 days, 1-6 days, 1-5 days, 1-4 days, 1-3 days, or 1-2 days. In some embodiments, said population of Pdx1 expressing, NKX6.1 expressing pancreatic progenitor cells are contacted in vitro with said composition that comprises a WNT signaling inhibitor for no more than about 1 day, 2 days, 3 days, 4 days, 5 days, 6 days, at least about 7 days, or 8 days.

In some embodiments, said PKC activator is Phorbol 12,13-dibutyrate, enzastaurin, CHIR-98014, LY2157299, MK-0752, BMS-833923, avagacestat, RO4929097, DAPT (GSI-IX), hesperetin, tofacitinib, APTSTAT3-9R, SB216763, CHIR-99021, semagacestat, GF109203X, repSox, Go 6983, sotrastaurin, LGK-974, PD173955, Ro31-8220, AZD1080, LY411575, or YO-010207.

In some embodiments, said population of Pdx1 expressing pancreatic progenitor cells are contacted in vitro with said composition that comprises a PKC activator for at least about 1 day, 2 days, 3 days, 4 days, 5 days, 6 days, 7 days, or 8 days. In some embodiments, said population of Pdx1 expressing pancreatic progenitor cells are contacted in vitro with said composition that comprises a PKC activator for from about 1-8 days, 1-7 days, 1-6 days, 1-5 days, 1-4 days, 1-3 days, or 1-2 days. In some embodiments, said population of Pdx1 expressing pancreatic progenitor cells are contacted in vitro with said composition that comprises a PKC activator for no more than about 1 day, 2 days, 3 days, 4 days, 5 days, 6 days, at least about 7 days, or 8 days.

In some embodiments, said population of Pdx1 expressing, NKX6.1 expressing pancreatic progenitor cells are contacted in vitro with said composition that comprises a PKC activator for at least about 1 day, 2 days, 3 days, 4 days, 5 days, 6 days, 7 days, or 8 days. In some embodiments, said population of Pdx1 expressing, NKX6.1 expressing pancreatic progenitor cells are contacted in vitro with said composition that comprises a PKC activator for from about 1-8 days, 1-7 days, 1-6 days, 1-5 days, 1-4 days, 1-3 days, or 1-2 days. In some embodiments, said population of Pdx1 expressing, NKX6.1 expressing pancreatic progenitor cells are contacted in vitro with said composition that comprises a PKC activator for no more than about 1 day, 2 days, 3 days, 4 days, 5 days, 6 days, at least about 7 days, or 8 days.

In some embodiments, said Pdx1 expressing, progenitor cells comprise a genomic disruption in at least one gene sequence, wherein said disruption reduces or eliminates expression of a protein encoded by said gene sequence. In some embodiments, said Pdx1 expressing, NKX6.1 expressing pancreatic progenitor cells comprise a genomic disruption in at least one gene sequence, wherein said disruption reduces or eliminates expression of a protein encoded by said gene sequence. In some embodiments, said pancreatic endocrine progenitor cells comprise a genomic disruption in at least one gene sequence, wherein said disruption reduces or eliminates expression of a protein encoded by said gene sequence. In some embodiments, said β cells comprise a genomic disruption in at least one gene sequence, wherein said disruption reduces or eliminates expression of a protein encoded by said gene sequence. In some embodiments, said at least one gene sequence encodes an MHC-Class I gene. In some embodiments, said MHC-Class I gene encodes beta-2 microglobulin (B2M), HLA-A, HLA-B, or HLA-C. In some embodiments, said cells comprise a genomic disruption in a natural killer cell activating ligand gene. In some embodiments, said natural killer cell activating ligand gene encodes intercellular adhesion molecule 1 (ICAM1), CD58, CD155, carcinoembryonic antigen-related cell adhesion molecule 1 (CEACAM1), cell adhesion molecule 1 (CADM1), MHC-Class I polypeptide-related sequence A (MICA), or MHC-Class I polypeptide-related sequence B (MICB).

In some embodiments, said composition further comprises at least one, two, three, four or five agents of a keratinocyte growth factor, a sonic hedgehog antagonist, a Rho-associated coiled-coil containing protein kinase (ROCK) inhibitor, a TGF-β signaling pathway activator, or a retinoic acid signaling pathway activator, or any combination thereof.

In some embodiments, said composition further comprises at least one, two, three, four or five agents of a transforming growth factor β (TGF-β) signaling pathway inhibitor, a thyroid hormone (TH) signaling pathway activator, at least one sonic-hedgehog (SHH) pathway inhibitor, a retinoic acid (RA) signaling pathway activator, a γ-secretase inhibitor, a bone morphogenic protein (BMP) signaling pathway inhibitor, an inhibitor of Rho-associated, coiled-coil containing protein kinase (ROCK), at least one growth factor from epidermal growth factor (EGF) family, a broad kinase inhibitor, or a histone methylation inhibitor, or any combination thereof.

In some embodiments, said first composition further comprises at least one, two, three, four or five agents of a keratinocyte growth factor, a sonic hedgehog antagonist, a Rho-associated coiled-coil containing protein kinase (ROCK) inhibitor, a TGF-β signaling pathway activator, or a retinoic acid signaling pathway activator, or any combination thereof.

In some embodiments, said second composition further comprises at least one, two, three, four or five agents of a transforming growth factor β (TGF-β) signaling pathway inhibitor, a thyroid hormone (TH) signaling pathway activator, at least one sonic-hedgehog (SHH) pathway inhibitor, a retinoic acid (RA) signaling pathway activator, a γ-secretase inhibitor, a bone morphogenic protein (BMP) signaling pathway inhibitor, an inhibitor of Rho-associated, coiled-coil containing protein kinase (ROCK), at least one growth factor from epidermal growth factor (EGF) family, a broad kinase inhibitor, or a histone methylation inhibitor, or any combination thereof.

Provided herein are methods comprising: differentiating at least a portion of a population of Pdx1 expressing, NKX6.1 expressing pancreatic progenitor cells into a population of pancreatic endocrine progenitor cells by contacting said population of Pdx1 expressing, NKX6.1 expressing pancreatic progenitor cells in vitro with a composition that comprises a WNT signaling inhibitor or a protein kinase C (PKC) activator, or both.

In some embodiments, said composition comprises a WNT signaling inhibitor. In some embodiments, said population of pancreatic endocrine progenitor cells comprises a higher percentage of in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 30%, 35%, 40%, 45%, 50%, 55%, 60%, 65%, 70%, 75%, 80%, or 90% in vitro differentiated NKX6.1 expressing, ISL1 expressing β cells, wherein said percentage of said in vitro differentiated NKX6.1 expressing, ISL1 expressing β cells is determined prior to performance of an optional selection step. In some embodiments, said population of pancreatic endocrine progenitor cells comprises a lower percentage of in vitro differentiated cells that express neither NKX6.1 nor ISL1, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated cells that express neither NKX6.1 nor ISL1, relative to a comparable population of pancreatic endocrine progenitor cells produced by a method in which said population of Pdx1-expressing pancreatic progenitor cells are not contacted in vitro with a WNT signaling inhibitor. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated cells that express neither NKX6.1 nor ISL1, wherein said percentage of said in vitro differentiated cells that express neither NKX6.1 nor ISL1 is determined prior to performance of an optional selection step.

In some embodiments, said composition comprises a PKC activator. In some embodiments, said population of pancreatic endocrine progenitor cells comprises a higher percentage of in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated NKX6.1 non-expressing, ISL1 expressing α cells, wherein said percentage of said in vitro differentiated NKX6.1 non-expressing, ISL1 expressing α cells is determined prior to performance of an optional selection step. In some embodiments, said population of pancreatic endocrine progenitor cells comprises a higher percentage of in vitro differentiated glucagon expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated glucagon expressing α cells, relative to a comparable population of pancreatic endocrine progenitor cells produced by a method in which said population of Pdx1-expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated glucagon expressing α cells, wherein said percentage of said in vitro differentiated glucagon expressing α cells is determined prior to performance of an optional selection step. In some embodiments, said population of pancreatic endocrine progenitor cells comprises a higher percentage of in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated ARX expressing α cells, wherein said percentage of said in vitro differentiated ARX expressing α cells is determined prior to performance of an optional selection step. In some embodiments, said population of pancreatic endocrine progenitor cells comprises a lower percentage of in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated VMAT1 expressing enterochromaffin cells, wherein said percentage of said in vitro differentiated VMAT1 expressing enterochromaffin cells is determined prior to performance of an optional selection step.

In some embodiments, at least a portion of said population of pancreatic endocrine progenitor cells are matured in vitro into β cells that exhibit glucose stimulated insulin secretion (GSIS) in vitro.

In some embodiments, said WNT signaling inhibitor is a tankyrase inhibitor that inhibits expression or activity of at least one tankyrase (TNKS) protein. In some embodiments, said at least one tankyrase protein is tankyrase 1 or tankyrase 2. In some embodiments, said WNT signaling inhibitor inhibits binding of a substrate to a nicotinamide subsite or an adenosine subsite, or both, of a tankyrase protein. In some embodiments, said tankyrase inhibitor is AZ 6102, JW55, MN64, IWR-1-endo, TC-E5001, WIKI4, TNKS 22, TNKS 49, 2X-121 (E7449), XAV-939, G007-LK, NVP-TNKS656, decemotinib, (VX-509), vismodegib (GDC-0449), IM-12, GSK429286A, INO-1001, Ofloxacin, TG101209, FG-4592, I-BET-762, LY2157299, MK-0752, Wnt-C59 (C59), MC1568, Pacritinib (SB1518), SB415286, Drocinostat, IWR-1-endo, Norfloxacin, SH-4-54, Nexturastat A, SB216763, UNC0.79, dephnetin, GF109203X, RepSox, Sotrastaurin, SB431542, tofacitinib (CP-690550, Tasocitinib), AG-14361, CI994 (tacedinaline), Ro 31-8220 mesylate, resveratrol, NVP-TNKS656, or YO-01027. In some embodiments, said tankyrase inhibitor is AZ 6102, NVP-TNKS656, or IWR-1-endo.

In some embodiments, said population of Pdx1 expressing pancreatic progenitor cells are contacted in vitro with said composition that comprises a WNT signaling inhibitor for at least about 1 day, 2 days, 3 days, 4 days, 5 days, 6 days, 7 days, or 8 days. In some embodiments, said population of Pdx1 expressing pancreatic progenitor cells are contacted in vitro with said composition that comprises a WNT signaling inhibitor for from about 1-8 days, 1-7 days, 1-6 days, 1-5 days, 1-4 days, 1-3 days, or 1-2 days. In some embodiments, said population of Pdx1 expressing pancreatic progenitor cells are contacted in vitro with said composition that comprises a WNT signaling inhibitor for no more than about 1 day, 2 days, 3 days, 4 days, 5 days, 6 days, at least about 7 days, or 8 days.

In some embodiments, said population of Pdx1 expressing, NKX6.1 expressing pancreatic progenitor cells are contacted in vitro with said composition that comprises a WNT signaling inhibitor for at least about 1 day, 2 days, 3 days, 4 days, 5 days, 6 days, 7 days, or 8 days. In some embodiments, said population of Pdx1 expressing, NKX6.1 expressing pancreatic progenitor cells are contacted in vitro with said composition that comprises a WNT signaling inhibitor for from about 1-8 days, 1-7 days, 1-6 days, 1-5 days, 1-4 days, 1-3 days, or 1-2 days. In some embodiments, said population of Pdx1 expressing, NKX6.1 expressing pancreatic progenitor cells are contacted in vitro with said composition that comprises a WNT signaling inhibitor for no more than about 1 day, 2 days, 3 days, 4 days, 5 days, 6 days, at least about 7 days, or 8 days.

In some embodiments, said PKC activator is Phorbol 12,13-dibutyrate, enzastaurin, CHIR-98014, LY2157299, MK-0752, BMS-833923, avagacestat, RO4929097, DAPT (GSI-IX), hesperetin, tofacitinib, APTSTAT3-9R, SB216763, CHIR-99021, semagacestat, GF109203X, repSox, Go 6983, sotrastaurin, LGK-974, PD173955, Ro31-8220, AZD1080, LY411575, or YO-010207.

In some embodiments, said population of Pdx1 expressing pancreatic progenitor cells are contacted in vitro with said composition that comprises a PKC activator for at least about 1 day, 2 days, 3 days, 4 days, 5 days, 6 days, 7 days, or 8 days. In some embodiments, said population of Pdx1 expressing pancreatic progenitor cells are contacted in vitro with said composition that comprises a PKC activator for from about 1-8 days, 1-7 days, 1-6 days, 1-5 days, 1-4 days, 1-3 days, or 1-2 days. In some embodiments, said population of Pdx1 expressing pancreatic progenitor cells are contacted in vitro with said composition that comprises a PKC activator for no more than about 1 day, 2 days, 3 days, 4 days, 5 days, 6 days, at least about 7 days, or 8 days.

In some embodiments, said population of Pdx1 expressing, NKX6.1 expressing pancreatic progenitor cells are contacted in vitro with said composition that comprises a PKC activator for at least about 1 day, 2 days, 3 days, 4 days, 5 days, 6 days, 7 days, or 8 days. In some embodiments, said population of Pdx1 expressing, NKX6.1 expressing pancreatic progenitor cells are contacted in vitro with said composition that comprises a PKC activator for from about 1-8 days, 1-7 days, 1-6 days, 1-5 days, 1-4 days, 1-3 days, or 1-2 days. In some embodiments, said population of Pdx1 expressing, NKX6.1 expressing pancreatic progenitor cells are contacted in vitro with said composition that comprises a PKC activator for no more than about 1 day, 2 days, 3 days, 4 days, 5 days, 6 days, at least about 7 days, or 8 days.

In some embodiments, said Pdx1 expressing pancreatic progenitor cells comprise a genomic disruption in at least one gene sequence, wherein said disruption reduces or eliminates expression of a protein encoded by said gene sequence. In some embodiments, said Pdx1 expressing, NKX6.1 expressing pancreatic progenitor cells comprise a genomic disruption in at least one gene sequence, wherein said disruption reduces or eliminates expression of a protein encoded by said gene sequence. In some embodiments, said pancreatic endocrine progenitor cells comprise a genomic disruption in at least one gene sequence, wherein said disruption reduces or eliminates expression of a protein encoded by said gene sequence. In some embodiments, said β cells comprise a genomic disruption in at least one gene sequence, wherein said disruption reduces or eliminates expression of a protein encoded by said gene sequence. In some embodiments, said at least one gene sequence encodes an MHC-Class I gene. In some embodiments, said MHC-Class I gene encodes beta-2 microglobulin (B2M), HLA-A, HLA-B, or HLA-C. In some embodiments, said cells comprise a genomic disruption in a natural killer cell activating ligand gene. In some embodiments, said natural killer cell activating ligand gene encodes intercellular adhesion molecule 1 (ICAM1), CD58, CD155, carcinoembryonic antigen-related cell adhesion molecule 1 (CEACAM1), cell adhesion molecule 1 (CADM1), MHC-Class I polypeptide-related sequence A (MICA), or MHC-Class I polypeptide-related sequence B (MICB).

In some embodiments, said composition further comprises at least one, two, three, four or five agents of a keratinocyte growth factor, a sonic hedgehog antagonist, a Rho-associated coiled-coil containing protein kinase (ROCK) inhibitor, a TGF-β signaling pathway activator, or a retinoic acid signaling pathway activator, or any combination thereof.

In some embodiments, said composition further comprises at least one, two, three, four or five agents of a transforming growth factor β (TGF-β) signaling pathway inhibitor, a thyroid hormone (TH) signaling pathway activator, at least one sonic-hedgehog (SHH) pathway inhibitor, a retinoic acid (RA) signaling pathway activator, a γ-secretase inhibitor, a bone morphogenic protein (BMP) signaling pathway inhibitor, an inhibitor of Rho-associated, coiled-coil containing protein kinase (ROCK), at least one growth factor from epidermal growth factor (EGF) family, a broad kinase inhibitor, or a histone methylation inhibitor, or any combination thereof.

In some embodiments, said first composition further comprises at least one, two, three, four or five agents of a keratinocyte growth factor, a sonic hedgehog antagonist, a Rho-associated coiled-coil containing protein kinase (ROCK) inhibitor, a TGF-β signaling pathway activator, or a retinoic acid signaling pathway activator, or any combination thereof.

In some embodiments, said second composition further comprises at least one, two, three, four or five agents of a transforming growth factor β (TGF-β) signaling pathway inhibitor, a thyroid hormone (TH) signaling pathway activator, at least one sonic-hedgehog (SHH) pathway inhibitor, a retinoic acid (RA) signaling pathway activator, a γ-secretase inhibitor, a bone morphogenic protein (BMP) signaling pathway inhibitor, an inhibitor of Rho-associated, coiled-coil containing protein kinase (ROCK), at least one growth factor from epidermal growth factor (EGF) family, a broad kinase inhibitor, or a histone methylation inhibitor, or any combination thereof.

Provided herein are methods comprising: differentiating at least a portion of a population of Pdx1 expressing pancreatic progenitor cells into a population of Pdx1 expressing, NKX6.1 expressing pancreatic progenitor cells by contacting said population of Pdx1 expressing pancreatic progenitor cells in vitro with a first composition that comprises a WNT signaling inhibitor or a protein kinase C (PKC) activator, or both; and differentiating said Pdx1 expressing, NKX6.1 expressing pancreatic progenitor cells into pancreatic endocrine progenitor cells by contacting said population of Pdx1 expressing, NKX6.1 expressing pancreatic progenitor cells in vitro with a second composition that comprises a WNT signaling inhibitor or a protein kinase C (PKC) activator, or both.

In some embodiments, said composition comprises a WNT signaling inhibitor. In some embodiments, said population of pancreatic endocrine progenitor cells comprises a higher percentage of in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 30%, 35%, 40%, 45%, 50%, 55%, 60%, 65%, 70%, 75%, 80%, or 90% in vitro differentiated NKX6.1 expressing, ISL1 expressing β cells, wherein said percentage of said in vitro differentiated NKX6.1 expressing, ISL1 expressing β cells is determined prior to performance of an optional selection step. In some embodiments, said population of pancreatic endocrine progenitor cells comprises a lower percentage of in vitro differentiated cells that express neither NKX6.1 nor ISL1, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated cells that express neither NKX6.1 nor ISL1, relative to a comparable population of pancreatic endocrine progenitor cells produced by a method in which said population of Pdx1-expressing pancreatic progenitor cells are not contacted in vitro with a WNT signaling inhibitor. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated cells that express neither NKX6.1 nor ISL1, wherein said percentage of said in vitro differentiated cells that express neither NKX6.1 nor ISL1 is determined prior to performance of an optional selection step.

In some embodiments, said composition comprises a PKC activator. In some embodiments, said population of pancreatic endocrine progenitor cells comprises a higher percentage of in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated NKX6.1 non-expressing, ISL1 expressing α cells, wherein said percentage of said in vitro differentiated NKX6.1 non-expressing, ISL1 expressing α cells is determined prior to performance of an optional selection step. In some embodiments, said population of pancreatic endocrine progenitor cells comprises a higher percentage of in vitro differentiated glucagon expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated glucagon expressing α cells, relative to a comparable population of pancreatic endocrine progenitor cells produced by a method in which said population of Pdx1-expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated glucagon expressing α cells, wherein said percentage of said in vitro differentiated glucagon expressing α cells is determined prior to performance of an optional selection step. In some embodiments, said population of pancreatic endocrine progenitor cells comprises a higher percentage of in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated ARX expressing α cells, wherein said percentage of said in vitro differentiated ARX expressing α cells is determined prior to performance of an optional selection step. In some embodiments, said population of pancreatic endocrine progenitor cells comprises a lower percentage of in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated VMAT1 expressing enterochromaffin cells, wherein said percentage of said in vitro differentiated VMAT1 expressing enterochromaffin cells is determined prior to performance of an optional selection step.

In some embodiments, at least a portion of said population of pancreatic endocrine progenitor cells are matured in vitro into β cells that exhibit glucose stimulated insulin secretion (GSIS) in vitro.

In some embodiments, said WNT signaling inhibitor is a tankyrase inhibitor that inhibits expression or activity of at least one tankyrase (TNKS) protein. In some embodiments, said at least one tankyrase protein is tankyrase 1 or tankyrase 2. In some embodiments, said WNT signaling inhibitor inhibits binding of a substrate to a nicotinamide subsite or an adenosine subsite, or both, of a tankyrase protein. In some embodiments, said tankyrase inhibitor is AZ 6102, JW55, MN64, IWR-1-endo, TC-E5001, WIKI4, TNKS 22, TNKS 49, 2X-121 (E7449), XAV-939, G007-LK, NVP-TNKS656, decemotinib, (VX-509), vismodegib (GDC-0449), IM-12, GSK429286A, INO-1001, Ofloxacin, TG101209, FG-4592, I-BET-762, LY2157299, MK-0752, Wnt-C59 (C59), MC1568, Pacritinib (SB1518), SB415286, Drocinostat, IWR-1-endo, Norfloxacin, SH-4-54, Nexturastat A, SB216763, UNC0.79, dephnetin, GF109203X, RepSox, Sotrastaurin, SB431542, tofacitinib (CP-690550, Tasocitinib), AG-14361, C1994 (tacedinaline), Ro 31-8220 mesylate, resveratrol, NVP-TNKS656, or YO-01027. In some embodiments, said tankyrase inhibitor is AZ 6102, NVP-TNKS656, or IWR-1-endo.

In some embodiments, said population of Pdx1 expressing pancreatic progenitor cells are contacted in vitro with said composition that comprises a WNT signaling inhibitor for at least about 1 day, 2 days, 3 days, 4 days, 5 days, 6 days, 7 days, or 8 days. In some embodiments, said population of Pdx1 expressing pancreatic progenitor cells are contacted in vitro with said composition that comprises a WNT signaling inhibitor for from about 1-8 days, 1-7 days, 1-6 days, 1-5 days, 1-4 days, 1-3 days, or 1-2 days. In some embodiments, said population of Pdx1 expressing pancreatic progenitor cells are contacted in vitro with said composition that comprises a WNT signaling inhibitor for no more than about 1 day, 2 days, 3 days, 4 days, 5 days, 6 days, at least about 7 days, or 8 days.

In some embodiments, said population of Pdx1 expressing, NKX6.1 expressing pancreatic progenitor cells are contacted in vitro with said composition that comprises a WNT signaling inhibitor for at least about 1 day, 2 days, 3 days, 4 days, 5 days, 6 days, 7 days, or 8 days. In some embodiments, said population of Pdx1 expressing, NKX6.1 expressing pancreatic progenitor cells are contacted in vitro with said composition that comprises a WNT signaling inhibitor for from about 1-8 days, 1-7 days, 1-6 days, 1-5 days, 1-4 days, 1-3 days, or 1-2 days. In some embodiments, said population of Pdx1 expressing, NKX6.1 expressing pancreatic progenitor cells are contacted in vitro with said composition that comprises a WNT signaling inhibitor for no more than about 1 day, 2 days, 3 days, 4 days, 5 days, 6 days, at least about 7 days, or 8 days.

In some embodiments, said PKC activator is Phorbol 12,13-dibutyrate, enzastaurin, CHIR-98014, LY2157299, MK-0752, BMS-833923, avagacestat, RO4929097, DAPT (GSI-IX), hesperetin, tofacitinib, APTSTAT3-9R, SB216763, CHIR-99021, semagacestat, GF109203X, repSox, Go 6983, sotrastaurin, LGK-974, PD173955, Ro31-8220, AZD1080, LY411575, or YO-010207.

In some embodiments, said population of Pdx1 expressing pancreatic progenitor cells are contacted in vitro with said composition that comprises a PKC activator for at least about 1 day, 2 days, 3 days, 4 days, 5 days, 6 days, 7 days, or 8 days. In some embodiments, said population of Pdx1 expressing pancreatic progenitor cells are contacted in vitro with said composition that comprises a PKC activator for from about 1-8 days, 1-7 days, 1-6 days, 1-5 days, 1-4 days, 1-3 days, or 1-2 days. In some embodiments, said population of Pdx1 expressing pancreatic progenitor cells are contacted in vitro with said composition that comprises a PKC activator for no more than about 1 day, 2 days, 3 days, 4 days, 5 days, 6 days, at least about 7 days, or 8 days.

In some embodiments, said population of Pdx1 expressing, NKX6.1 expressing pancreatic progenitor cells are contacted in vitro with said composition that comprises a PKC activator for at least about 1 day, 2 days, 3 days, 4 days, 5 days, 6 days, 7 days, or 8 days. In some embodiments, said population of Pdx1 expressing, NKX6.1 expressing pancreatic progenitor cells are contacted in vitro with said composition that comprises a PKC activator for from about 1-8 days, 1-7 days, 1-6 days, 1-5 days, 1-4 days, 1-3 days, or 1-2 days. In some embodiments, said population of Pdx1 expressing, NKX6.1 expressing pancreatic progenitor cells are contacted in vitro with said composition that comprises a PKC activator for no more than about 1 day, 2 days, 3 days, 4 days, 5 days, 6 days, at least about 7 days, or 8 days.

In some embodiments, said Pdx1 expressing pancreatic progenitor cells comprise a genomic disruption in at least one gene sequence, wherein said disruption reduces or eliminates expression of a protein encoded by said gene sequence. In some embodiments, said Pdx1 expressing, NKX6.1 expressing pancreatic progenitor cells comprise a genomic disruption in at least one gene sequence, wherein said disruption reduces or eliminates expression of a protein encoded by said gene sequence. In some embodiments, said pancreatic endocrine progenitor cells comprise a genomic disruption in at least one gene sequence, wherein said disruption reduces or eliminates expression of a protein encoded by said gene sequence. In some embodiments, said β cells comprise a genomic disruption in at least one gene sequence, wherein said disruption reduces or eliminates expression of a protein encoded by said gene sequence. In some embodiments, said at least one gene sequence encodes an MHC-Class I gene. In some embodiments, said MHC-Class I gene encodes beta-2 microglobulin (B2M), HLA-A, HLA-B, or HLA-C. In some embodiments, said cells comprise a genomic disruption in a natural killer cell activating ligand gene. In some embodiments, said natural killer cell activating ligand gene encodes intercellular adhesion molecule 1 (ICAM1), CD58, CD155, carcinoembryonic antigen-related cell adhesion molecule 1 (CEACAM1), cell adhesion molecule 1 (CADM1), MHC-Class I polypeptide-related sequence A (MICA), or MHC-Class I polypeptide-related sequence B (MICB).

In some embodiments, said composition further comprises at least one, two, three, four or five agents of a keratinocyte growth factor, a sonic hedgehog antagonist, a Rho-associated coiled-coil containing protein kinase (ROCK) inhibitor, a TGF-β signaling pathway activator, or a retinoic acid signaling pathway activator, or any combination thereof.

In some embodiments, said composition further comprises at least one, two, three, four or five agents of a transforming growth factor β (TGF-β) signaling pathway inhibitor, a thyroid hormone (TH) signaling pathway activator, at least one sonic-hedgehog (SHH) pathway inhibitor, a retinoic acid (RA) signaling pathway activator, a γ-secretase inhibitor, a bone morphogenic protein (BMP) signaling pathway inhibitor, an inhibitor of Rho-associated, coiled-coil containing protein kinase (ROCK), at least one growth factor from epidermal growth factor (EGF) family, a broad kinase inhibitor, or a histone methylation inhibitor, or any combination thereof.

In some embodiments, said first composition further comprises at least one, two, three, four or five agents of a keratinocyte growth factor, a sonic hedgehog antagonist, a Rho-associated coiled-coil containing protein kinase (ROCK) inhibitor, a TGF-β signaling pathway activator, or a retinoic acid signaling pathway activator, or any combination thereof.

In some embodiments, said second composition further comprises at least one, two, three, four or five agents of a transforming growth factor β (TGF-β) signaling pathway inhibitor, a thyroid hormone (TH) signaling pathway activator, at least one sonic-hedgehog (SHH) pathway inhibitor, a retinoic acid (RA) signaling pathway activator, a γ-secretase inhibitor, a bone morphogenic protein (BMP) signaling pathway inhibitor, an inhibitor of Rho-associated, coiled-coil containing protein kinase (ROCK), at least one growth factor from epidermal growth factor (EGF) family, a broad kinase inhibitor, or a histone methylation inhibitor, or any combination thereof.

Provided herein are methods comprising: differentiating a plurality of stem cells in vitro to obtain a cell population that comprises Pdx1 expressing pancreatic progenitor cells; differentiating at least a portion of said Pdx1 expressing pancreatic progenitor cells into Pdx1 expressing, NKX6.1 expressing pancreatic progenitor cells, by contacting said population of Pdx1 expressing pancreatic progenitor cells in vitro with a first composition that comprises a Wnt signaling inhibitor or a PKC activator, or both; and at least one, two, three, four or five agents selected from the group consisting of a keratinocyte growth factor, a sonic hedgehog antagonist, a Rho-associated coiled-coil containing protein kinase (ROCK) inhibitor, a TGF-β signaling pathway activator, and a retinoic acid signaling pathway activator; and a Wnt signaling inhibitor, to thereby generate a population of Pdx1 expressing, NKX6.1 expressing pancreatic progenitor cells; and differentiating at least a portion of said population of Pdx1 expressing, NKX6.1 expressing pancreatic progenitor cells into pancreatic endocrine progenitor cells, by contacting said population of Pdx1 expressing, NKX6.1 expressing pancreatic progenitor cells in vitro with a with a second composition that comprises at least one, two, three, four or five agents of a transforming growth factor β (TGF-β) signaling pathway inhibitor, a thyroid hormone (TH) signaling pathway activator, at least one sonic-hedgehog (SHH) pathway inhibitor, a retinoic acid (RA) signaling pathway activator, a γ-secretase inhibitor, a bone morphogenic protein (BMP) signaling pathway inhibitor, an inhibitor of Rho-associated, coiled-coil containing protein kinase (ROCK), at least one growth factor from epidermal growth factor (EGF) family, a broad kinase inhibitor, a histone methylation inhibitor, to thereby generate a population of pancreatic endocrine progenitor cells.

In some embodiments, said population of pancreatic endocrine progenitor cells comprises NKX6.1 expressing, ISL1 expressing β cells, NKX6.1 non-expressing, ISL1 expressing α cells. In some embodiments, said second composition comprises a Wnt signaling inhibitor or a PKC activator, or both. In some embodiments, said method further comprises maturing said at least one endocrine cell in vitro to obtain a population of cells that comprises NKX6.1 expressing, ISL1 expressing β cells that exhibit glucose stimulated insulin secretion in vitro.

In some embodiments, said WNT signaling inhibitor is a tankyrase inhibitor that inhibits expression or activity of at least one tankyrase (TNKS) protein. In some embodiments, said at least one tankyrase protein is tankyrase 1 or tankyrase 2. In some embodiments, said WNT signaling inhibitor inhibits binding of a substrate to a nicotinamide subsite or an adenosine subsite, or both, of a tankyrase protein. In some embodiments, said tankyrase inhibitor is AZ 6102, JW55, MN64, IWR-1-endo, TC-E5001, WIKI4, TNKS 22, TNKS 49, 2X-121 (E7449), XAV-939, G007-LK, NVP-TNKS656, decemotinib, (VX-509), vismodegib (GDC-0449), IM-12, GSK429286A, INO-1001, Ofloxacin, TG101209, FG-4592, I-BET-762, LY2157299, MK-0752, Wnt-C59 (C59), MC1568, Pacritinib (SB1518), SB415286, Drocinostat, IWR-1-endo, Norfloxacin, SH-4-54, Nexturastat A, SB216763, UNC0.79, dephnetin, GF109203X, RepSox, Sotrastaurin, SB431542, tofacitinib (CP-690550, Tasocitinib), AG-14361, CI994 (tacedinaline), Ro 31-8220 mesylate, resveratrol, NVP-TNKS656, or YO-01027. In some embodiments, said tankyrase inhibitor is AZ 6102, NVP-TNKS656, or IWR-1-endo.

In some embodiments, said population of Pdx1 expressing pancreatic progenitor cells are contacted in vitro with said composition that comprises a WNT signaling inhibitor for at least about 1 day, 2 days, 3 days, 4 days, 5 days, 6 days, 7 days, or 8 days. In some embodiments, said population of Pdx1 expressing pancreatic progenitor cells are contacted in vitro with said composition that comprises a WNT signaling inhibitor for from about 1-8 days, 1-7 days, 1-6 days, 1-5 days, 1-4 days, 1-3 days, or 1-2 days. In some embodiments, said population of Pdx1 expressing pancreatic progenitor cells are contacted in vitro with said composition that comprises a WNT signaling inhibitor for no more than about 1 day, 2 days, 3 days, 4 days, 5 days, 6 days, at least about 7 days, or 8 days.

In some embodiments, said population of Pdx1 expressing, NKX6.1 expressing pancreatic progenitor cells are contacted in vitro with said composition that comprises a WNT signaling inhibitor for at least about 1 day, 2 days, 3 days, 4 days, 5 days, 6 days, 7 days, or 8 days. In some embodiments, said population of Pdx1 expressing, NKX6.1 expressing pancreatic progenitor cells are contacted in vitro with said composition that comprises a WNT signaling inhibitor for from about 1-8 days, 1-7 days, 1-6 days, 1-5 days, 1-4 days, 1-3 days, or 1-2 days. In some embodiments, said population of Pdx1 expressing, NKX6.1 expressing pancreatic progenitor cells are contacted in vitro with said composition that comprises a WNT signaling inhibitor for no more than about 1 day, 2 days, 3 days, 4 days, 5 days, 6 days, at least about 7 days, or 8 days.

In some embodiments, said PKC activator is Phorbol 12,13-dibutyrate, enzastaurin, CHIR-98014, LY2157299, MK-0752, BMS-833923, avagacestat, RO4929097, DAPT (GSI-IX), hesperetin, tofacitinib, APTSTAT3-9R, SB216763, CHIR-99021, semagacestat, GF109203X, repSox, Go 6983, sotrastaurin, LGK-974, PD173955, Ro31-8220, AZD1080, LY411575, or YO-010207.

In some embodiments, said population of Pdx1 expressing pancreatic progenitor cells are contacted in vitro with said composition that comprises a PKC activator for at least about 1 day, 2 days, 3 days, 4 days, 5 days, 6 days, 7 days, or 8 days. In some embodiments, said population of Pdx1 expressing pancreatic progenitor cells are contacted in vitro with said composition that comprises a PKC activator for from about 1-8 days, 1-7 days, 1-6 days, 1-5 days, 1-4 days, 1-3 days, or 1-2 days. In some embodiments, said population of Pdx1 expressing pancreatic progenitor cells are contacted in vitro with said composition that comprises a PKC activator for no more than about 1 day, 2 days, 3 days, 4 days, 5 days, 6 days, at least about 7 days, or 8 days.

In some embodiments, said population of Pdx1 expressing, NKX6.1 expressing pancreatic progenitor cells are contacted in vitro with said composition that comprises a PKC activator for at least about 1 day, 2 days, 3 days, 4 days, 5 days, 6 days, 7 days, or 8 days. In some embodiments, said population of Pdx1 expressing, NKX6.1 expressing pancreatic progenitor cells are contacted in vitro with said composition that comprises a PKC activator for from about 1-8 days, 1-7 days, 1-6 days, 1-5 days, 1-4 days, 1-3 days, or 1-2 days. In some embodiments, said population of Pdx1 expressing, NKX6.1 expressing pancreatic progenitor cells are contacted in vitro with said composition that comprises a PKC activator for no more than about 1 day, 2 days, 3 days, 4 days, 5 days, 6 days, at least about 7 days, or 8 days.

In some embodiments, said Pdx1 expressing pancreatic progenitor cells comprise a genomic disruption in at least one gene sequence, wherein said disruption reduces or eliminates expression of a protein encoded by said gene sequence. In some embodiments, said Pdx1 expressing, NKX6.1 expressing pancreatic progenitor cells comprise a genomic disruption in at least one gene sequence, wherein said disruption reduces or eliminates expression of a protein encoded by said gene sequence. In some embodiments, said pancreatic endocrine progenitor cells comprise a genomic disruption in at least one gene sequence, wherein said disruption reduces or eliminates expression of a protein encoded by said gene sequence. In some embodiments, said β cells comprise a genomic disruption in at least one gene sequence, wherein said disruption reduces or eliminates expression of a protein encoded by said gene sequence. In some embodiments, said at least one gene sequence encodes an MHC-Class I gene. In some embodiments, said MHC-Class I gene encodes beta-2 microglobulin (B2M), HLA-A, HLA-B, or HLA-C. In some embodiments, said cells comprise a genomic disruption in a natural killer cell activating ligand gene. In some embodiments, said natural killer cell activating ligand gene encodes intercellular adhesion molecule 1 (ICAM1), CD58, CD155, carcinoembryonic antigen-related cell adhesion molecule 1 (CEACAM1), cell adhesion molecule 1 (CADM1), MHC-Class I polypeptide-related sequence A (MICA), or MHC-Class I polypeptide-related sequence B (MICB).

Provided herein are compositions that comprises population of cells produced by a method described herein. Provided herein are populations of in vitro differentiated Pdx1 expressing pancreatic progenitor cells and a Wnt inhibitor, a PKC activator, or both. Provided herein are populations of in vitro differentiated Pdx1 expressing, NKX6.1 expressing pancreatic progenitor cells and a Wnt inhibitor, a PKC activator, or both. Provided herein are populations of in vitro differentiated pancreatic endocrine progenitor cells and a Wnt inhibitor, a PKC activator, or both. In some embodiments, said in vitro differentiated pancreatic endocrine progenitor cells comprise NKX6.1 expressing, ISL1 expressing β cells or NKX6.1 non-expressing, ISL1 expressing α cells, or both.

Provided herein are devices that comprises a population of cells produced by a method described herein. Provided herein are devices that comprises a composition of cells described herein. In some embodiments, said device is configured for placement into a human subject.

Provided herein are methods of treating a human subject with a disease characterized by high blood sugar levels over a prolonged period of time, the method comprising administering said subject a cell composition described herein. Provided herein are methods of treating a subject with a disease characterized by high blood sugar levels over a prolonged period of time, the method comprising implanting a device described herein into said subject. In some embodiments, said disease is diabetes.

One aspect of the present disclosure provides a method comprising: contacting a population of cells comprising pancreatic progenitor cells or precursors thereof with a composition comprising a WNT signaling inhibitor, thereby differentiating the pancreatic progenitor cells or precursors thereof into pancreatic β cells.

In some embodiments, the contacting results in a second population of cells comprising a larger percentage of the pancreatic β cells as compared to a corresponding population of cells comprising the pancreatic β cells which is not contacted with the WNT signaling inhibitor. In some embodiments, the WNT signaling inhibitor inhibits expression or activity of Tankyrase.

Another aspect of the present disclosure provides a method comprising: contacting a population of cells comprising pancreatic progenitor cells or precursors thereof with a composition comprising a compound that inhibits expression or activity of Tankyrase, thereby differentiating the pancreatic progenitor cells or precursors thereof into pancreatic β cells.

In some embodiments, the contacting results in a second population of cells comprising a larger percentage of the pancreatic β cells as compared to a corresponding population of cells comprising the pancreatic β cells which is not contacted with the compound that inhibits expression or activity of Tankyrase. In some embodiments, the pancreatic β cells are NKX6.1 and ISL1 double positive. In some embodiments, the second population of cells comprises at least 25%, at least 30%, at least 35%, at least 40%, at least 45%, or at least 50% pancreatic β cells. In some embodiments, the second population of cells comprises at least 150%, at least 180%, at least 200%, at least 220%, or at least 250% more pancreatic β cells as compared to the corresponding population of cells which is not contacted with the WNT signaling inhibitor or the compound that inhibits expression or activity of Tankyrase. In some embodiments, the WNT signaling inhibitor or the compound that inhibits expression or activity of Tankyrase inhibits adenosine binding site, nicotinamide binding site, or both of Tankyrase. In some embodiments, the WNT signaling inhibitor or the compound that inhibits expression or activity of Tankyrase comprises AZ 6102, JW55, MN64, IWR-1-endo, TC-E5001, WIKI4, TNKS 22, TNKS 49, 2X-121 (E7449), XAV-939, G007-LK, or NVP-TNKS656. In some embodiments, the pancreatic progenitor cells or precursors thereof are contacted with between 0.01 and 500 μM of the WNT signaling inhibitor or the compound that inhibits expression or activity of Tankyrase. In some embodiments, the pancreatic progenitor cells or precursors thereof are contacted with between 0.1 and 100 μM of the WNT signaling inhibitor or the compound that inhibits expression or activity of Tankyrase. In some embodiments, the pancreatic progenitor cells or precursors thereof are contacted with about 1, about 5, or about 10 μM of the WNT signaling inhibitor or the compound that inhibits expression or activity of Tankyrase. In some embodiments, the pancreatic progenitor cells or precursors thereof are contacted with the WNT signaling inhibitor or the compound that inhibits expression or activity of Tankyrase for at least 1, at least 2, at least 3, at least 4, at least 5, at least 6, at least 7, or at least 8 days. In some embodiments, the pancreatic progenitor cells or precursors thereof are contacted with the WNT signaling inhibitor or the compound that inhibits expression or activity of Tankyrase for about 1, about 2, about 3, about 4, about 5, about 6, about 7, or about 8 days. In some embodiments, the composition further comprises an agent selected from the group consisting of: a transforming growth factor 3 (TGF-β) signaling pathway inhibitor, a thyroid hormone (TH) signaling pathway activator, at least one sonic-hedgehog (SHH) pathway inhibitor, a retinoic acid (RA) signaling pathway activator, a γ-secretase inhibitor, a bone morphogenic protein (BMP) signaling pathway inhibitor, an inhibitor of Rho-associated, coiled-coil containing protein kinase, at least one growth factor from epidermal growth factor (EGF) family, a broad kinase inhibitor, an histone deacetylase (HDAC) inhibitor, and any combinations thereof.

Another aspect of the present disclosure provides a method comprising: contacting a population of cells comprising pancreatic progenitor cells or precursors thereof with a composition comprising an epigenetic modifying compound, thereby differentiating the pancreatic progenitor cells or precursors thereof into pancreatic α cells.

In some embodiments, the contacting results in a second population of cells comprising a larger percentage of the pancreatic α cells as compared to a corresponding population of cells comprising the pancreatic α cells which is not contacted with the epigenetic modifying compound. In some embodiments, the epigenetic modifying compound inhibits bromodomain of Bromodomain and Extra-Terminal (BET) proteins. In some embodiments, the epigenetic modifying compounds comprises a HDAC inhibitor.

Another aspect of the present disclosure provides a method comprising: contacting a population of cells comprising pancreatic progenitor cells or precursors thereof with a composition comprising a compound that inhibits bromodomain of BET proteins, thereby differentiating the pancreatic progenitor cells or precursors thereof into pancreatic α cells.

In some embodiments, the contacting results in a second population of cells comprising a larger percentage of pancreatic α cells as compared to a corresponding population of cells comprising pancreatic α cells which is not contacted with the compound that inhibits bromodomain of Bromodomain and Extra-Terminal (BET) proteins. In some embodiments, the pancreatic α cells are NKX6.1 negative and ISL1 positive. In some embodiments, the pancreatic α cells express Arx, glucagon, or both. In some embodiments, the second population of cells comprises at least 10%, at least 15%, at least 18%, at least 20%, at least 25%, or at least 30% pancreatic α cells. In some embodiments, the second population of cells comprises at least 150%, at least 200%, at least 220%, at least 250%, at least 300%, at least 350%, at least 400%, or at least 450% more pancreatic α cells as compared to the corresponding population of cells which is not contacted with the epigenetic modifying compound, the compound that inhibits bromodomain of Bromodomain and Extra-Terminal (BET) proteins, or the HDAC inhibitor. In some embodiments, the epigenetic modifying compound comprises an agent selected from the group consisting of: (+)-JQ1, I-BET151 (GSK1210151A), PFI-1 (PF-6405761), I-BET-762, Apabetalone (RVX-208), SGC-CBP30, bromosporine, UNC1215, OTX015, UNC669, BI-7273, CPI-637, CPI-0610, CPI-203, MS436, PFI-4, GSK2801, SF2523, PFI-3, Mivebresib(ABBV-075), GSK6853, EED226, PF-CBP1 HCl, AZD5153, I-BRD9, GSK1324726A (I-BET726), I-BET-762GSK525762, BI-9564, OF-1, and any combination thereof. In some embodiments, the epigenetic modifying compound comprises an agent selected from the group consisting of: Vorinostat (SAHA, MK0683), Entinostat (MS-275), Panobinostat (LBH589), Trichostatin A (TSA), Mocetinostat (MGCD0103), Biphenyl-4-sulfonyl chloride, WT161, Valproic acid, ACY-738, Tucidinostat (Chidamide), Belinostat (PXD101), Romidepsin (FK228, Depsipeptide), MC1568, Tubastatin A HCl, Givinostat (ITF2357), Dacinostat (LAQ824), CUDC-101, Quisinostat (JNJ-26481585) 2HCl, Pracinostat (SB939), PCI-34051, Droxinostat, Abexinostat (PCI-24781), RGFP966, AR-42, Ricolinostat (ACY-1215), Valproic acid sodium salt (Sodium valproate), Tacedinaline (CI994), CUDC-907, Sodium butyrate, Curcumin, M344, Tubacin, RG2833 (RGFP109), Resminostat, Divalproex Sodium, Scriptaid, Sodium Phenylbutyrate, Tubastatin A, TMP269, Santacruzamate A (CAY10683), TMP195, Tasquinimod, BRD73954, Citarinostat (ACY-241), Splitomicin, HPOB, LMK-235, Nexturastat A, ITSA-1 (ITSA1), (−)-Parthenolide, CAY10603, 4SC-202, BG45, and any combination thereof.

In some embodiments, aid pancreatic progenitor cells or precursors thereof are contacted with between 0.01 and 500 µM of the epigenetic modifying compound, the compound that inhibits bromodomain of Bromodomain and Extra-Terminal (BET) proteins, or the HDAC inhibitor. In some embodiments, the pancreatic progenitor cells or precursors thereof are contacted with between 0.1 and 100 µM of the epigenetic modifying compound, the compound that inhibits bromodomain of Bromodomain and Extra-Terminal (BET) proteins, or the HDAC inhibitor. In some embodiments, the pancreatic progenitor cells or precursors thereof are contacted with about 1, about 5, about 10 µM of the epigenetic modifying compound, the compound that inhibits bromodomain of Bromodomain and Extra-Terminal (BET) proteins, or the HDAC inhibitor. In some embodiments, the pancreatic progenitor cells or precursors thereof are contacted with the epigenetic modifying compound, the compound that inhibits bromodomain of Bromodomain and Extra-Terminal (BET) proteins, or the HDAC inhibitor for at least 1, at least 2, at least 3, at least 4, at least 5, at least 6, at least 7, at least 8 days. In some embodiments, the pancreatic progenitor cells or precursors thereof are contacted with the epigenetic modifying compound, the compound that inhibits bromodomain of Bromodomain and Extra-Terminal (BET) proteins, or the HDAC inhibitor for about 1, about 2, about 3, about 4, about 5, about 6, about 7, about 8 days. In some embodiments, the composition further comprises an agent selected from the group consisting of: a transforming growth factor β (TGF-β) signaling pathway inhibitor, a thyroid hormone (TH) signaling pathway activator, at least one sonic-hedgehog (SHH) pathway inhibitor, a retinoic acid (RA) signaling pathway activator, a γ-secretase inhibitor, a bone morphogenic protein (BMP) signaling pathway inhibitor, an inhibitor of Rho-associated, coiled-coil containing protein kinase, at least one growth factor from epidermal growth factor (EGF) family, a broad kinase inhibitor, an histone deacetylase (HDAC) inhibitor, and any combination thereof. In some embodiments, the pancreatic progenitor cells are PDX1 and NKX6.1 double positive. In some embodiments, the pancreatic progenitor cells are negative for ISL1, Chromogranin A, C-peptide, insulin, glucagon, Arx, any combination thereof. In some embodiments, the pancreatic progenitor cells or precursors thereof are derived from embryonic stem cells or pluripotent stem cells. In some embodiments, the pancreatic progenitor cells are derived from induced pluripotent stem cells.

Another aspect of the present disclosure provides a method comprising: differentiating a plurality of stem cells in vitro to obtain a cell population comprising pancreatic progenitor cells or precursors thereof, contacting in vitro the cell population with a composition comprising an agent selected from the group consisting of: a WNT signaling inhibitor, a compound that inhibits expression or activity of Tankyrase, an epigenetic modifying compound, a compound that inhibits bromodomain of Bromodomain and Extra-Terminal (BET) proteins, a HDAC inhibitor, and any combination thereof, thereby generating at least one endocrine cell; and maturing the at least one endocrine cell in vitro to obtain a population of cells comprising pancreatic α cells, pancreatic β cells, or both.

Another aspect of the present disclosure provides a composition comprising a population of cells generated according to the method as disclosed herein.

Another aspect of the present disclosure provides a composition comprising a pancreatic β cell, and a WNT signaling inhibitor.

Another aspect of the present disclosure provides a composition comprising a pancreatic β cell, and a compound that inhibits expression or activity of Tankyrase.

In some embodiments, the pancreatic β cell is NKX6.1 and ISL1 double-positive.

Another aspect of the present disclosure provides a composition comprising a pancreatic α cell, and an epigenetic modifying compound.

In some embodiments, the epigenetic compound inhibits bromodomain of Bromodomain and Extra-Terminal (BET) proteins. In some embodiments, the epigenetic compound comprises a HDAC inhibitor. In some embodiments, the pancreatic α cell is NKX6.1 negative and ISL1 positive. In some embodiments, the pancreatic α cell expresses Arx, Glucagon, or both.

Another aspect of the present disclosure provides a composition comprising a pancreatic progenitor cell or a precursor thereof, and a compound that inhibits bromodomain of Bromodomain and Extra-Terminal (BET) proteins.

Another aspect of the present disclosure provides a composition comprising a pancreatic progenitor cell or a precursor thereof, and a WNT signaling inhibitor.

Another aspect of the present disclosure provides a composition comprising a pancreatic progenitor cell or a precursor thereof, and a compound that inhibits expression or activity of Tankyrase.

Another aspect of the present disclosure provides a composition comprising a pancreatic progenitor cell or a precursor thereof, and an epigenetic modifying compound. In some embodiments, the epigenetic compound inhibits bromodomain of Bromodomain and Extra-Terminal (BET) proteins. In some embodiments, the epigenetic compound comprises a HDAC inhibitor.

Another aspect of the present disclosure provides a composition comprising a pancreatic progenitor cell or a precursor thereof, and a compound that inhibits bromodomain of Bromodomain and Extra-Terminal (BET) proteins.

Another aspect of the present disclosure provides a method of treating a subject in need thereof, comprising administering a composition comprising a population of cells generated according to the method as disclosed herein.

Another aspect of the present disclosure provides a device comprising a population of cells generated according to the method as disclosed herein.

Provided herein are methods comprising: differentiating at least a portion of a population of posterior foregut associated cells into a population of Pdx1 expressing, NKX6.1 expressing pancreatic progenitor cells by contacting said population of posterior foregut associated cells in vitro with a composition that comprises a WNT signaling inhibitor or a protein kinase C (PKC) activator, or both.

In some embodiments, said posterior foregut associated cells express Pdx1. In some embodiments, said posterior foregut associated cells do not express NKX6.1.

In some embodiments, said method further comprises differentiating at least a portion of said population of Pdx1 expressing, NKX6.1 expressing pancreatic progenitor cells into a population of pancreatic endocrine progenitor cells in vitro.

In some embodiments, said composition comprises a WNT signaling inhibitor.

In some embodiments, said population of pancreatic endocrine progenitor cells comprises a higher percentage of in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 30%, 35%, 40%, 45%, 50%, 55%, 60%, 65%, 70%, 75%, 80%, or 90% in vitro differentiated NKX6.1 expressing, ISL1 expressing β cells, wherein said percentage of said in vitro differentiated NKX6.1 expressing, ISL1 expressing β cells is determined prior to performance of an optional selection step. In some embodiments, said population of pancreatic endocrine progenitor cells comprises a lower percentage of in vitro differentiated cells that express neither NKX6.1 nor ISL1, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated cells that express neither NKX6.1 nor ISL1, relative to a comparable population of pancreatic endocrine progenitor cells produced by a method in which said population of Pdx1-expressing pancreatic progenitor cells are not contacted in vitro with a WNT signaling inhibitor. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated cells that express neither NKX6.1 nor ISL1, wherein said percentage of said in vitro differentiated cells that express neither NKX6.1 nor ISL1 is determined prior to performance of an optional selection step.

In some embodiments, said composition comprises a PKC activator. In some embodiments, said composition comprises a PKC activator. In some embodiments, said population of pancreatic endocrine progenitor cells comprises a higher percentage of in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated NKX6.1 non-expressing, ISL1 expressing α cells, wherein said percentage of said in vitro differentiated NKX6.1 non-expressing, ISL1 expressing α cells is determined prior to performance of an optional selection step. In some embodiments, said population of pancreatic endocrine progenitor cells comprises a higher percentage of in vitro differentiated glucagon expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated glucagon expressing α cells, relative to a comparable population of pancreatic endocrine progenitor cells produced by a method in which said population of Pdx1-expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated glucagon expressing α cells, wherein said percentage of said in vitro differentiated glucagon expressing α cells is determined prior to performance of an optional selection step. In some embodiments, said population of pancreatic endocrine progenitor cells comprises a higher percentage of in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated ARX expressing α cells, wherein said percentage of said in vitro differentiated ARX expressing α cells is determined prior to performance of an optional selection step. In some embodiments, said population of pancreatic endocrine progenitor cells comprises a lower percentage of in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated VMAT1 expressing enterochromaffin cells, wherein said percentage of said in vitro differentiated VMAT1 expressing enterochromaffin cells is determined prior to performance of an optional selection step.

In some embodiments, at least a portion of said population of pancreatic endocrine progenitor cells are matured in vitro into β cells that exhibit glucose stimulated insulin secretion (GSIS) in vitro.

Provided herein are methods comprising: differentiating a plurality of stem cells in vitro to obtain a cell population that comprises a population of pancreatic endocrine progenitor cells, wherein said differentiation comprises contacting a population of cells differentiated in vitro from said plurality of stem cells with a composition that comprises a Wnt signaling inhibitor, a PKC activator, or both, to produce said population of pancreatic endocrine cells, wherein said population of pancreatic endocrine cells comprises at least 40% NKX6.1 expressing, ISL1 expressing β cells and at least 20% NKX6.1 non-expressing, ISL1 expressing α cells.

In some embodiments, said population of pancreatic endocrine cells comprises at least one, two, three, four, or five of: less than 20% VMAT expressing EC cells, less than 20% CDX2 expressing EC cells, less than 15% NKX6.1 non-expressing, ISL1 non-expressing cells, at least 20% glucagon expressing α cells, at least 20% ARX expressing α cells.

In some embodiments, said composition comprises a WNT signaling inhibitor.

In some embodiments, said population of pancreatic endocrine progenitor cells comprises a higher percentage of in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 30%, 35%, 40%, 45%, 50%, 55%, 60%, 65%, 70%, 75%, 80%, or 90% in vitro differentiated NKX6.1 expressing, ISL1 expressing β cells, wherein said percentage of said in vitro differentiated NKX6.1 expressing, ISL1 expressing β cells is determined prior to performance of an optional selection step. In some embodiments, said population of pancreatic endocrine progenitor cells comprises a lower percentage of in vitro differentiated cells that express neither NKX6.1 nor ISL1, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated cells that express neither NKX6.1 nor ISL1, relative to a comparable population of pancreatic endocrine progenitor cells produced by a method in which said population of Pdx1-expressing pancreatic progenitor cells are not contacted in vitro with a WNT signaling inhibitor. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated cells that express neither NKX6.1 nor ISL1, wherein said percentage of said in vitro differentiated cells that express neither NKX6.1 nor ISL1 is determined prior to performance of an optional selection step.

In some embodiments, said composition comprises a PKC activator. In some embodiments, said composition comprises a PKC activator. In some embodiments, said population of pancreatic endocrine progenitor cells comprises a higher percentage of in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated NKX6.1 non-expressing, ISL1 expressing α cells, wherein said percentage of said in vitro differentiated NKX6.1 non-expressing, ISL1 expressing α cells is determined prior to performance of an optional selection step. In some embodiments, said population of pancreatic endocrine progenitor cells comprises a higher percentage of in vitro differentiated glucagon expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated glucagon expressing α cells, relative to a comparable population of pancreatic endocrine progenitor cells produced by a method in which said population of Pdx1-expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated glucagon expressing α cells, wherein said percentage of said in vitro differentiated glucagon expressing α cells is determined prior to performance of an optional selection step. In some embodiments, said population of pancreatic endocrine progenitor cells comprises a higher percentage of in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated ARX expressing α cells, wherein said percentage of said in vitro differentiated ARX expressing α cells is determined prior to performance of an optional selection step. In some embodiments, said population of pancreatic endocrine progenitor cells comprises a lower percentage of in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated VMAT1 expressing enterochromaffin cells, wherein said percentage of said in vitro differentiated VMAT1 expressing enterochromaffin cells is determined prior to performance of an optional selection step.

In some embodiments, at least a portion of said population of pancreatic endocrine progenitor cells are matured in vitro into β cells that exhibit glucose stimulated insulin secretion (GSIS) in vitro.

Provided herein are methods comprising: differentiating a plurality of stem cells in vitro to obtain a cell population that comprises a population of pancreatic endocrine progenitor cells, wherein said differentiation comprises contacting a population of cells differentiated in vitro from said plurality of stem cells with a Wnt signaling inhibitor, a PKC activator, or both, to produce said population of pancreatic endocrine cells, wherein said population of pancreatic endocrine cells comprises at least 40% NKX6.1 expressing, ISL1 expressing β cells and less than 15% NKX6.1 non-expressing, ISL1 non-expressing cells.

In some embodiments, said composition comprises a WNT signaling inhibitor. In some embodiments, said population of pancreatic endocrine progenitor cells comprises a higher percentage of in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 30%, 35%, 40%, 45%, 50%, 55%, 60%, 65%, 70%, 75%, 80%, or 90% in vitro differentiated NKX6.1 expressing, ISL1 expressing β cells, wherein said percentage of said in vitro differentiated NKX6.1 expressing, ISL1 expressing β cells is determined prior to performance of an optional selection step. In some embodiments, said population of pancreatic endocrine progenitor cells comprises a lower percentage of in vitro differentiated cells that express neither NKX6.1 nor ISL1, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated cells that express neither NKX6.1 nor ISL1, relative to a comparable population of pancreatic endocrine progenitor cells produced by a method in which said population of Pdx1-expressing pancreatic progenitor cells are not contacted in vitro with a WNT signaling inhibitor. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated cells that express neither NKX6.1 nor ISL1, wherein said percentage of said in vitro differentiated cells that express neither NKX6.1 nor ISL1 is determined prior to performance of an optional selection step.

In some embodiments, said composition comprises a PKC activator. In some embodiments, said composition comprises a PKC activator. In some embodiments, said population of pancreatic endocrine progenitor cells comprises a higher percentage of in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated NKX6.1 non-expressing, ISL1 expressing α cells, wherein said percentage of said in vitro differentiated NKX6.1 non-expressing, ISL1 expressing α cells is determined prior to performance of an optional selection step. In some embodiments, said population of pancreatic endocrine progenitor cells comprises a higher percentage of in vitro differentiated glucagon expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated glucagon expressing α cells, relative to a comparable population of pancreatic endocrine progenitor cells produced by a method in which said population of Pdx1-expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated glucagon expressing α cells, wherein said percentage of said in vitro differentiated glucagon expressing α cells is determined prior to performance of an optional selection step. In some embodiments, said population of pancreatic endocrine progenitor cells comprises a higher percentage of in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated ARX expressing α cells, wherein said percentage of said in vitro differentiated ARX expressing α cells is determined prior to performance of an optional selection step. In some embodiments, said population of pancreatic endocrine progenitor cells comprises a lower percentage of in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated VMAT1 expressing enterochromaffin cells, wherein said percentage of said in vitro differentiated VMAT1 expressing enterochromaffin cells is determined prior to performance of an optional selection step.

In some embodiments, at least a portion of said population of pancreatic endocrine progenitor cells are matured in vitro into β cells that exhibit glucose stimulated insulin secretion (GSIS) in vitro.

Provided herein are methods comprising: differentiating a plurality of stem cells in vitro to obtain a cell population that comprises a population of pancreatic endocrine progenitor cells, wherein said differentiation comprises contacting a population of cells differentiated in vitro from said plurality of stem cells with a Wnt signaling inhibitor, a PKC activator, or both, to produce said population of pancreatic endocrine cells, wherein said population of pancreatic endocrine cells comprises at least 20% (e.g., at least 25%, 30%, 35%, 40%) NKX6.1 non-expressing, ISL1 expressing α cells, and less than 20% (e.g., less than 15%, 10%, 5%, 1%) VMAT expressing EC cells.

In some embodiments, said population of pancreatic endocrine cells comprises at least one, two, or three of: less than 20% (e.g., less than 15%, 10%, 5%, 1%) CDX2 expressing EC cells, at least 20% glucagon expressing α cells (e.g., at least 25%, 30%, 35%, 40%), or at least 20% ARX expressing α cells (e.g., at least 25%, 30%, 35%, 40%).

In some embodiments, said method further comprises differentiating said NKX6.1 expressing, ISL1 expressing β cells into mature β cells that exhibit glucose stimulated insulin secretion (GSIS) in vitro.

In some embodiments, said composition comprises a WNT signaling inhibitor. In some embodiments, said population of pancreatic endocrine progenitor cells comprises a higher percentage of in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 expressing, ISL1 expressing β cells, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 30%, 35%, 40%, 45%, 50%, 55%, 60%, 65%, 70%, 75%, 80%, or 90% in vitro differentiated NKX6.1 expressing, ISL1 expressing β cells, wherein said percentage of said in vitro differentiated NKX6.1 expressing, ISL1 expressing β cells is determined prior to performance of an optional selection step. In some embodiments, said population of pancreatic endocrine progenitor cells comprises a lower percentage of in vitro differentiated cells that express neither NKX6.1 nor ISL1, relative to a comparable population of pancreatic endocrine progenitor cells produced by a method in which said population of Pdx1 expressing pancreatic progenitor cells are not contacted in vitro with a WNT signaling inhibitor. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated cells that express neither NKX6.1 nor ISL1, relative to a comparable population of pancreatic endocrine progenitor cells produced by a method in which said population of Pdx1-expressing pancreatic progenitor cells are not contacted in vitro with a WNT signaling inhibitor. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated cells that express neither NKX6.1 nor ISL1, wherein said percentage of said in vitro differentiated cells that express neither NKX6.1 nor ISL1 is determined prior to performance of an optional selection step.

In some embodiments, said composition comprises a PKC activator. In some embodiments, said composition comprises a PKC activator. In some embodiments, said population of pancreatic endocrine progenitor cells comprises a higher percentage of in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated NKX6.1 non expressing, ISL1 expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated NKX6.1 non-expressing, ISL1 expressing α cells, wherein said percentage of said in vitro differentiated NKX6.1 non-expressing, ISL1 expressing α cells is determined prior to performance of an optional selection step. In some embodiments, said population of pancreatic endocrine progenitor cells comprises a higher percentage of in vitro differentiated glucagon expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated glucagon expressing α cells, relative to a comparable population of pancreatic endocrine progenitor cells produced by a method in which said population of Pdx1-expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated glucagon expressing α cells, wherein said percentage of said in vitro differentiated glucagon expressing α cells is determined prior to performance of an optional selection step. In some embodiments, said population of pancreatic endocrine progenitor cells comprises a higher percentage of in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% more in vitro differentiated ARX expressing α cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 10%, 15%, 20%, 25%, 30%, 35%, 40%, 45%, 50%, 55%, or 60% in vitro differentiated ARX expressing α cells, wherein said percentage of said in vitro differentiated ARX expressing α cells is determined prior to performance of an optional selection step. In some embodiments, said population of pancreatic endocrine progenitor cells comprises a lower percentage of in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises at least 1%, 2%, 3%, 4%, 5%, 6%, 7%, 8%, 9%, 10%, 15%, 20%, 25%, 30%, 35%, 40%, 45%, 50%, 55%, 60%, 70%, 80%, 90%, 100%, 150%, 200%, 250%, or 300% less in vitro differentiated VMAT1 expressing enterochromaffin cells, relative to a comparable population of pancreatic endocrine progenitor cells produced by a method in which said population of Pdx1 expressing pancreatic progenitor cells are not contacted in vitro with a PKC activator. In some embodiments, said population of pancreatic endocrine progenitor cells comprises less than 40%, 30%, 25%, 20%, 15%, 10%, 9%, 8%, 7%, 6%, 5%, 4%, 3%, 2% or 1% of in vitro differentiated VMAT1 expressing enterochromaffin cells, wherein said percentage of said in vitro differentiated VMAT1 expressing enterochromaffin cells is determined prior to performance of an optional selection step.

In some embodiments, at least a portion of said population of pancreatic endocrine progenitor cells are matured in vitro into β cells that exhibit glucose stimulated insulin secretion (GSIS) in vitro.

Provided herein are populations of in vitro differentiated pancreatic progenitor cells that comprises at least 40% NKX6.1 expressing, ISL1 expressing β cells (e.g., at least 45%, 50%, 60%, 65%, 70%, 75%, 80%, 90%, 95%), at least 20% NKX6.1 non-expressing, ISL1 expressing α cells (e.g., at least 25%, 30%, 35%, 40%), less than 20% VMAT expressing EC cells (e.g., less than 15%, 10%, 5%, 1%), less than 20% CDX2 expressing EC cells (e.g., less than 15%, 10%, 5%, 1%), less than 15% NKX6.1 non-expressing, ISL1 non-expressing cells (e.g., less than 10%, 5%, 1%), at least 20% glucagon expressing α cells (e.g., at least 25%, 30%, 35%, 40%), at least 20% ARX expressing α cells (e.g., at least 25%, 30%, 35%, 40%).

Provided herein are devices comprising a population of in vitro differentiated pancreatic progenitor cells that comprises at least 40% (e.g., at least 45%, 50%, 60%, 65%, 70%, 75%, 80%, 90%, 95%) NKX6.1 expressing, ISL1 expressing β cells, at least 20% NKX6.1 non-expressing, ISL1 expressing α cells, less than 20% (e.g., less than 15%, 10%, 5%, 1%) VMAT expressing EC cells, less than 20% (e.g., less than 15%, 10%, 5%, 1%) CDX2 expressing EC cells, less than 15% (e.g., less than 10%, 5%, 1%) NKX6.1 non-expressing, ISL1 non-expressing cells, at least 20% (e.g., at least 25%, 30%, 35%, 40%) glucagon expressing α cells, at least 20% (e.g., at least 25%, 30%, 35%, 40%) ARX expressing α cells. In some embodiments, said device is configured for placement into a human subject.

Provided herein are methods comprising: contacting a population of cells comprising pancreatic progenitor cells or precursors thereof with a composition comprising an epigenetic modifying compound, thereby differentiating said pancreatic progenitor cells or precursors thereof into pancreatic α cells. In some embodiments, said contacting results in a second population of cells comprising a larger percentage of said pancreatic α cells as compared to a corresponding population of cells comprising said pancreatic α cells which is not contacted with said epigenetic modifying compound. In some embodiments, said epigenetic modifying compound inhibits bromodomain of Bromodomain and Extra-Terminal (BET) proteins. In some embodiments, said epigenetic modifying compounds comprises a HDAC inhibitor.

Provided herein are methods comprising: contacting a population of cells comprising pancreatic progenitor cells or precursors thereof with a composition comprising a compound that inhibits bromodomain of BET proteins, thereby differentiating said pancreatic progenitor cells or precursors thereof into pancreatic α cells.

In some embodiments, said contacting results in a second population of cells comprising a larger percentage of pancreatic α cells as compared to a corresponding population of cells comprising pancreatic α cells which is not contacted with said compound that inhibits bromodomain of Bromodomain and Extra-Terminal (BET) proteins. In some embodiments, said pancreatic α cells are NKX6.1 negative and ISL1 positive. In some embodiments, said pancreatic α cells express Arx, glucagon, or both. In some embodiments, said second population of cells comprises at least 10%, at least 15%, at least 18%, at least 20%, at least 25%, or at least 30% pancreatic α cells. In some embodiments, said second population of cells comprises at least 150%, at least 200%, at least 220%, at least 250%, at least 300%, at least 350%, at least 400%, or at least 450% more pancreatic α cells as compared to said corresponding population of cells which is not contacted with said epigenetic modifying compound, said compound that inhibits bromodomain of Bromodomain and Extra-Terminal (BET) proteins, or said HDAC inhibitor.

In some embodiments, said epigenetic modifying compound comprises an agent selected from the group consisting of: (+)-JQ1, I-BET151 (GSK1210151A), PFI-1 (PF-6405761), I-BET-762, Apabetalone (RVX-208), SGC-CBP30, bromosporine, UNC1215, OTX015, UNC669, BI-7273, CPI-637, CPI-0610, CPI-203, MS436, PFI-4, GSK2801, SF2523, PFI-3, Mivebresib(ABBV-075), GSK6853, EED226, PF-CBP1 HCl, AZD5153, I-BRD9, GSK1324726A (I-BET726), I-BET-762GSK525762, BI-9564, OF-1, and any combination thereof.

In some embodiments, said epigenetic modifying compound comprises an agent selected from the group consisting of: Vorinostat (SAHA, MK0683), Entinostat (MS-275), Panobinostat (LBH589), Trichostatin A (TSA), Mocetinostat (MGCD0103), Biphenyl-4-sulfonyl chloride, WT161, Valproic acid, ACY-738, Tucidinostat (Chidamide), Belinostat (PXD101), Romidepsin (FK228, Depsipeptide), MC1568, Tubastatin A HCl, Givinostat (ITF2357), Dacinostat (LAQ824), CUDC-101, Quisinostat (JNJ-26481585) 2HCl, Pracinostat (SB939), PCI-34051, Droxinostat, Abexinostat (PCI-24781), RGFP966, AR-42, Ricolinostat (ACY-1215), Valproic acid sodium salt (Sodium valproate), Tacedinaline (CI994), CUDC-907, Sodium butyrate, Curcumin, M344, Tubacin, RG2833 (RGFP109), Resminostat, Divalproex Sodium, Scriptaid, Sodium Phenylbutyrate, Tubastatin A, TMP269, Santacruzamate A (CAY10683), TMP195, Tasquinimod, BRD73954, Citarinostat (ACY-241), Splitomicin, HPOB, LMK-235, Nexturastat A, ITSA-1 (ITSA1), (−)-Parthenolide, CAY10603, 4SC-202, BG45, and any combination thereof.

In some embodiments, said pancreatic progenitor cells or precursors thereof are contacted with between 0.01 and 500 μM of said epigenetic modifying compound, said compound that inhibits bromodomain of Bromodomain and Extra-Terminal (BET) proteins, or said HDAC inhibitor. In some embodiments, said pancreatic progenitor cells or precursors thereof are contacted with between 0.1 and 100 μM of said epigenetic modifying compound, said compound that inhibits bromodomain of Bromodomain and Extra-Terminal (BET) proteins, or said HDAC inhibitor. In some embodiments, said pancreatic progenitor cells or precursors thereof are contacted with about 1, about 5, about 10 μM of said epigenetic modifying compound, said compound that inhibits bromodomain of Bromodomain and Extra-Terminal (BET) proteins, or said HDAC inhibitor.

In some embodiments, said pancreatic progenitor cells or precursors thereof are contacted with said epigenetic modifying compound, said compound that inhibits bromodomain of Bromodomain and Extra-Terminal (BET) proteins, or said HDAC inhibitor for at least 1, at least 2, at least 3, at least 4, at least 5, at least 6, at least 7, at least 8 days. In some embodiments, said pancreatic progenitor cells or precursors thereof are contacted with said epigenetic modifying compound, said compound that inhibits bromodomain of Bromodomain and Extra-Terminal (BET) proteins, or said HDAC inhibitor for about 1, about 2, about 3, about 4, about 5, about 6, about 7, about 8 days.

In some embodiments, said composition further comprises an agent selected from the group consisting of: a transforming growth factor β (TGF-β) signaling pathway inhibitor, a thyroid hormone (TH) signaling pathway activator, at least one sonic-hedgehog (SHH) pathway inhibitor, a retinoic acid (RA) signaling pathway activator, a γ-secretase inhibitor, a bone morphogenic protein (BMP) signaling pathway inhibitor, an inhibitor of Rho-associated, coiled-coil containing protein kinase, at least one growth factor from epidermal growth factor (EGF) family, a broad kinase inhibitor, an histone deacetylase (HDAC) inhibitor, and any combination thereof.

In some embodiments, said pancreatic progenitor cells are PDX1 and NKX6.1 double positive. In some embodiments, said pancreatic progenitor cells are negative for ISL1, Chromogranin A, C-peptide, insulin, glucagon, Arx, any combination thereof. In some embodiments, said pancreatic progenitor cells or precursors thereof are derived from embryonic stem cells or pluripotent stem cells. In some embodiments, said pancreatic progenitor cells are derived from induced pluripotent stem cells.

Provided herein are methods comprising: differentiating a plurality of stem cells in vitro to obtain a cell population comprising pancreatic progenitor cells or precursors thereof; contacting in vitro said cell population with a composition comprising an agent selected from the group consisting of: a WNT signaling inhibitor, a compound that inhibits expression or activity of Tankyrase, an epigenetic modifying compound, a compound that inhibits bromodomain of Bromodomain and Extra-Terminal (BET) proteins, a HDAC inhibitor, and any combination thereof, thereby generating at least one endocrine cell; and maturing said at least one endocrine cell in vitro to obtain a population of cells comprising pancreatic α cells, pancreatic β cells, or both.

Provided herein are compositions comprising a population of cells generated according to a method described herein. Provided herein are compositions comprising a pancreatic β cell, and a WNT signaling inhibitor. Provided herein are compositions comprising a pancreatic β cell, and a compound that inhibits expression or activity of Tankyrase. In some embodiments, said pancreatic β cell is NKX6.1 and ISL1 double-positive.

Provided herein are compositions comprising a pancreatic α cell, and an epigenetic modifying compound. In some embodiments, said epigenetic compound inhibits bromodomain of Bromodomain and Extra-Terminal (BET) proteins. In some embodiments, said epigenetic compound comprises a HDAC inhibitor. In some embodiments, said pancreatic α cell is NKX6.1 negative and ISL1 positive. In some embodiments, said pancreatic α cell expresses Arx, Glucagon, or both.

Provided herein are compositions comprising a pancreatic progenitor cell or a precursor thereof, and a compound that inhibits bromodomain of Bromodomain and Extra-Terminal (BET) proteins. Provided herein are compositions comprising a pancreatic progenitor cell or a precursor thereof, and a WNT signaling inhibitor. Provided herein are compositions comprising a pancreatic progenitor cell or a precursor thereof, and a compound that inhibits expression or activity of Tankyrase. Provided herein are compositions comprising a pancreatic progenitor cell or a precursor thereof, and an epigenetic modifying compound. In some embodiments, said epigenetic compound inhibits bromodomain of Bromodomain and Extra-Terminal (BET) proteins. In some embodiments, said epigenetic compound comprises a HDAC inhibitor.

Provided herein are compositions comprising a pancreatic progenitor cell or a precursor thereof, and a compound that inhibits bromodomain of Bromodomain and Extra-Terminal (BET) proteins.

Provided herein are methods of treating a subject in need thereof, comprising administering a composition comprising a population of cells generated according to a method described herein. Provided herein are devices comprising a population of cells generated according to a method described herein. Provided herein are composition that comprises population of cells produced by a method described herein. Provided herein are devices that comprises a population of cells produced by a method described herein. Provided herein are devices that comprises cell compositions described herein. Provided herein are methods of treating a human subject with a disease characterized by high blood sugar levels over a prolonged period of time, the method comprising administering said subject a composition described herein. Provided herein are methods of treating a subject with a disease characterized by high blood sugar levels over a prolonged period of time, the method comprising implanting a device described herein into said subject.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2 shows an exemplary readout method for identifying agents that modulate differentiation of stem cells into pancreatic endocrine cells, where expression of cell markers like NKX6.1 and ISL1 are examined by high-throughput cell sorting techniques. Shown on the right are exemplary images of expression of NKX6.1 and ISL1 in exemplary cell populations.

FIG. 4 is a chart of exemplary compounds according to the present disclosure and their effects on differentiation of stem cells into pancreatic endocrine cells.

FIG. 25A shows a plot from a FACS analysis of the percentage of VMAT1 positive SC-EC cells at the end of stage 5 produced using a control stage 4 medium that did not contain a PKC activator. FIG. 25B shows a plot from a FACS analysis of the percentage of VMAT1 positive SC-EC cells at the end of stage 5 produced using a modified stage 4 medium that contained a PKC activator (0.5 μM PDBU (phorbol dibutyrate)). Inclusion of the PKC activator (0.5 μM PDBU (phorbol dibutyrate)) during stage 4 decreased the percentage of VMAT1 positive SC-EC cells at the end of stage 5.

S4d6, S4d3-S5d2, S4d5-S4d6, or S4d5-S5d62.

FIG. 38 shows a schematic depicting the exemplary stage 4 and stage 5 differentiation protocols utilizing a PKC activator and a TNKS/Wnt inhibitor, as described herein. For example, in some embodiments, a PKC activator is utilized during S4d5-S5d2 and the PKC activator is utilized during S4d5-S4d6.

DETAILED DESCRIPTION OF THE DISCLOSURE

Figure 1:
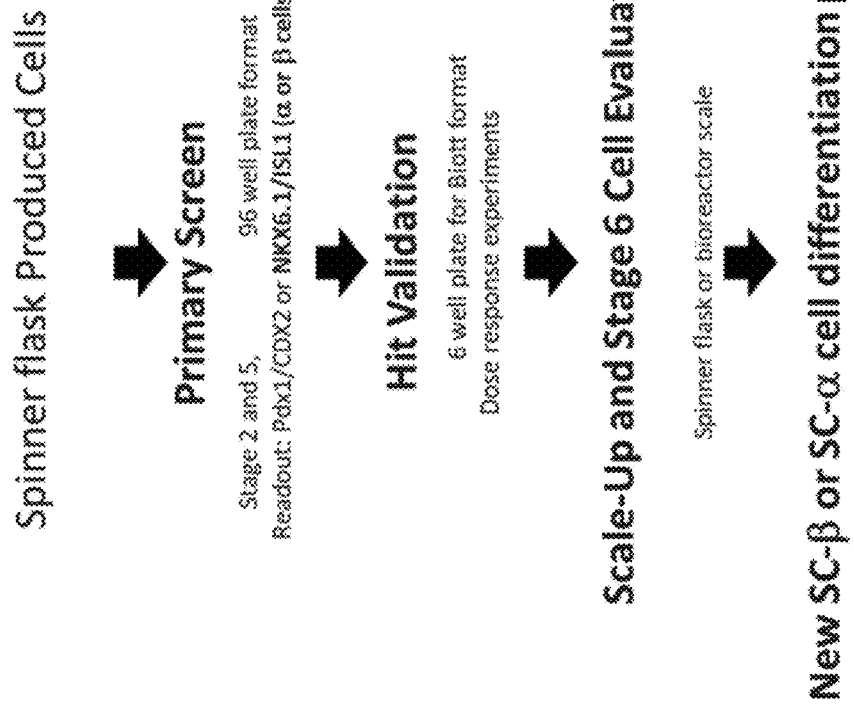
FIG. 1 illustrates an exemplary process for identifying agents that modulate differentiation of stem cells into pancreatic endocrine cells (e.g., pancreatic α or β cells), where various agents are incubated with Stage 4 (S4) cells during their Stage 5 (S5) differentiation into pancreatic endocrine cells.
Figure 3:
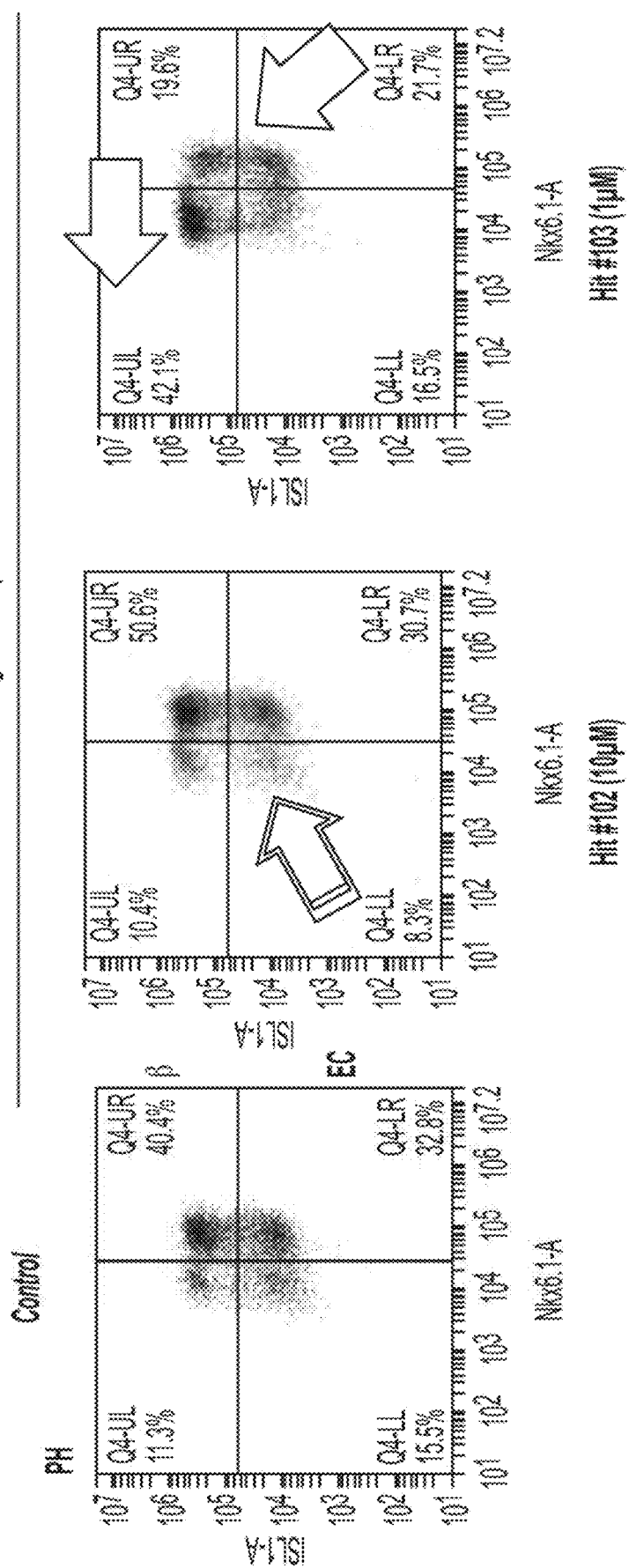
FIG. 3 shows cell sorting results demonstrating increase in SC-β cells or SC-α cells induced by incubation of exemplary compounds.
Figure 5:
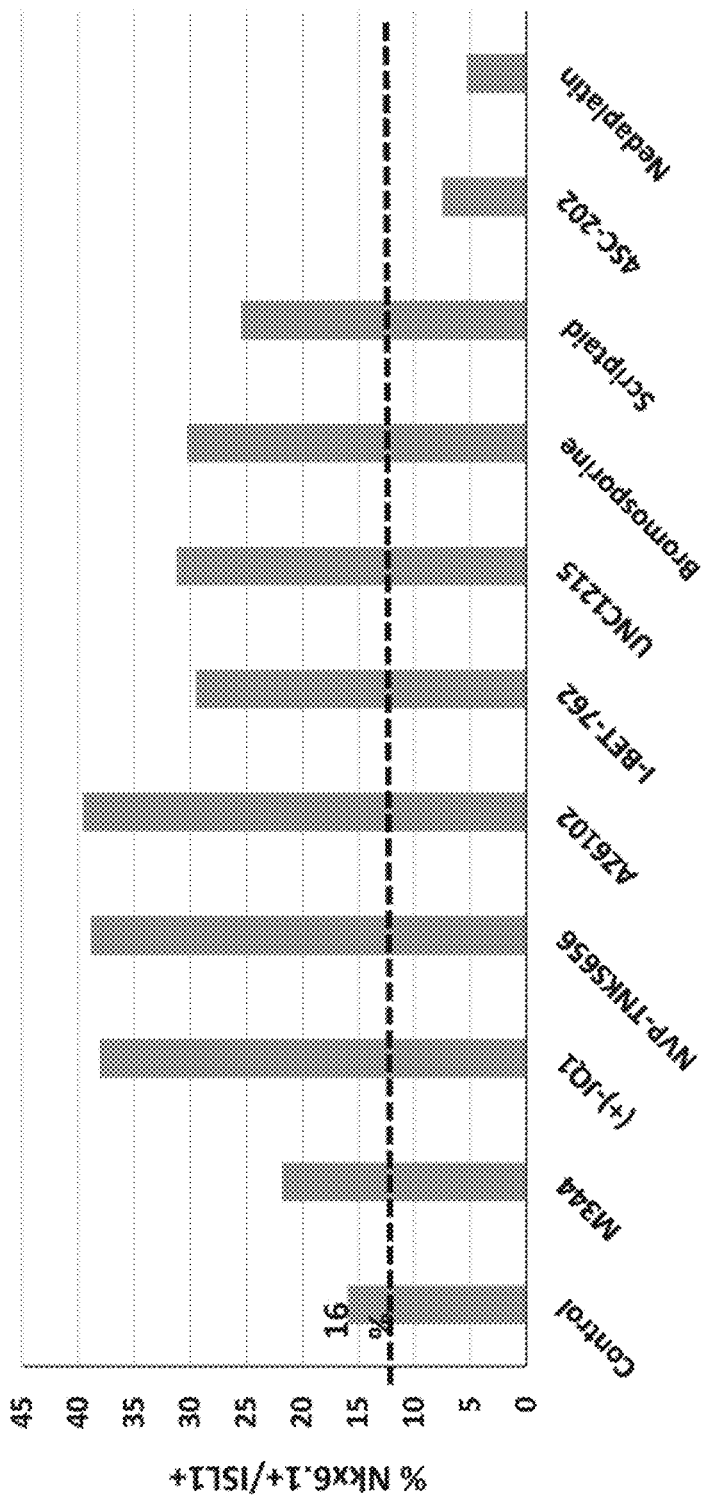
FIGS. 5-9 are graphs summarizing effects of a number of different exemplary compounds on percentage level of NKX6.1+/ISL1+ cells in S5 cell population.
Figure 6:
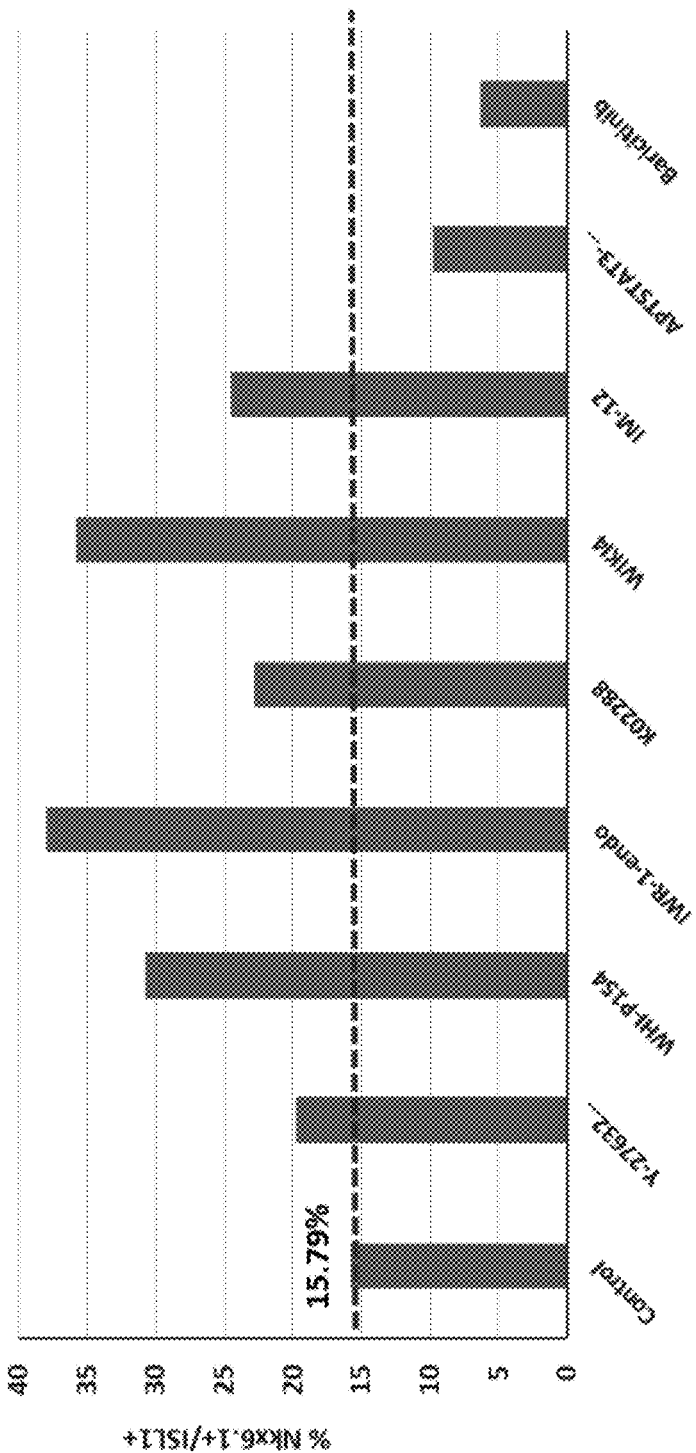
Figure 7:
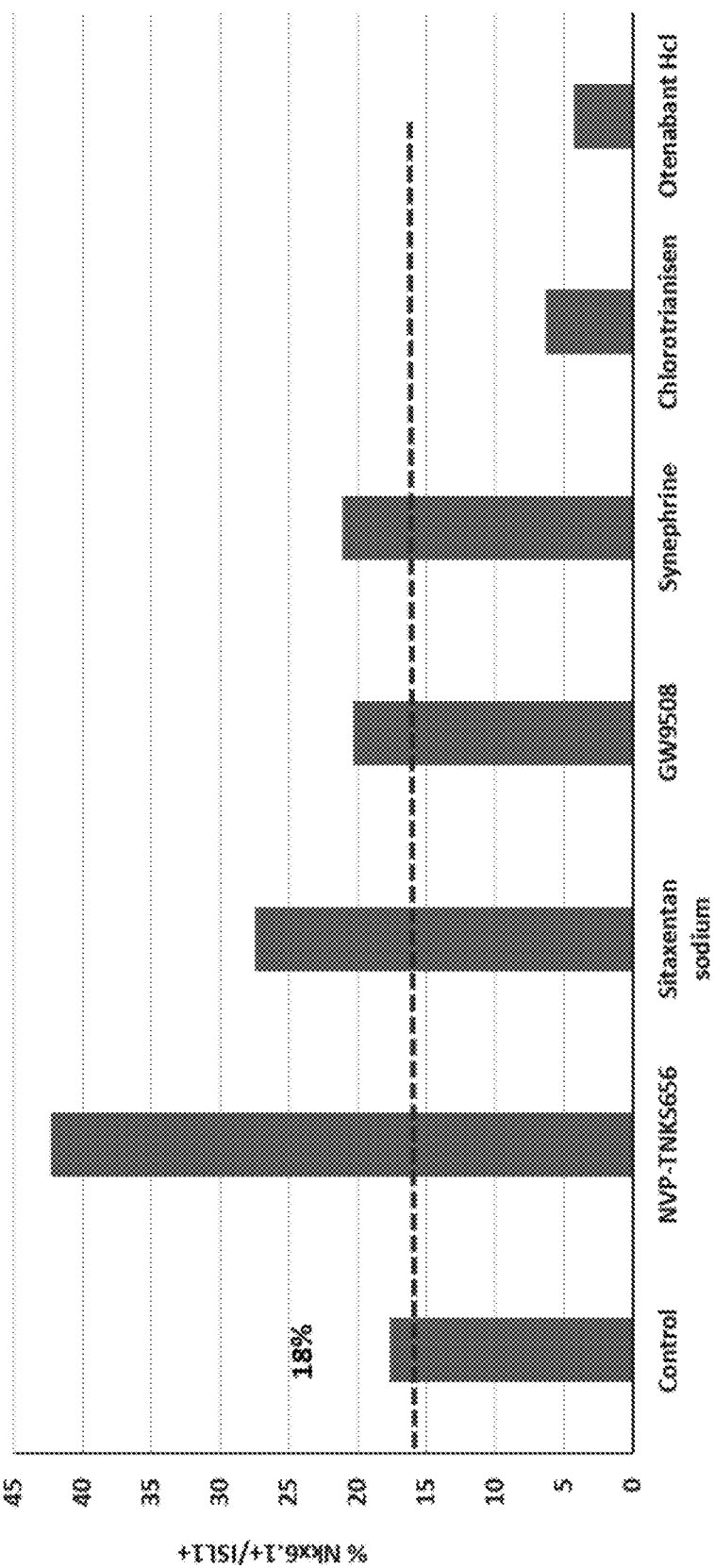
Figure 8:
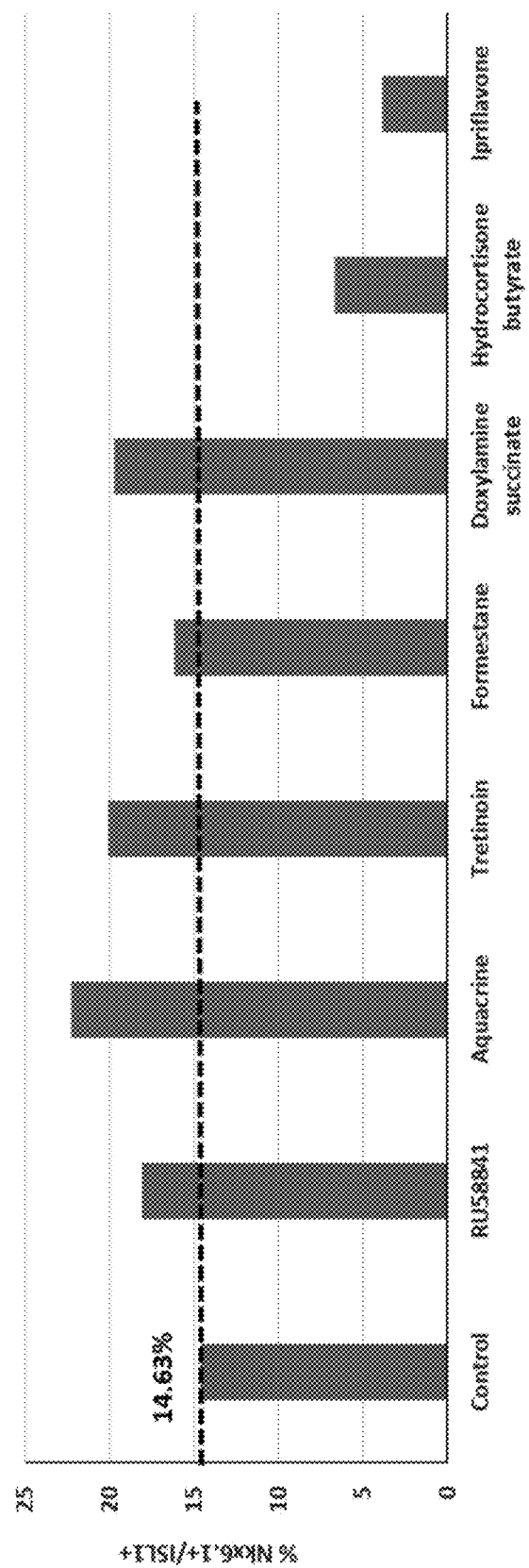
Figure 9:
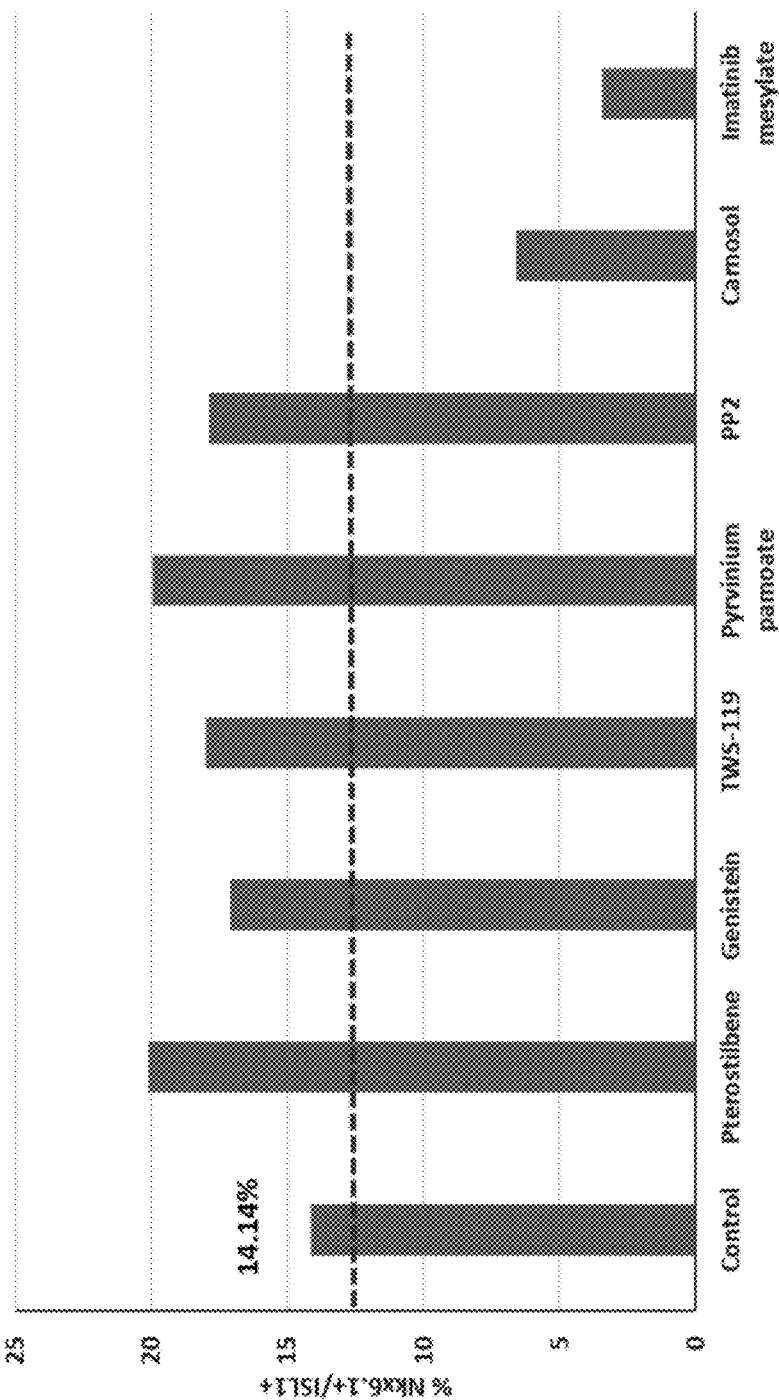
Figure 10:
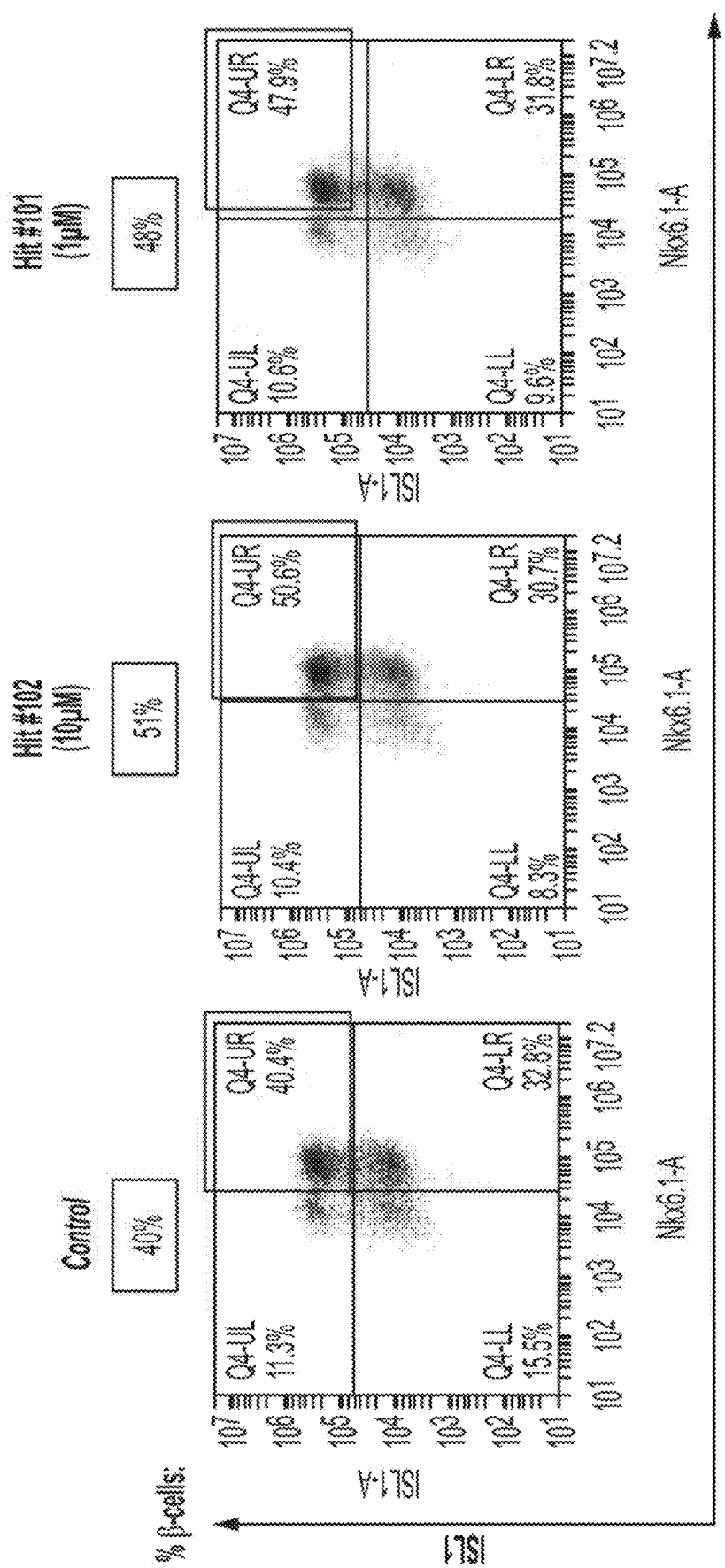
FIG. 10 shows cell sorting results demonstrating effects of two exemplary compounds on level of NKK6.1 and ISL1 expression in a S5 cell population.

The following description and examples illustrate embodiments of the present disclosure in detail. It is to be understood that this disclosure is not limited to the particular embodiments described herein and as such can vary. Those of skill in the art will recognize that there are numerous variations and modifications of this disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the present disclosure can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only and is not intended to be limiting.

Definitions

In this application, the use of the singular includes the plural unless specifically stated otherwise. It must be noted that, as used in the specification, the singular forms "a," "an" and "the" include plural referents unless the context clearly dictates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

Furthermore, use of the term "including" as well as other forms, such as "include", "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "diabetes" and its grammatical equivalents as used herein can refer to is a disease characterized by high blood sugar levels over a prolonged period. For example, the term "diabetes" and its grammatical equivalents as used herein can refer to all or any type of diabetes, including, but not limited to, type 1, type 2, cystic fibrosis-related, surgical, gestational diabetes, and mitochondrial diabetes. In some cases, diabetes can be a form of hereditary diabetes.

The term "progenitor" or "precursor" cell are used interchangeably herein and refer to cells that have a cellular phenotype that is more primitive (i.e., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

A "precursor thereof" as the term relates to an insulin-positive endocrine cell refers to any cell that is capable of differentiating into an insulin-positive endocrine cell, including for example, a pluripotent stem cell, a definitive endoderm cell, a primitive gut tube cell, a pancreatic progenitor cell, or endocrine progenitor cell, when cultured under conditions suitable for differentiating the precursor cell into the insulin-positive endocrine cell.

The term "endocrine cell(s)" refers to hormone-producing cells present in the pancreas of an organism, such as "islet", "islet cells", "islet equivalent", "islet-like cells", "pancreatic islets" and their grammatical equivalents. In an embodiment, the endocrine cells can be differentiated from pancreatic progenitor cells or precursors. Islet cells can comprise different types of cells, including, but not limited to, pancreatic α cells, pancreatic β cells, pancreatic S cells, pancreatic F cells, and/or pancreatic ε cells. Islet cells can also refer to a group of cells, cell clusters, or the like.

The term "exocrine cell" as used herein refers to a cell of an exocrine gland, i.e. a gland that discharges its secretion via a duct. In particular embodiments, an exocrine cell refers to a pancreatic exocrine cell, which is a pancreatic cell that produces enzymes that are secreted into the small intestine. These enzymes help digest food as it passes through the gastrointestinal tract. Pancreatic exocrine cells are also known as islets of Langerhans, which secrete two hormones, insulin and glucagon. A pancreatic exocrine cell can be one of several cell types; α-2 cells (which produce the hormone glucagon); or β cells (which manufacture the hormone insulin); and α-1 cells (which produce the regulatory agent somatostatin). Non-insulin-producing exocrine cells, as the term is used herein, refers to α-2 cells or α-1 cells. The term pancreatic exocrine cells encompasses "pancreatic endocrine cells" which refer to a pancreatic cell that produces hormones (e.g., insulin (produced from β cells), glucagon (produced by alpha-2 cells), somatostatin (produced by delta cells) and pancreatic polypeptide (produced by F cells) that are secreted into the bloodstream.

The terms "insulin-positive β-like cell," "insulin-positive endocrine cell," and their grammatical equivalents, refer to cells that displays at least one marker indicative of a pancreatic β cell and also expresses insulin but lack a glucose stimulated insulin secretion (GSIS) response characteristic of a mature pancreatic β cell.

The term "NKX6.1 expressing, ISL1 expressing β cells," refers to cells that express both NKX6.1 and ISL1 but lack a glucose stimulated insulin secretion (GSIS) response characteristic of a mature pancreatic β cell. NKX6.1 expressing, ISL1 expressing β cells may express insulin.

The term "β cell marker" refers to, without limitation, proteins, peptides, nucleic acids, polymorphism of proteins and nucleic acids, splice variants, fragments of proteins or nucleic acids, elements, and other analytes which are specifically expressed or present in pancreatic β cells. Exemplary β cell markers include, but are not limited to, pancreatic and duodenal homeobox 1 (Pdx1) polypeptide, insulin, c-peptide, amylin, E-cadherin, Hnf3β, PCI/3, B2, Nkx2.2, GLUT2, PC2, ZnT-8, Isl1, Pax6, Pax4, NeuroD, 1 Inf1b, Hnf-6, Hnf-3beta, and MafA, and those described in Zhang et al., Diabetes. 50(10):2231-6 (2001). In some embodiment, the β cell marker is a nuclear 3-cell marker. In some embodiments, the β cell marker is Pdx1 or PH3.

The term "pancreatic endocrine marker" refers to without limitation, proteins, peptides, nucleic acids, polymorphism of proteins and nucleic acids, splice variants, fragments of proteins or nucleic acids, elements, and other analytes which are specifically expressed or present in pancreatic endocrine cells. Exemplary pancreatic endocrine cell markers include, but are not limited to, Ngn-3, NeuroD and Islet-1.

The term "pancreatic endocrine progenitor" or "pancreatic endocrine precursor" and their grammatical equivalents are used interchangeably herein and refer to an endocrine progenitor cells which is capable of becoming a pancreatic hormone secreting cell. These cells are committed to differentiating towards at least one type of pancreatic endocrine cell, e.g. beta cells that produce insulin; alpha cells that produce glucagon; delta cells (or β cells) that produce somatostatin; and/or F cells that produce pancreatic polypeptide. Such cells can express at least one of the following markers: Ngn3, NKX2.2, NeuroD, ISL-1, Pax4, Pax6, or ARX.

The term "Ngn3-positive endocrine progenitor" as used herein refers to precursors of pancreatic endocrine cells expressing the transcription factor Neurogenin-3 (Ngn3). Progenitor cells are more differentiated than multipotent stem cells and can differentiate into only few cell types. In particular, Ngn3-positive endocrine progenitor cells have the ability to differentiate into the five pancreatic endocrine cell types (α, β, δ, ε and PP). The expression of Ngn3 may be assessed by any method known by the skilled person such as immunochemistry using an anti-Ngn3 antibody or quantitative RT-PCR.

The terms "NeuroD" and "NeuroD1" are used interchangeably and identify a protein expressed in pancreatic endocrine progenitor cells and the gene encoding it.

The term "pdx1 expressing pancreatic progenitor" as used herein refers to a cell which is a pancreatic endoderm (PE) cell which has the capacity to differentiate into SC-β cells, such as pancreatic β cells. A Pdx1 expressing pancreatic progenitor expresses the marker Pdx1. Other markers include, but are not limited to Cdcp1, or Ptf1a, or HNF6 or NRx2.2. The expression of Pdx1 may be assessed by any method known by the skilled person such as immunochemistry using an anti-Pdx1 antibody or quantitative RT-PCR.

The term "pdx1 expressing, NKX6.1 expressing pancreatic progenitor" as used herein refers to a cell which is a pancreatic endoderm (PE) cell which has the capacity to differentiate into insulin-producing cells, such as pancreatic β cells. A pdx1-expressing, NKX6.1-expressing pancreatic progenitor expresses the markers Pdx1 and NKX6.1. Other markers include, but are not limited to Cdcp1, or Ptf1a, or HNF6 or NRx2.2. The expression of NKX6.1 may be assessed by any method known by the skilled person such as immunochemistry using an anti-NKX6.1 antibody or quantitative RT-PCR.

The terms "stem cell-derived β cell", "SC-β cell", "functional β cell", "functional pancreatic β cell", "mature SC-β cell", and their grammatical equivalents refer to cells (e.g., pancreatic β cells) that display at least one marker indicative of a pancreatic β cell (e.g., PDX-1 or NKX6.1), expresses insulin, and display a glucose stimulated insulin secretion (GSIS) response characteristic of an endogenous mature β cell. In some embodiments, the "SC-β cell" comprises a mature pancreatic cell. It is to be understood that the SC-β cells need not be derived (e.g., directly) from stem cells, as the methods of the disclosure are capable of deriving SC-β cells from any insulin-positive endocrine cell or precursor thereof using any cell as a starting point (e.g., one can use embryonic stem cells, induced-pluripotent stem cells, progenitor cells, partially reprogrammed somatic cells (e.g., a somatic cell which has been partially reprogrammed to an intermediate state between an induced pluripotent stem cell and the somatic cell from which it was derived), multipotent cells, totipotent cells, a transdifferentiated version of any of the foregoing cells, etc, as the invention is not intended to be limited in this manner). In some embodiments, the SC-β cells exhibit a response to multiple glucose challenges (e.g., at least one, at least two, or at least three or more sequential glucose challenges). In some embodiments, the response resembles the response of endogenous islets (e.g., human islets) to multiple glucose challenges. In some embodiments, the morphology of the SC-β cell resembles the morphology of an endogenous β cell. In some embodiments, the SC-β cell exhibits an in vitro GSIS response that resembles the GSIS response of an endogenous β cell. In some embodiments, the SC-β cell exhibits an in vivo GSIS response that resembles the GSIS response of an endogenous β cell. In some embodiments, the SC-β cell exhibits both an in vitro and in vivo GSIS response that resembles the GSIS response of an endogenous β cell. The GSIS response of the SC-β cell can be observed within two weeks of transplantation of the SC-β cell into a host (e.g., a human or animal). In some embodiments, the SC-β cells package insulin into secretory granules. In some embodiments, the SC-β cells exhibit encapsulated crystalline insulin granules. In some embodiments, the SC-β cells exhibit a stimulation index of greater than 1. In some embodiments, the SC-β cells exhibit a stimulation index of greater than 1.1. In some embodiments, the SC-β cells exhibit a stimulation index of greater than 2. In some embodiments, the SC-β cells exhibit cytokine-induced apoptosis in response to cytokines. In some embodiments, insulin secretion from the SC-β cells is enhanced in response to known antidiabetic drugs (e.g., secretagogues). In some embodiments, the SC-β cells are monohormonal. In some embodiments, the SC-β cells do not abnormally co-express other hormones, such as glucagon, somatostatin or pancreatic polypeptide. In some embodiments, the SC-β cells exhibit a low rate of replication. In some embodiments, the SC-β cells increase intracellular Ca2+ in response to glucose.

As used herein, the term "insulin producing cell" and its grammatical equivalent refer to a cell differentiated from a pancreatic progenitor, or precursor thereof, which secretes insulin. An insulin-producing cell includes pancreatic β cell as that term is described herein, as well as pancreatic β-like cells (i.e., insulin-positive, endocrine cells) that synthesize (i.e., transcribe the insulin gene, translate the proinsulin mRNA, and modify the proinsulin mRNA into the insulin protein), express (i.e., manifest the phenotypic trait carried by the insulin gene), or secrete (release insulin into the extracellular space) insulin in a constitutive or inducible manner. A population of insulin producing cells e.g. produced by differentiating insulin-positive, endocrine cells or a precursor thereof into SC-β cells according to the methods of the present disclosure can be pancreatic β cell or (β-like cells (e.g., cells that have at least one, or at least two least two) characteristic of an endogenous β cell and exhibit a glucose stimulated insulin secretion (GSIS) response that resembles an endogenous adult β cell. The population of insulin-producing cells, e.g. produced by the methods as disclosed herein can comprise mature pancreatic β cell or SC-β cells, and can also contain non-insulin-producing cells (i.e. cells of cell like phenotype with the exception they do not produce or secrete insulin).

The term "epigenetics" refers to heritable changes in gene function that do not involve changes in the DNA sequence. Epigenetics most often denotes changes in a chromosome that affect gene activity and expression, but can also be used to describe any heritable phenotypic change that does not derive from a modification of the genome. Such effects on cellular and physiological phenotypic traits can result from external or environmental factors, or be part of normal developmental program. Epigenetics can also refer to functionally relevant changes to the genome that do not involve a change in the nucleotide sequence. Examples of mechanisms that produce such changes are DNA methylation and histone modification, each of which alters how genes are expressed without altering the underlying DNA sequence. Gene expression can be controlled through the action of repressor proteins that attach to silencer regions of the DNA. These epigenetic changes can last through cell divisions for the duration of the cell's life, and can also last for multiple generations even though they do not involve changes in the underlying DNA sequence of the organism. One example of an epigenetic change in eukaryotic biology is the process of cellular differentiation. During morphogenesis, totipotent stem cells become the various pluripotent cells, which in turn can become fully differentiated cells.

The term "epigenetic modifying compound" refers to a chemical compound that can make epigenetic changes genes, i.e., change gene expression(s) without changing DNA sequences. Epigenetic changes can help determine whether genes are turned on or off and can influence the production of proteins in certain cells, e.g., beta-cells. Epigenetic modifications, such as DNA methylation and histone modification, alter DNA accessibility and chromatin structure, thereby regulating patterns of gene expression. These processes are crucial to normal development and differentiation of distinct cell lineages in the adult organism. They can be modified by exogenous influences, and, as such, can contribute to or be the result of environmental alterations of phenotype or pathophenotype. Importantly, epigenetic modification has a crucial role in the regulation of pluripotency genes, which become inactivated during differentiation. Non-limiting exemplary epigenetic modifying compound include a DNA methylation inhibitor, a histone acetyltransferase inhibitor, a histone deacetylase inhibitor, a histone methyltransferase inhibitor, a bromodomain inhibitor, or any combination thereof.

The term "differentiated cell" or its grammatical equivalents is meant any primary cell that is not, in its native form, pluripotent as that term is defined herein. Stated another way, the term "differentiated cell" refers to a cell of a more specialized cell type derived from a cell of a less specialized cell type (e.g., a stem cell such as an induced pluripotent stem cell) in a cellular differentiation process. Without wishing to be limited to theory, a pluripotent stem cell in the course of normal ontogeny can differentiate first to an endoderm cell that is capable of forming pancreas cells and other endoderm cell types. Further differentiation of an endoderm cell leads to the pancreatic pathway, where ~98% of the cells become exocrine, ductular, or matrix cells, and ~2% become endocrine cells. Early endocrine cells are islet progenitors, which can then differentiate further into insulin-producing cells (e.g. functional endocrine cells) which secrete insulin, glucagon, somatostatin, or pancreatic polypeptide. Endoderm cells can also be differentiate into other cells of endodermal origin, e.g. lung, liver, intestine, thymus etc.

As used herein, the term "somatic cell" refers to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for converting at least one insulin-positive endocrine cell or precursor thereof to an insulin-producing, glucose responsive cell can be performed both in vivo and in vitro (where in vivo is practiced when at least one insulin-positive endocrine cell or precursor thereof are present within a subject, and where in vitro is practiced using an isolated at least one insulin-positive endocrine cell or precursor thereof maintained in culture).

As used herein, the term "adult cell" refers to a cell found throughout the body after embryonic development.

The term "endoderm cell" as used herein refers to a cell which is from one of the three primary germ cell layers in the very early embryo (the other two germ cell layers are the mesoderm and ectoderm). The endoderm is the innermost of the three layers. An endoderm cell differentiates to give rise first to the embryonic gut and then to the linings of the respiratory and digestive tracts (e.g. the intestine), the liver and the pancreas.

The term "a cell of endoderm origin" as used herein refers to any cell which has developed or differentiated from an endoderm cell. For example, a cell of endoderm origin includes cells of the liver, lung, pancreas, thymus, intestine, stomach and thyroid. Without wishing to be bound by theory, liver and pancreas progenitors (also referred to as pancreatic progenitors) are develop from endoderm cells in the embryonic foregut. Shortly after their specification, liver and pancreas progenitors rapidly acquire markedly different cellular functions and regenerative capacities. These changes are elicited by inductive signals and genetic regulatory factors that are highly conserved among vertebrates. Interest in the development and regeneration of the organs has been fueled by the intense need for hepatocytes and pancreatic β cells in the therapeutic treatment of liver failure and type I diabetes. Studies in diverse model organisms and humans have revealed evolutionarily conserved inductive signals and transcription factor networks that elicit the differentiation of liver and pancreatic cells and provide guidance for how to promote hepatocyte and β cell differentiation from diverse stem and progenitor cell types.

The term "definitive endoderm" as used herein refers to a cell differentiated from an endoderm cell and which can be differentiated into a SC-β cell (e.g., a pancreatic β cell). A definitive endoderm cell expresses the marker Sox17. Other markers characteristic of definitive endoderm cells include, but are not limited to MIXL2, GATA4, HNF3b, GSC, FGF17, VWF, CALCR, FOXQ1, CXCR4, Cerberus, OTX2, goosecoid, C-Kit, CD99, CMKOR1 and CRIP1. In particular, definitive endoderm cells herein express Sox17 and in some embodiments Sox17 and HNF3B, and do not express significant levels of GATA4, SPARC, APF or DAB. Definitive endoderm cells are not positive for the marker Pdx1 (e.g. they are Pdx1-negative). Definitive endoderm cells have the capacity to differentiate into cells including those of the liver, lung, pancreas, thymus, intestine, stomach and thyroid. The expression of Sox17 and other markers of definitive endoderm may be assessed by any method known by the skilled person such as immunochemistry, e.g., using an anti-Sox17 antibody, or quantitative RT-PCR.

The term "pancreatic endoderm" refers to a cell of endoderm origin which is capable of differentiating into multiple pancreatic lineages, including pancreatic β cells, but no longer has the capacity to differentiate into non-pancreatic lineages.

The term "primitive gut tube cell" or "gut tube cell" as used herein refers to a cell differentiated from an endoderm cell and which can be differentiated into a SC-β cell (e.g., a pancreatic β cell). A primitive gut tube cell expresses at least one of the following markers: HNP1-β, HNF3-β or HNF4-α. Primitive gut tube cells have the capacity to differentiate into cells including those of the lung, liver, pancreas, stomach, and intestine. The expression of HNF1-β and other markers of primitive gut tube may be assessed by any method known by the skilled person such as immunochemistry, e.g., using an anti-HNF1-β antibody.

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retro-differentiation" by persons of ordinary skill in the art. As used herein, the term "pluripotent stem cell" includes embryonic stem cells, induced pluripotent stem cells, placental stem cells, etc.

The term "pluripotent" as used herein refers to a cell with the capacity, under different conditions, to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. It should be noted that simply culturing such cells does not, on its own, render them pluripotent. Reprogrammed pluripotent cells (e.g. iPS cells as that term is defined herein) also have the characteristic of the capacity of extended passaging without loss of growth potential, relative to primary cell parents, which generally have capacity for only a limited number of divisions in culture.

As used herein, the terms "iPS cell" and "induced pluripotent stem cell" are used interchangeably and refers to a pluripotent stem cell artificially derived (e.g., induced or by complete reversal) from a non-pluripotent cell, typically an adult somatic cell, for example, by inducing a forced expression of one or more genes.

The term "phenotype" refers to one or a number of total biological characteristics that define the cell or organism under a particular set of environmental conditions and factors, regardless of the actual genotype.

The terms "subject", "patient", or "individual" are used interchangeably herein, and refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g, dog, cat, horse, and the like, or production mammal, e.g. cow, sheep, pig, and the like. "Patient in need thereof" or "subject in need thereof" is referred to herein as a patient diagnosed with or suspected of having a disease or disorder, for instance, but not restricted to diabetes.

"Administering" is referred to herein as providing one or more compositions described herein to a patient or a subject. By way of example and not limitation, composition administration, e.g., injection, can be performed by intravenous (i.v.) injection, sub-cutaneous (s.c.) injection, intradermal (id.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device. In an embodiment, a composition of the present disclosure can comprise engineered cells or host cells expressing nucleic acid sequences described herein, or a vector comprising at least one nucleic acid sequence described herein, in an amount that is effective to treat or prevent proliferative disorders. A pharmaceutical composition can comprise the cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

As used herein, the term "treating" and "treatment" refers to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment. Those in need of treatment include those already diagnosed with a cardiac condition, as well as those likely to develop a cardiac condition due to genetic susceptibility or other factors such as weight, diet and health.

The term "therapeutically effective amount", "therapeutic amount," or its grammatical equivalents refers to an amount effective, at dosages and for periods of time necessary, to achieve a desired therapeutic result. The therapeutically effective amount can vary according to factors such as the disease state, age, sex, and weight of the individual and the ability of a composition described herein to elicit a desired response in one or more subjects. The precise amount of the compositions of the present disclosure to be administered can be determined by a physician with consideration of individual differences in age, weight, tumor size, extent of infection or metastasis, and condition of the patient (subject).

Alternatively, the pharmacologic and/or physiologic effect of administration of one or more compositions described herein to a patient or a subject of can be "prophylactic," i.e., the effect completely or partially prevents a disease or symptom thereof. A "prophylactically effective amount" refers to an amount effective, at dosages and for periods of time necessary, to achieve a desired prophylactic result (e.g., prevention of disease onset).

Some numerical values disclosed throughout are referred to as, for example, "X is at least or at least about 100; or 200 [or any numerical number]." This numerical value includes the number itself and all of the following:
  i) X is at least 100;
  ii) X is at least 200;
  iii) X is at least about 100; and
  iv) X is at least about 200.

All these different combinations are contemplated by the numerical values disclosed throughout. All disclosed numerical values should be interpreted in this manner, whether it refers to an administration of a therapeutic agent or referring to days, months, years, weight, dosage amounts, etc., unless otherwise specifically indicated to the contrary.

The ranges disclosed throughout are sometimes referred to as, for example, "X is administered on or on about day 1 to 2; or 2 to 3 [or any numerical range]." This range includes the numbers themselves (e.g., the endpoints of the range) and all of the following:
  i) X being administered on between day 1 and day 2;
  ii) X being administered on between day 2 and day 3;
  iii) X being administered on between about day 1 and day 2;
  iv) X being administered on between about day 2 and day 3;
  v) X being administered on between day 1 and about day 2;
  vi) X being administered on between day 2 and about day 3;
  vii) X being administered on between about day 1 and about day 2; and
  viii) X being administered on between about day 2 and about day 3.

All these different combinations are contemplated by the ranges disclosed throughout. All disclosed ranges should be interpreted in this manner, whether it refers to an administration of a therapeutic agent or referring to days, months, years, weight, dosage amounts, etc., unless otherwise specifically indicated to the contrary.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. The term "selectable marker" as used herein can refer to a gene or to an expression product of the gene, e.g., an encoded protein. In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, i.e., "selective conditions." To ensure an effective selection, a population of cells can be maintained for a under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

Reprogramming

The term "reprogramming" as used herein refers to the process that alters or reverses the differentiation state of a somatic cell. The cell can either be partially or terminally differentiated prior to the reprogramming. Reprogramming encompasses complete reversion of the differentiation state of a somatic cell to a pluripotent cell. Such complete reversal of differentiation produces an induced pluripotent (iPS) cell. Reprogramming as used herein also encompasses partial reversion of a cells differentiation state, for example to a multipotent state or to a somatic cell that is neither pluripotent or multipotent, but is a cell that has lost one or more specific characteristics of the differentiated cell from which it arises, e.g. direct reprogramming of a differentiated cell to a different somatic cell type. Reprogramming generally involves alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult.

As used herein, the term "reprogramming factor" is intended to refer to a molecule that is associated with cell "reprogramming", that is, differentiation, and/or de-differentiation, and/or transdifferentiation, such that a cell converts to a different cell type or phenotype. Reprogramming factors generally affect expression of genes associated with cell differentiation, de-differentiation and/or transdifferentiation. Transcription factors are examples of reprogramming factors.

The term "differentiation" and their grammatical equivalents as used herein refers to the process by which a less specialized cell (i.e., a more naive cell with a higher cell potency) becomes a more specialized cell type (i.e., a less naive cell with a lower cell potency); and that the term "de-differentiation" refers to the process by which a more specialized cell becomes a less specialized cell type (i.e., a more naive cell with a higher cell potency); and that the term "transdifferentiation" refers to the process by which a cell of a particular cell type converts to another cell type without significantly changing its "cell potency" or "naivety" level. Without wishing to be bound by theory, it is thought that cells "transdifferentiate" when they convert from one lineage-committed cell type or terminally differentiated cell type to another lineage-committed cell type or terminally differentiated cell type, without significantly changing their "cell potency" or "naivety" level.

As used herein, the term "cell potency" is to be understood as referring to the ability of a cell to differentiate into cells of different lineages. For example, a pluripotent cell (e.g., a stem cell) has the potential to differentiate into cells of any of the three germ layers, that is, endoderm (interior stomach lining, gastrointestinal tract, the lungs), mesoderm (muscle, bone, blood, urogenital), or ectoderm (epidermal tissues and nervous system), and accordingly has high cell potency; a multipotent cell (e.g., a stem cell or an induced stem cell of a certain type) has the ability to give rise to cells from a multiple, but limited, number of lineages (such as hematopoietic stem cells, cardiac stem cells, or neural stem cells, etc) comparatively has a lower cell potency than pluripotent cells. Cells that are committed to a particular lineage or are terminally differentiated can have yet a lower cell potency. Specific examples of transdifferentiation known in the art include the conversion of e.g., fibroblasts beta cells or from pancreatic exocrine cells to beta cells etc.

Accordingly, the cell may be caused to differentiate into a more naive cell (e.g., a terminally differentiated cell may be differentiated to be multipotent or pluripotent); or the cell may be caused to de-differentiate into a less naive cell (e.g., a multipotent or pluripotent cell can be differentiated into a lineage-committed cell or a terminally differentiated cell). However, in an embodiment, the cell may be caused to convert or transdifferentiate from one cell type (or phenotype) to another cell type (or phenotype), for example, with a similar cell potency level. Accordingly, in an embodiment of the present disclosure, the inducing steps of the present disclosure can reprogram the cells of the present disclosure to differentiate, de-differentiate and/or transdifferentiate. In an embodiment of the present disclosure, the inducing steps of the present disclosure may reprogram the cells to transdifferentiate.

Methods of reprogramming or inducing a particular type of cell to become another type of cell, for example, by differentiation, de-differentiation and/or transdifferentiation using one or more exogenous polynucleotide or polypeptide reprogramming factors are known to the person skilled in the art. Such methods may rely on the introduction of genetic material encoding one or more transcription factor(s) or other polypeptide(s) associated with cell reprogramming. For example, Pdx1, Ngn3 and MafA, or functional fragments thereof are all known to encode peptides that can induce cell differentiation, de-differentiation and/or transdifferentiation of the cells of the present disclosure. In some methods known to the person skilled in the art, exogenous polypeptides (e.g. recombinant polypeptides) encoded by reprogramming genes (such as the above genes) are contacted with the cells to induce, for example, cells of the present disclosure. The person skilled in the art will appreciate that other genes may be associated with reprogramming of cells, and exogenous molecules encoding such genes (or functional fragments thereof) and the encoded polypeptides are also considered to be polynucleotide or polypeptide reprogramming factors (e.g. polynucleotides or polypeptides that in turn affect expression levels of another gene associated with cell reprogramming). For example, it has been shown that the introduction of exogenous polynucleotide or polypeptide epigenetic gene silencers that decrease p53 inactivation increase the efficiency of inducing induced pluripotent stem cells (iPSC). Accordingly, exogenous polynucleotides or polypeptides encoding epigenetic silencers and other genes or proteins that may be directly or indirectly involved in cell reprogramming or increasing cell programming efficiency would be considered to constitute an exogenous polynucleotide or polypeptide reprogramming factor. The person skilled in the art will appreciate that other methods of influencing cell reprogramming exist, such as introducing RNAi molecules (or genetic material encoding RNAi molecules) that can knock down expression of genes involved in inhibiting cell reprogramming. Accordingly, any exogenous polynucleotide molecule or polypeptide molecule that is associated with cell reprogramming, or enhances cell reprogramming, is to be understood to be an exogenous polynucleotide or polypeptide reprogramming factor as described herein.

In some embodiments of the present disclosure, the method excludes the use of reprogramming factor(s) that are not small molecules. However, it will be appreciated that the method may utilize "routine" tissue culture components such as culture media, serum, serum substitutes, supplements, antibiotics, etc, such as RPMI, Renal Epithelial Basal Medium (REBM), Dulbecco's Modified Eagle Medium (DMEM), MCDB131 medium, CMRL 1066 medium, F12, foetal calf serum (FCS), foetal bovine serum (FBS), bovine serum albumin (BSA), D-glucose, L-glutamine, GlutaMAX™-1 (dipeptide, L-alanine-L-glutamine), B27, heparin, progesterone, putrescine, laminin, nicotinamide, insulin, transferrin, sodium selenite, selenium, ethanolamine, human epidermal growth factor (hEGF), basic fibroblast growth factor (bFGF), hydrocortisone, epinephrine, normacin, penicillin, streptomycin, gentamicin and amphotericin, etc. It is to be understood that these typical tissue culture components (and other similar tissue culture components that are routinely used in tissue culture) are not small molecule reprogramming molecules for the purposes of the present disclosure. Indeed, these components are either not small molecules as defined herein and/or are not reprogramming factors as defined herein.

Accordingly, in an embodiment, the present disclosure does not involve a culturing step of the cell(s) with one or more exogenous polynucleotide or polypeptide reprogramming factor(s). Accordingly, in an embodiment, the method of the present disclosure does not involve the introduction of one or more exogenous polynucleotide or polypeptide reprogramming factor(s), e.g., by introducing transposons, viral transgenic vectors (such as retroviral vectors), plasmids, mRNA, miRNA, peptides, or fragments of any of these molecules, that are involved in producing induced beta cells or, otherwise, inducing cells of the present disclosure to differentiate, de-differentiate and/or transdifferentiate.

That is, in an embodiment, the method occurs in the absence of one or more exogenous polynucleotide or polypeptide reprogramming factor(s). Accordingly, it is to be understood that in an embodiment, the method of the present disclosure utilizes small molecules (e.g., HDAC inhibitors) to reprogram cells, without the addition of polypeptide transcription factors; other polypeptide factors specifically associated with inducing differentiation, de-differentiation, and/or transdifferentiation; polynucleotide sequences encoding polypeptide transcription factors, polynucleotide sequences encoding other polypeptide factors specifically associated with inducing differentiation, de-differentiation, and/or transdifferentiation; mRNA; interference RNA; microRNA and fragments thereof.

In some cases, pancreatic differentiation as disclosed herein is carried out in a step-wise manner. In the step-wise progression, "Stage 1" or "S1" refers to the first step in the differentiation process, the differentiation of pluripotent stem cells into cells expressing markers characteristic of definitive endoderm cells ("DE", "Stage 1 cells" or "S1 cells"). "Stage 2" refers to the second step, the differentiation of cells expressing markers characteristic of definitive endoderm cells into cells expressing markers characteristic of gut tube cells ("GT", "Stage 2 cells" or "S2 cells"). "Stage 3" refers to the third step, the differentiation of cells expressing markers characteristic of gut tube cells into cells expressing markers characteristic of pancreatic progenitor 1 cells ("PP1", "Stage 3 cells" or "S3 cells"). "Stage 4" refers to the fourth step, the differentiation of cells expressing markers characteristic of pancreatic progenitor 1 cells into cells expressing markers characteristic of pancreatic progenitor 2 cells ("PP2", "Stage 4 cells" or "S4 cells"). "Stage 5" refers to the fifth step, the differentiation of cells expressing markers characteristic of pancreatic progenitor 2 cells into cells expressing markers characteristic of pancreatic endoderm cells and/or pancreatic endocrine progenitor cells ("EN", "Stage 5 cells" or "S5 cells"). "Stage 6" refers to the differentiation of cells expressing markers characteristic of pancreatic endocrine progenitor cells into cells expressing markers characteristic of pancreatic endocrine β cells ("SC-β cells") or pancreatic endocrine α cells ("SC-α cells"). It should be appreciated, however, that not all cells in a particular population progress through these stages at the same rate, i.e., some cells may have progressed less, or more, down the differentiation pathway than the majority of cells present in the population.

Stem Cells

The term "stem cell" is used herein to refer to a cell (e.g., plant stem cell, vertebrate stem cell) that has the ability both to self-renew and to generate a differentiated cell type (Morrison et al. (1997) Cell 88:287-298). In the context of cell ontogeny, the adjective "differentiated," or "differentiating" is a relative term. A "differentiated cell" is a cell that has progressed further down the developmental pathway than the cell it is being compared with. Thus, pluripotent stem cells can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and can or cannot retain the capacity to proliferate further. Stem cells can be characterized by both the presence of specific markers (e.g., proteins, RNAs, etc.) and the absence of specific markers. Stem cells can also be identified by functional assays both in vitro and in vivo, particularly assays relating to the ability of stem cells to give rise to multiple differentiated progeny. In an embodiment, the host cell is an adult stem cell, a somatic stem cell, a non-embryonic stem cell, an embryonic stem cell, hematopoietic stem cell, an include pluripotent stem cells, and a trophoblast stem cell.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs can be in the form of an established cell line, they can be obtained directly from primary embryonic tissue, or they can be derived from a somatic cell.

By "embryonic stem cell" (ESC) is meant a PSC that is isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hESI (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells can be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, each of which is incorporated herein by its entirety. Methods for proliferating hESCs in the undifferentiated form are described in WO 99/20741, WO 01/51616, and WO 03/020920, each of which is incorporated herein by its entirety.

By "embryonic germ stem cell" (EGSC) or "embryonic germ cell" or "EG cell," it is meant a PSC that is derived from germ cells and/or germ cell progenitors, e.g. primordial germ cells, i.e. those that can become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, each of which are incorporated herein by its entirety.

By "induced pluripotent stem cell" or "iPSC," it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs can be found in, for example, U.S. Patent Publication Nos. US20090047263, US20090068742, US20090191159, US20090227032, US20090246875, and US20090304646, each of which are incorporated herein by its entirety. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell," it is meant any cell in an organism that, in the absence of experimental manipulation, does not ordinarily give rise to all types of cells in an organism. In other words, somatic cells are cells that have differentiated sufficiently that they do not naturally generate cells of all three germ layers of the body, i.e. ectoderm, mesoderm and endoderm. For example, somatic cells can include both neurons and neural progenitors, the latter of which is able to naturally give rise to all or some cell types of the central nervous system but cannot give rise to cells of the mesoderm or endoderm lineages.

In certain examples, the stem cells can be undifferentiated (e.g. a cell not committed to a specific lineage) prior to exposure to at least one β cell maturation factor according to the methods as disclosed herein, whereas in other examples it may be desirable to differentiate the stem cells to one or more intermediate cell types prior to exposure of the at least one cell maturation factor (s) described herein. For example, the stems cells may display morphological, biological or physical characteristics of undifferentiated cells that can be used to distinguish them from differentiated cells of embryo or adult origin. In some examples, undifferentiated cells may appear in the two dimensions of a microscopic view in colonies of cells with high nuclear/cytoplasmic ratios and prominent nucleoli. The stem cells may be themselves (for example, without substantially any undifferentiated cells being present) or may be used in the presence of differentiated cells. In certain examples, the stem cells may be cultured in the presence of) suitable nutrients and optionally other cells such that the stem cells can grow and optionally differentiate. For example, embryonic fibroblasts or fibroblast-like cells may be present in the culture to assist in the growth of the stem cells. The fibroblast may be present during one stage of stem cell growth but not necessarily at all stages. For example, the fibroblast may be added to stem cell cultures in a first culturing stage and not added to the stem cell cultures in one or more subsequent culturing stages.

Stem cells used in all aspects of the present invention can be any cells derived from any kind of tissue (for example embryonic tissue such as fetal or pre-fetal tissue, or adult tissue), which stem cells have the characteristic of being capable under appropriate conditions of producing progeny of different cell types, e.g. derivatives of all of at least one of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hESI (MizMedi Hospital-Seoul National University); HSF-1, FISF-6 (University of California at San Francisco); and H1, H7, H9, H13, H14 (Wisconsin Alumni Research Foundation (WiCell Research Institute)). In some embodiments, the source of human stem cells or pluripotent stem cells used for chemically-induced differentiation into mature, insulin positive cells did not involve destroying a human embryo.

In another embodiment, the stem cells can be isolated from tissue including solid tissue. In some embodiments, the tissue is skin, fat tissue (e.g. adipose tissue), muscle tissue, heart or cardiac tissue. In other embodiments, the tissue is for example but not limited to, umbilical cord blood, placenta, bone marrow, or chondral.

Stem cells of interest also include embryonic cells of various types, exemplified by human embryonic stem (hES) cells, described by Thomson et al, (1998) Science 282:1145; embryonic stem cells from other primates, such as Rhesus stem cells (Thomson et al. (1995) Proc. Natl. Acad. Sci. USA 92:7844); marmoset stem cells (Thomson et al. (1996) Biol. Reprod. 55:254); and human embryonic germ (hEG) cells (Shambloft et al., Proc. Natl. Acad. Sci. USA 95:13726, 1998). Also of interest are lineage committed stem cells, such as mesodermal stem cells and other early cardiogenic cells (see Reyes et al, (2001) Blood 98:2615-2625; Eisenberg & Bader (1996) Circ Res. 78(2):205-16; etc.) The stem cells may be obtained from any mammalian species, e.g. human, equine, bovine, porcine, canine, feline, rodent, e.g. mice, rats, hamster, primate, etc. In some embodiments, a human embryo was not destroyed for the source of pluripotent cell used on the methods and compositions as disclosed herein.

A mixture of cells from a suitable source of endothelial, muscle, and/or neural stem cells can be harvested from a mammalian donor by methods known in the art. A suitable source is the hematopoietic microenvironment. For example, circulating peripheral blood, preferably mobilized (i.e., recruited), may be removed from a subject. In an embodiment, the stem cells can be reprogrammed stem cells, such as stem cells derived from somatic or differentiated cells. In such an embodiment, the de-differentiated stem cells can be for example, but not limited to, neoplastic cells, tumor cells and cancer cells or alternatively induced reprogrammed cells such as induced pluripotent stem cells or iPS cells.

In some embodiments, the SC-β cell can be derived from one or more of trichocytes, keratinocytes, gonadotropes, corticotropes, thyrotropes, somatotropes, lactotrophs, chromaffin cells, parafollicular cells, glomus cells melanocytes, nevus cells, Merkel cells, odontoblasts, cementoblasts corneal keratocytes, retina Muller cells, retinal pigment epithelium cells, neurons, glias (e.g., oligodendrocyte astrocytes), ependymocytes, pinealocytes, pneumocytes (e.g., type I pneumocytes, and type II pneumocytes), clara cells, goblet cells, G cells, β cells, ECL cells, gastric chief cells, parietal cells, foveolar cells, K cells, β cells, I cells, goblet cells, paneth cells, enterocytes, microfold cells, hepatocytes, hepatic stellate cells (e.g., Kupffer cells from mesoderm), cholecystocytes, centroacinar cells, pancreatic stellate cells, pancreatic α cells, pancreatic β cells, pancreatic δ cells, pancreatic F cells (e.g., PP cells), pancreatic ε cells, thyroid (e.g., follicular cells), parathyroid (e.g., parathyroid chief cells), oxyphil cells, urothelial cells, osteoblasts, osteocytes, chondroblasts, chondrocytes, fibroblasts, fibrocytes, myoblasts, myocytes, myosatellite cells, tendon cells, cardiac muscle cells, lipoblasts, adipocytes, interstitial cells of cajal, angioblasts, endothelial cells, mesangial cells (e.g., intraglomerular mesangial cells and extraglomerular mesangial cells), juxtaglomerular cells, macula densa cells, stromal cells, interstitial cells, telocytes simple epithelial cells, podocytes, kidney proximal tubule brush border cells, sertoli cells, leydig cells, granulosa cells, peg cells, germ cells, spermatozoon ovums, lymphocytes, myeloid cells, endothelial progenitor cells, endothelial stem cells, angioblasts, mesoangioblasts, pericyte mural cells, splenocytes (e.g., T lymphocytes, B lymphocytes, dendritic cells, microphages, leukocytes), trophoblast stem cells, or any combination thereof.

Definitive Endoderm Cells

In some aspects, the present disclosure provides methods of producing definitive endoderm cells from a population of human pluripotent stem cells comprising contacting said population of human pluripotent stem cells with at least one or two of a Wnt signaling pathway activator or an activator of TGF-β signaling pathway. In some embodiments, the Wnt signaling pathway activator is CHIR99021. In some embodiments, the activator of TGF-β signaling pathway is Activin A. In some embodiments, the Wnt signaling pathway activator is CHIR99021, BML-284; 2-Amino-4-[3,4-(methylenedioxy)benzylamino]-6-(3-methoxyphenyl)pyrimidine (CAS 853220-52-7), DKK1 inhibitor; (1-(4-(Naphthalen-2-yl)pyrimidin-2-yl)piperidin-4-yl) methanamine (WAY 262611). In some embodiments, the activator of TGF-β signaling pathway is Activin A, GDF1, GDF11, Nodal, or TGFβ.

Primitive Gut Tube Cells

In some aspects, the present disclosure provides methods of producing primitive gut tube cells from a population of definitive endoderm cells comprising contacting said population of human pluripotent stem cells with a fibroblast growth factor (FGF) family member. In some embodiments, said fibroblast growth factor (FGF) family member is keratinocyte growth factor. In some embodiments, said fibroblast growth factor (FGF) family member is keratinocyte growth factor FGF2, FGF8B, FGF10, or FGF21.

Pdx1 Expressing Pancreatic Progenitor Cells

In some aspects, the present disclosure provides a method of producing Pdx1 expressing pancreatic progenitor cells from a population of primitive gut tube cells comprising contacting a population of primitive gut tube cells with a composition that comprises at least one, two, three, four, five, six, or seven agents of a sonic-hedgehog (SHH) pathway inhibitor, a fibroblast growth factor (FGF) family member, a retinoic acid signaling pathway activator, a Rho-associated coiled-coil containing protein kinase (ROCK) inhibitor, a TGF-β signaling pathway activator, a bone morphogenetic protein (BMP) inhibitor, or a protein kinase C (PKC) activator, or any combination thereof.

In some embodiments, said sonic-hedgehog (SHH) pathway inhibitor is Sant 1. In some embodiments, said fibroblast growth factor (FGF) family member is keratinocyte growth factor. In some embodiments, said retinoic acid signaling pathway activator is retinoic acid. In some embodiments, said Rho-associated coiled-coil containing protein kinase (ROCK) inhibitor is Y27632 or thiazovivin. In some embodiments, said TGF-β signaling pathway activator is activin A. In some embodiments, said bone morphogenetic protein (BMP) inhibitor is DHM1. In some embodiments, said protein kinase C (PKC) activator is PDBU.

In some embodiments, said sonic-hedgehog (SHH) pathway inhibitor is Sant 1, Sant2, Sant 4, Sant4, Cur61414, forskolin, tomatidine, AY9944, triparanol, cyclopamine, or derivatives thereof.

In some embodiments, said fibroblast growth factor (FGF) family member is keratinocyte growth factor, FGF2, FGF8B, FGF10, or FGF21.

In some embodiments, said Rho-associated coiled-coil containing protein kinase (ROCK) inhibitor is Y27632, thiazovivin, N-[(15)-2-Hydroxy-1-phenylethyl]-iV-[4-(4-pyridinyl)phenyl]-urea (AS 1892802), fasudil hydrochloride (also known as HA 1077), −[3-[[2-(4-Amino-J,2,5-oxadiazol-3-yl)-1-ethyl-1H-imidazo[4,5-c]pyridin-6-yl]oxy]phenyl]-4-[2-(4-morpholinyl)ethoxy]benzamide (GS 269962), 4~[4-(Trifluoromethyl)phenyl]-N-(6-Fluoro-1H-indazol-5-yl)-2-methyl-6-oxo-1,4,5,6-tetrahydro-3-pyridinecarboxamide (GSK 429286), (5)-(+)-2-Methyl-1-[(4-methyl-5-isoquinolinyl)sulfonyl]-hexahydro-1H-1,4-diazepine dihydrochloride (H 1 152 dihydrochloride), (5)-(+)-4-Glycyl-2-methyl-1-[(4-methyl-5-isoquinolinyl)sulfonyl]-hexahydro-1H-1,4-diazepine dihydrochloride (glycyl-M 1 152 dihydrochloride), N-[(3-Hydroxyphenyl)methyl]-V-[4-(4-pyridinyl)-2-thiazolyl]urea dihydrochloride (RKI 1447 dihydrochloride), (35)-1-[[2-(4-Amino-1,2,5-oxadiazol-3-yl)-1-ethyl-1H-imidazo[4,5-c]pyridin-7-yl]carbonyl]-3-pyrrolidinamine dihydrochloride (SB772077B dihydrochloride), N-[2-[2-(Dimethylamino)ethoxyJ-4-(I H-pyrazol-4-yl)phenyl-2,3-dihydro-1,4-benzodioxin-2-carboxamide dihydrochloride (SR 3677 dihydrochloride), and tra«5 · -4-[(1/?)-1-Aminoethyl]-N-4-pyridinylcyclohexanecarboxamide dihydrochloride (Y-27632 dihydrochloride), N-Benzyl-[2-(pyrimidin-4-yl)amino]thiazole-4-carboxamide (Thiazovivin), Rock Inhibitor, a isoquinolinesulfonamide compound (Rho Kinase Inhibitor), N-(4-Pyridyl)-N'-(2,4,6-trichlorophenyl)urea (Rho Kinase Inhibitor II), 3-(4-Pyridyl)-1H-indole (Rho Kinase Inhibitor III, Rockout), and 4-pyrazoleboronic acid pinacol ester; a Rock antibody commercially available from Santa Cruz Biotechnology selected from the group consisting of Rock-1 (B1), Rock-1 (C-19), Rock-1 (H-11), Rock-1 (G-6), Rock-1 (H-85), Rock-1 (K-18), Rock-2 (C-20), Rock-2 (D-2), Rock-2 (D-11), Rock-2 (N-19), Rock-2 (H-85), Rock-2 (30-J); a ROCK CRISPR/Cas9 knockout plasmid selected from the group consisting of Rock-1 CRISPR/Cas9 KO plasmid (h), Rock-2 CRISPR/Cas9 KO plasmid (h), Rock-1 CRISPR/Cas9 KO plasmid (m), Rock-2 CRISPR/Cas9 KO plasmid (m); a ROCK siRNA, shRNA plasmid and/or shRNA lentiviral particle gene silencer selected from the group consisting of Rock-1 siRNA (h): sc-29473, Rock-1 siRNA (m): sc-36432, Rock-1 siRNA (r): sc-72179, Rock-2 siRNA (h): sc-29474, Rock-2 siRNA (m): sc-36433, or Rock-2 siRNA (r): sc-108088, or derivatives thereof.

In some embodiments, said TGF-β signaling pathway activator is activin A, GDF1, GDF11, Nodal, or TGFβ.

In some embodiments, said bone morphogenetic protein (BMP) inhibitor is DHM1 (4-[6-(4-Isopropoxyphenyl)pyrazolo[1,5-a]pyrimidin-3-yl]quinoline, 4-[6-[4-(1-Methylethoxy)phenyl]pyrazolo[1,5-a]pyrimidin-3-yl]-quinoline), ML347, SML1307, or SML0559.

In some embodiments, said protein kinase C (PKC) activator is Phorbol 12,13-dibutyrate (PDBU), enzastaurin, CHIR-98014, LY2157299, MK-0752, BMS-833923, avagacestat, RO4929097, DAPT (GSI-IX), hesperetin, tofacitinib, APTSTAT3-9R, SB216763, CHIR-99021, semagacestat, GF109203X, repSox, Go 6983, sotrastaurin, LGK-974, PD173955, Ro31-8220, AZD1080, LY411575, or YO-010207.

Nkx6.1 Expressing Pancreatic Progenitor Cells

In some aspects, the present disclosure provides a method of producing a NKX6.1-expressing pancreatic progenitor cell from a Pdx1-expressing pancreatic progenitor cell comprising contacting a population of cells comprising Pdx1-expressing pancreatic progenitor cells or precursors under conditions that promote cell clustering with at least two maturation factors comprising a) at least one growth factor from the fibroblast growth factor (FGF) family, b) a sonic hedgehog pathway inhibitor, and optionally c) a low concentration of a retinoic acid (RA) signaling pathway activator, for a period of at least five days to induce the differentiation of at least one Pdx1-positive pancreatic progenitor cell in the population into NKX6.1-expressing pancreatic progenitor cells, wherein the NKX6.1-expressing pancreatic progenitor cells express NKX6.1.

In some embodiments, NKX6.1-expressing pancreatic progenitor cells are differentiated from a population of Pdx1-expressing pancreatic progenitor cells by contacting said population of Pdx1-expressing pancreatic progenitor cells with a composition that comprises at least one, two, three, four, five, six, or seven agents of a fibroblast growth factor (FGF) family member, a sonic hedgehog antagonist, a Rho-associated coiled-coil containing protein kinase (ROCK) inhibitor, a TGF-β signaling pathway activator, a retinoic acid signaling pathway activator, a Wnt signaling inhibitor, or a protein kinase C activator, or any combination thereof.

In some embodiments, said fibroblast growth factor (FGF) family is keratinocyte growth factor. In some embodiments, said TGF-β signaling pathway activator is activin A. In some embodiments, said retinoic acid signaling pathway activator is retinoic acid. In some embodiments, said sonic hedgehog antagonist is Sant1. In some embodiments, said Rho-associated coiled-coil containing protein kinase (ROCK) inhibitor is Y27632 or thiazovivin. In some embodiments, the Wnt signaling inhibitor inhibits a tankyrase (e.g., tankyrase 1 or tankyrase 2). In some embodiments, said Wnt signaling inhibitor is AZ 6102, NVP-TNKS656, or IWR-1-endo. In some embodiments, said protein kinase C activator is PDBU.

In some embodiments, said fibroblast growth factor (FGF) family member is keratinocyte growth factor, FGF2, FGF8B, FGF10, or FGF21.

In some embodiments, said sonic hedgehog antagonist is Sant1, Sant2, Sant 4, Sant4, Cur61414, forskolin, tomatidine, AY9944, triparanol, cyclopamine, or derivatives thereof.

In some embodiments, said Rho-associated coiled-coil containing protein kinase (ROCK) inhibitor is Y27632, thiazovivin, N-[(1S)-2-Hydroxy-1-phenylethyl]-iV-[4-(4-pyridinyl)phenyl]-urea (AS 1892802), fasudil hydrochloride (also known as HA 1077), –[3-[[2-(4-Amino-J,2,5-oxadiazol-3-yl)-1-ethyl-1H-imidazo[4,5-c]pyridin-6-yl]oxy]phenyl]-4-[2-(4-morpholinyl)ethoxy]benzamide (GS 269962), 4-[4-(Trifluoromethyl)phenyl]-N-(6-Fluoro-1H-indazol-5-yl)-2-methyl-6-oxo-1,4,5,6-tetrahydro-3-pyridinecarboxamide (GSK 429286), (5)-(+)-2-Methyl-1-[(4-methyl-5-isoquinolinyl)sulfonyl]-hexahydro-1H-1,4-diazepine dihydrochloride (H 1 152 dihydrochloride), (5)-(+)-4-Glycyl-2-methyl-1-[(4-methyl-5-isoquinolinyl)sulfonyl]-hexahydro-1H-1,4-diazepine dihydrochloride (glycyl-M 1 152 dihydrochloride), N-[(3-Hydroxyphenyl)methyl]-V-[4-(4-pyridinyl)-2-thiazolyl]urea dihydrochloride (RKI 1447 dihydrochloride), (35)-1-[[2-(4-Amino-1,2,5-oxadiazol-3-yl)-1-ethyl-1H-imidazo[4,5-c]pyridin-7-yl]carbonyl]-3-pyrrolidinamine dihydrochloride (SB772077B dihydrochloride), N-[2-[2-(Dimethylamino)ethoxyJ-4-(1H-pyrazol-4-yl)phenyl-2,3-dihydro-1,4-benzodioxin-2-carboxamide dihydrochloride (SR 3677 dihydrochloride), and tra«5·-4-[(1/?)-1-Aminoethyl]-N-4-pyridinylcyclohexanecarboxamide dihydrochloride (Y-27632 dihydrochloride), N-Benzyl-[2-(pyrimidin-4-yl)amino]thiazole-4-carboxamide (Thiazovivin), Rock Inhibitor, a isoquinolinesulfonamide compound (Rho Kinase Inhibitor), N-(4-Pyridyl)-N'-(2,4,6-trichlorophenyl)urea (Rho Kinase Inhibitor II), 3-(4-Pyridyl)-1H-indole (Rho Kinase Inhibitor III, Rockout), and 4-pyrazoleboronic acid pinacol ester; a Rock antibody commercially available from Santa Cruz Biotechnology selected from the group consisting of Rock-1 (B1), Rock-1 (C-19), Rock-1 (H-11), Rock-1 (G-6), Rock-1 (H-85), Rock-1 (K-18), Rock-2 (C-20), Rock-2 (D-2), Rock-2 (D-11), Rock-2 (N-19), Rock-2 (H-85), Rock-2 (30-J); a ROCK CRISPR/Cas9 knockout plasmid selected from the group consisting of Rock-1 CRISPR/Cas9 KO plasmid (h), Rock-2 CRISPR/Cas9 KO plasmid (h), Rock-1 CRISPR/Cas9 KO plasmid (m), Rock-2 CRISPR/Cas9 KO plasmid (m); a ROCK siRNA, shRNA plasmid and/or shRNA lentiviral particle gene silencer selected from the group consisting of Rock-1 siRNA (h): sc-29473, Rock-1 siRNA (m): sc-36432, Rock-1 siRNA (r): sc-72179, Rock-2 siRNA (h): sc-29474, Rock-2 siRNA (m): sc-36433, or Rock-2 siRNA (r): sc-108088, or derivatives thereof.

In some embodiments, said TGF-β signaling pathway activator is activin A, GDF1, GDF11, Nodal, or TGFβ.

In some embodiments, said Wnt signaling inhibitor is AZ 6102, JW55, MN64, IWR-1-endo, TC-E5001, WIKI4, TNKS 22, TNKS 49, 2X-121 (E7449), XAV-939, G007-LK, NVP-TNKS656, decernotinib, (VX-509), vismodegib (GDC-0449), IM-12, GSK429286A, INO-1001, Ofloxacin, TG101209, FG-4592, I-BET-762, LY2157299, MK-0752, Wnt-C59 (C59), MC1568, Pacritinib (SB1518), SB415286, Drocinostat, IWR-1-endo, Norfloxacin, SH-4-54, Nexturastat A, SB216763, UNC0.79, dephnetin, GF109203X, RepSox, Sotrastaurin, SB431542, tofacitinib (CP-690550, Tasocitinib), AG-14361, CI994 (tacedinaline), Ro 31-8220 mesylate, resveratrol, NVP-TNKS656, or YO-01027.

In some embodiments, said protein kinase C activator is Phorbol 12,13-dibutyrate (PDBU), enzastaurin, CHIR-98014, LY2157299, MK-0752, BMS-833923, avagacestat, RO4929097, DAPT (GSI-IX), hesperetin, tofacitinib, APT-STAT3-9R, SB216763, CHIR-99021, semagacestat, GF109203X, repSox, Go 6983, sotrastaurin, LGK-974, PD173955, Ro31-8220, AZD1080, LY411575, or YO-010207.

In some embodiments, at least 10% of the Pdx1-expressing pancreatic progenitor cells in the population are induced to differentiate into NKX6-1-expressing pancreatic progenitor cells. In some embodiments, at least 95% of the Pdx1-expressing pancreatic progenitor cells in the population are induced to differentiate into NKX6.1-expressing pancreatic progenitor cells. In some embodiments, the NKX6.1-expressing pancreatic progenitor cells express Pdx1, NKX6.1, and FoxA2. In some embodiments, the Pdx1-expressing pancreatic progenitor cells are produced from a population of pluripotent stem cells selected from the group consisting of embryonic stem cells and induced pluripotent stem cells.

Pancreatic Endocrine Progenitor Cells

In some aspects, the present disclosure provides a method of producing pancreatic endocrine progenitor cells from a population of Pdx1 expressing, NKX6.1 expressing pancreatic progenitor cells comprising contacting a population of cells comprising contacting said Pdx1 expressing, NKX6.1 expressing pancreatic progenitor cells with a composition that comprises at least one, two, three, four, five, six, seven eight, nine, ten, eleven, or twelve agents of a transforming growth factor β (TGF-β) signaling pathway inhibitor, a thyroid hormone (TH) signaling pathway activator, a sonic-hedgehog (SHH) pathway inhibitor, a retinoic acid (RA) signaling pathway activator, a γ-secretase inhibitor, a bone morphogenic protein (BMP) signaling pathway inhibitor, an inhibitor of Rho-associated, coiled-coil containing protein kinase (ROCK), a growth factor from epidermal growth factor (EGF) family, a broad kinase inhibitor, a histone methylation inhibitor, or a Wnt signaling pathway inhibitor, or a protein kinase C activator, any combination thereof.

In some embodiments, said transforming growth factor β (TGF-β) signaling pathway inhibitor is Alk5i (SB505124). In some embodiments, said thyroid hormone (TH) signaling pathway activator is triiodothyronine (T3) or GC-1. In some embodiments, said sonic-hedgehog (SHH) pathway inhibitor is Sant 1. In some embodiments, said retinoic acid (RA) signaling pathway activator is retinoic acid. In some embodiments, said γ-secretase inhibitor is XXI. In some embodiments, said bone morphogenic protein (BMP) signaling pathway inhibitor is LDN193189. In some embodiments, said inhibitor of Rho-associated, coiled-coil containing protein kinase (ROCK) is Y27632 or thiazovivin. In some embodiments, said growth factor from epidermal growth factor (EGF) family is betacellulin. In some embodiments, said a broad kinase inhibitor is Staurosporine (SSP). In some embodiments, said a histone methylation inhibitor is Dznep (3-deazaneplanocin A). In some embodiments, the Wnt signaling inhibitor inhibits a tankyrase (e.g., tankyrase 1 or tankyrase 2). In some embodiments, the Wnt signaling inhibitor is AZ 6102, NVP-TNKS656, or IWR-1-endo. In some embodiments, said protein kinase C activator is PDBU.

In some embodiments, said transforming growth factor β (TGF-β) signaling pathway inhibitor is ALK5 inhibitor II (CAS 446859-33-2, an ATP-competitive inhibitor of TGF-B Ri kinase, also known as RepSox, IIJPAC Name: 2-[5-(6-methylpyridin-2-yl)-1H-pyrazol-4-yl]-1,5-naphthyridine, an analog or derivative of ALK5 inhibitor II, such as an analog or derivative of ALK5 inhibitor II described in U.S. Pub. No. 2012/0021519, a TGF-β receptor inhibitor described in U.S. Pub. No. 2010/0267731, an ALK5 inhibitor described in U.S. Pub Nos. 2009/0186076 and 2007/0142376, including e.g., A83-01, 431542, D4476, GW788388, LY364947, LY580276, SB525334, SB505124, SD208, GW6604, or GW788388.

In some embodiments, said thyroid hormone (TH) signaling pathway activator is triiodothyronine (T3), GC-1, an analog or derivative of T3, for example, selective and non-selective thyromimetics, TRJ selective agonist-GC-1, GC-24,4-Hydroxy-PCB 106, MB0781 1, MB07344,3,5-diiodothyropropionic acid (DITPA); the selective TR-β agonist GC-1; 3-Iodothyronamine (T(1)AM) and 3,3',5-triiodothyroacetic acid (Triac) (bioactive metabolites of the hormone thyroxine (T(4)); KB-21 15 and KB-141; thyronamines; SKF L-94901; DIBIT; 3'-AC-T2; tetraiodothyroacetic acid (Tetrac) and triiodothyroacetic acid (Triac) (via oxidative deamination and decarboxylation of thyroxine [T4] and triiodothyronine [T3] alanine chain), 3,3',5'-triiodothyronine (rT3) (via T4 and T3 deiodination), 3,3'-diiodothyronine (3,3'-T2) and 3,5-diiodothyronine (T2) (via T4, T3, and rT3 deiodination), and 3-iodothyronamine (T1AM) and thyronamine (T0AM) (via T4 and T3 deiodination and amino acid decarboxylation), as well as for TH structural analogs, such as 3,5,3'-triiodothyropropionic acid (Triprop), 3,5-dibromo-3-pyridazinone-1-thyronine (L-940901), N-[3,5-dimethyl-4-(4'-hydroxy-3 f-isopropylphenoxy)-phenyl]-oxamic acid (CGS 23425), 3,5-dimethyl-4-[(4'-hydroxy-3'-isopropylbenzyl)-phenoxy]acetic acid (GC-1), 3,5-dichloro-4-[(4-hydroxy-3-isopropylphenoxy)phenyl]acetic acid (KB-141), or 3,5-diiodothyropropionic acid (DITPA).

In some embodiments, said sonic-hedgehog (SHH) pathway inhibitor is Sant1, Sant2, Sant 4, Sant4, Cur61414, forskolin, tomatidine, AY9944, triparanol, cyclopamine, or derivatives thereof).

In some embodiments, said retinoic acid (RA) signaling pathway activator is retinoic acid, In some embodiments, said γ-secretase inhibitor is XXI, DAPT (GSI-IX), RO4929097, Semagacestat (LY450139), Avagacestat (BMS-708163), Dibenzazepine (YO-01027), LY411575, IMR-1, or L-685,458.

In some embodiments, said bone morphogenic protein (BMP) signaling pathway inhibitor is LDN193189, 4-[6-(4-piperazin-1-ylphenyl)pyrazol o [1,5-a]pyrimidin-3-yl]quinolone (LDN 193 189; also known as LDN1931 89, 1062368-24-4, LDN-193189, DM 3189, DM-3189, and referred to herein as LDN), an analog or derivative of LDN193189, e.g., a salt (e.g., LDN193189 hydrochloride), hydrate, solvent, ester, or prodrug of LDN193189, or a compound of Formula I from U.S. Patent Publication No. 2011/0053930.

In some embodiments, said inhibitor of Rho-associated, coiled-coil containing protein kinase (ROCK) is Y27632, thiazovivin, N-[(15)-2-Hydroxy-1-phenylethyl]-iV-[4-(4-pyridinyl)phenyl]-urea (AS 1892802), fasudil hydrochloride (also known as HA 1077), −[3-[[2-(4-Amino-J,2,5-oxadiazol-3-yl)-1-ethyl-1H-imidazo[4,5-c]pyridin-6-yl]oxy]phenyl]-4-[2-(4-morpholinyl)ethoxy]benzamide (GS 269962), 4~[4-(Trifluoromethyl)phenyl]-N-(6-Fluoro-1H-indazol-5-yl)-2-methyl-6-oxo-1,4,5,6-tetrahydro-3-pyridinecarboxamide (GSK 429286), (5)-(+)-2-Methyl-1-[(4-methyl-5-isoquinolinyl)sulfonyl]-hexahydro-1H-1,4-diazepine dihydrochloride (H 1 152 dihydrochloride), (5)-(+)-4-Glycyl-2-methyl-1-[(4-methyl-5-isoquinolinyl)sulfonyl]-hexahydro-1H-1,4-diazepine dihydrochloride (glycyl-M 1 152 dihydrochloride), N-[(3-Hydroxyphenyl)methyl]-V-[4-(4-pyridinyl)-2-thiazolyl]urea dihydrochloride (RKI 1447 dihydrochloride), (35)-1-[[2-(4-Amino-1,2,5-oxadiazol-3-yl)-1-ethyl-1H-imidazo[4,5-c]pyridin-7-yl]carbonyl]-3-pyrrolidinamine dihydrochloride (SB772077B dihydrochloride), N-[2-[2-(Dimethylamino)ethoxyJ-4-(1H-pyrazol-4-yl)phenyl-2,3-dihydro-1,4-benzodioxin-2-carboxamide dihydrochloride (SR 3677 dihydrochloride), and tra«5·-4-[(1/?)-1-Aminoethyl]-N-4-pyridinylcyclohexanecarboxamide dihydrochloride (Y-27632 dihydrochloride), N-Benzyl-[2-(pyrimidin-4-yl)amino]thiazole-4-carboxamide (Thiazovivin), Rock Inhibitor, a isoquinolinesulfonamide compound (Rho Kinase Inhibitor), N-(4-Pyridyl)-N'-(2,4,6-trichlorophenyl)urea (Rho Kinase Inhibitor II), 3-(4-Pyridyl)-1H-indole (Rho Kinase Inhibitor III, Rockout), and 4-pyrazoleboronic acid pinacol ester; a Rock antibody commercially available from Santa Cruz Biotechnology selected from the group consisting of Rock-1 (B1), Rock-1 (C-19), Rock-1 (H-11), Rock-1 (G-6), Rock-1 (H-85), Rock-1 (K-18), Rock-2 (C-20), Rock-2 (D-2), Rock-2 (D-11), Rock-2 (N-19), Rock-2 (H-85), Rock-2 (30-J); a ROCK CRISPR/Cas9 knockout plasmid selected from the group consisting of Rock-1 CRISPR/Cas9 KO plasmid (h), Rock-2 CRISPR/Cas9 KO plasmid (h), Rock-1 CRISPR/Cas9 KO plasmid (m), Rock-2 CRISPR/Cas9 KO plasmid (m); a ROCK siRNA, shRNA plasmid and/or shRNA lentiviral particle gene silencer selected from the group consisting of Rock-1 siRNA (h): sc-29473, Rock-1 siRNA (m): sc-36432, Rock-1 siRNA (r): sc-72179, Rock-2 siRNA (h): sc-29474, Rock-2 siRNA (m): sc-36433, or Rock-2 siRNA (r): sc-108088.

In some embodiments, said growth factor from epidermal growth factor (EGF) family is betacellulin, heparin-binding EGF-like growth factor (HB-EGF), transforming growth factor-α (TGF-α), amphiregulin (AR), epiregulin (EPR), epigen, neuregulin-1 (NRG1), neuregulin-2 (NRG2), neuregulin-3 (NRG3), or neuregulin-4 (NRG4).

In some embodiments, said a broad kinase inhibitor is Staurosporine (SSP), an analog of staurosporine, such as Ro-31-8220, a bisindolylmaleimide (Bis) compound, 1 0'-{5"-[(methoxycarbonyl)amino]-2"-methyl}-phenylaminocarbonylstaurosporine, a staralog, or cgp41251.

In some embodiments, said a histone methylation inhibitor is 3-Deazaneplanocin A hydrochloride (DZNep-(1S,2R,5R)-5-(4-amino-1H-imidazo[4,5-c]pyridin-1-yl)-3-(hydroxymethyl)cyclopent-3-ene-1,2-diol); Bix-01294, UNC0638, BRDD4770, EPZ004777, AZ505, PDB4e47, alproic acid, vorinostat, romidepsin, entinostat abexinostat, givinostat, and mocetinostat, butyrate, or a serine protease inhibitor (serpin) family member.

In some embodiments, said Wnt signaling inhibitor is AZ 6102, JW55, MN64, IWR-1-endo, TC-E5001, WIKI4, TNKS 22, TNKS 49, 2X-121 (E7449), XAV-939, G007-LK, NVP-TNKS656, decernotinib, (VX-509), vismodegib (GDC-0449), IM-12, GSK429286A, INO-1001, Ofloxacin, TG101209, FG-4592, I-BET-762, LY2157299, MK-0752, Wnt-C59 (C59), MC1568, Pacritinib (SB1518), SB415286, Drocinostat, IWR-1-endo, Norfloxacin, SH-4-54, Nexturastat A, SB216763, UNC0.79, dephnetin, GF109203X, RepSox, Sotrastaurin, SB431542, tofacitinib (CP-690550, Tasocitinib), AG-14361, CI994 (tacedinaline), Ro 31-8220 mesylate, resveratrol, NVP-TNKS656, or YO-01027.

In some embodiments, said protein kinase C activator is Phorbol 12,13-dibutyrate (PDBU), enzastaurin, CHIR-98014, LY2157299, MK-0752, BMS-833923, avagacestat, RO4929097, DAPT (GSI-IX), hesperetin, tofacitinib, APT-STAT3-9R, SB216763, CHIR-99021, semagacestat, GF109203X, repSox, Go 6983, sotrastaurin, LGK-974, PD173955, Ro31-8220, AZD1080, LY411575, or YO-010207.

In some embodiments, pancreatic endocrine progenitor cells are packaged into a device and said device is implanted into a human for treatment of diabetes. In some embodiments, said pancreatic endocrine progenitor cells mature in vivo into mature β cells that exhibit glucose stimulated insulin secretion (GSIS). In some embodiments, said pancreatic endocrine progenitor cells are genetically modified. In some embodiments, said pancreatic endocrine progenitor cells comprise a genomic disruption in at least one gene sequence, wherein said disruption reduces or eliminates expression of a protein encoded by said gene sequence. In some embodiments, said at least one gene sequence encodes an MHC-Class I gene. In some embodiments, said MHC-Class I gene encodes beta-2 microglobulin (B2M), HLA-A, HLA-B, or HLA-C. In some embodiments, said cells comprise a genomic disruption in a natural killer cell activating ligand gene. In some embodiments, said natural killer cell activating ligand gene encodes intercellular adhesion molecule 1 (ICAM1), CD58, CD155, carcinoembryonic antigen-related cell adhesion molecule 1 (CEACAM1), cell adhesion molecule 1 (CADM1), MHC-Class I polypeptide-related sequence A (MICA), or MHC-Class I polypeptide-related sequence B (MICB).

Stem Cells Derived β Cells (SC-β Cells)

Provided herein are methods of using stem cells for producing SC-beta cells (e.g., mature pancreatic β cells or β-like cells (e.g., Pdx1 expressing, NKX6.1 expressing β cells)) or precursors thereof. In an embodiment, germ cells may be used in place of, or with, the stem cells to provide at least one SC-1β cell, using similar protocols as described in U.S. Patent Application Publication No. US20150240212 and US20150218522, each of which is herein incorporated by reference in its entirety. Suitable germ cells can be prepared, for example, from primordial germ cells present in human fetal material taken about 8-11 weeks after the last menstrual period. Illustrative germ cell preparation methods are described, for example, in Shamblott et al., Proc. Natl. Acad. Sci. USA 95:13726, 1998 and U.S. Pat. No. 6,090,622.

Provided herein are compositions and methods of generating SC-β cells (e.g., pancreatic β cells). Generally, the at least one SC-β cell or precursor thereof, e.g., pancreatic progenitors produced according to the methods disclosed herein can comprise a mixture or combination of different cells, e.g., for example a mixture of cells such as a Pdx1-positive pancreatic progenitors, pancreatic progenitors co-expressing Pdx1 and NKX6.1, a Ngn3-positive endocrine progenitor cell, an insulin-positive endocrine cell (e.g., a β-like cell), and an insulin-positive endocrine cell, and/or other pluripotent or stem cells.

The at least one SC-β cell or precursor thereof can be produced according to any suitable culturing protocol to differentiate a stem cell or pluripotent cell to a desired stage of differentiation. In some embodiments, the at least one SC-β cell or the precursor thereof are produced by culturing at least one pluripotent cell for a period of time and under conditions suitable for the at least one pluripotent cell to differentiate into the at least one SC-β cell or the precursor thereof.

In some embodiments, the at least one SC-β cell or precursor thereof is a substantially pure population of SC-β cells or precursors thereof. In some embodiments, a population of SC-β cells or precursors thereof comprises a mixture of pluripotent cells or differentiated cells. In some embodiments, a population SC-β cells or precursors thereof are substantially free or devoid of embryonic stem cells or pluripotent cells or iPS cells.

In some embodiments, a somatic cell, e.g., fibroblast can be isolated from a subject, for example as a tissue biopsy, such as, for example, a skin biopsy, and reprogrammed into an induced pluripotent stem cell for further differentiation to produce the at least one SC-β cell or precursor thereof for use in the compositions and methods described herein. In some embodiments, a somatic cell, e.g., fibroblast is maintained in culture by methods known by one of ordinary skill in the art, and in some embodiments, propagated prior to being converted into SC-β cells by the methods as disclosed herein.

In some embodiments, the at least one SC-β cell or precursor thereof are maintained in culture by methods known by one of ordinary skill in the art, and in some embodiments, propagated prior to being converted into SC-β cells by the methods as disclosed herein.

Further, at least one SC-β cell or precursor thereof, e.g., pancreatic progenitor can be from any mammalian species, with non-limiting examples including a murine, bovine, simian, porcine, equine, ovine, or human cell. For clarity and simplicity, the description of the methods herein refers to a mammalian at least one SC-β cell or precursor thereof but it should be understood that all of the methods described herein can be readily applied to other cell types of at least one SC-β cell or precursor thereof. In some embodiments, the at least one SC-β cell or precursor thereof is derived from a human individual.

In some aspects, the present disclosure provides a method of producing SC-β cells from a population of pancreatic endocrine progenitor cells. In some embodiments, pancreatic endocrine progenitor cells are cryopreserved and thawed prior to differentiation into SC-β cells. In some embodiments, clusters of pancreatic endocrine progenitor cells are dispersed, cryopreserved, and reaggregated prior to differentiation into SC-β cells. In some embodiments, said cryopreserved pancreatic endocrine progenitor cells are thawed in a composition that comprises at least one, two, three, four, five, or six agents of a transforming growth factor β (TGF-β) signaling pathway inhibitor, a thyroid hormone (TH) signaling pathway activator, a sonic-hedgehog (SHH) pathway inhibitor, a retinoic acid (RA) signaling pathway activator, a γ-secretase inhibitor, a bone morphogenic protein (BMP) signaling pathway inhibitor, an inhibitor of Rho-associated, coiled-coil containing protein kinase (ROCK), a growth factor from epidermal growth factor (EGF) family, a broad kinase inhibitor, a histone methylation inhibitor, or an MGLL inhibitor, or any combination thereof.

In some embodiments, said transforming growth factor β (TGF-β) signaling pathway inhibitor is Alk5i (SB505124). In some embodiments, said thyroid hormone (TH) signaling pathway activator is triiodothyronine (T3) or GC-1. In some embodiments, said sonic-hedgehog (SHH) pathway inhibitor is Sant 1. In some embodiments, said retinoic acid (RA) signaling pathway activator is retinoic acid. In some embodiments, said γ-secretase inhibitor is XXI. In some embodiments, said bone morphogenic protein (BMP) signaling pathway inhibitor is LDN193189. In some embodiments, said inhibitor of Rho-associated, coiled-coil containing protein kinase (ROCK) is Y27632 or thiazovivin. In some embodiments, said growth factor from epidermal growth factor (EGF) family is betacellulin. In some embodiments, said a broad kinase inhibitor is Staurosporine (SSP). In some embodiments, said a histone methylation inhibitor is Dznep (3-deazaneplanocin A).

In some embodiments, said transforming growth factor β (TGF-β) signaling pathway inhibitor is ALK5 inhibitor II (CAS 446859-33-2, an ATP-competitive inhibitor of TGF-B Ri kinase, also known as RepSox, IIJPAC Name: 2-[5-(6-methylpyridin-2-yl)-1H-pyrazol-4-yl]-1,5-naphthyridine, an analog or derivative of ALK5 inhibitor II, such as an analog or derivative of ALK5 inhibitor II described in U.S. Pub. No. 2012/0021519, a TGF-β receptor inhibitor described in U.S. Pub. No. 2010/0267731, an ALK5 inhibitor described in U.S. Pub Nos. 2009/0186076 and 2007/0142376, including e.g., A83-01, 431542, D4476, GW788388, LY364947, LY580276, SB525334, SB505124, SD208, GW6604, or GW788388.

In some embodiments, said thyroid hormone (TH) signaling pathway activator is triiodothyronine (T3), GC-1, an analog or derivative of T3, for example, selective and non-selective thyromimetics, TRJ selective agonist-GC-1, GC-24,4-Hydroxy-PCB 106, MB0781 1, MB07344,3,5-diiodothyropropionic acid (DITPA); the selective TR-β agonist GC-1; 3-Iodothyronamine (T(1)AM) and 3,3',5-triiodothyroacetic acid (Triac) (bioactive metabolites of the hormone thyroxine (T(4)); KB-21 15 and KB-141; thyronamines; SKF L-94901; DIBIT; 3'-AC-T2; tetraiodothyroacetic acid (Tetrac) and triiodothyroacetic acid (Triac) (via oxidative deamination and decarboxylation of thyroxine [T4] and triiodothyronine [T3] alanine chain), 3,3',5'-triiodothyronine (rT3) (via T4 and T3 deiodination), 3,3'-diiodothyronine (3,3'-T2) and 3,5-diiodothyronine (T2) (via T4, T3, and rT3 deiodination), and 3-iodothyronamine (T1AM) and thyronamine (T0AM) (via T4 and T3 deiodination and amino acid decarboxylation), as well as for TH structural analogs, such as 3,5,3'-triiodothyropropionic acid (Triprop), 3,5-dibromo-3-pyridazinone-1-thyronine (L-940901), N-[3,5-dimethyl-4-(4'-hydroxy-3 f-isopropylphenoxy)-phenyl]-oxamic acid (CGS 23425), 3,5-dimethyl-4-[(4'-hydroxy-3'-isopropylbenzyl)-phenoxy]acetic acid (GC-1), 3,5-dichloro-4-[(4-hydroxy-3-isopropylphenoxy)phenyl]acetic acid (KB-141), or 3,5-diiodothyropropionic acid (DITPA).

In some embodiments, said sonic-hedgehog (SHH) pathway inhibitor is Sant1, Sant2, Sant 4, Sant4, Cur61414, forskolin, tomatidine, AY9944, triparanol, cyclopamine, or derivatives thereof).

In some embodiments, said retinoic acid (RA) signaling pathway activator is retinoic acid, In some embodiments, said γ-secretase inhibitor is XXI, DAPT (GSI-IX), RO4929097, Semagacestat (LY450139), Avagacestat (BMS-708163), Dibenzazepine (YO-01027), LY411575, IMR-1, or L-685,458.

In some embodiments, said bone morphogenic protein (BMP) signaling pathway inhibitor is LDN193189, 4-[6-(4-piperazin-1-ylphenyl)pyrazol o [1,5-a]pyrimidin-3-yl]quinolone (LDN 193 189; also known as LDN1931 89, 1062368-24-4, LDN-193189, DM 3189, DM-3189, and referred to herein as LDN), an analog or derivative of LDN193189, e.g., a salt (e.g., LDN193189 hydrochloride), hydrate, solvent, ester, or prodrug of LDN193189, or a compound of Formula I from U.S. Patent Publication No. 2011/0053930.

In some embodiments, said inhibitor of Rho-associated, coiled-coil containing protein kinase (ROCK) is Y27632, thiazovivin, N-[(15)-2-Hydroxy-1-phenylethyl]-iV-[4-(4-pyridinyl)phenyl]-urea (AS 1892802), fasudil hydrochloride (also known as HA 1077), –[3-[[2-(4-Amino-J,2,5-oxadiazol-3-yl)-1-ethyl-1H-imidazo[4,5-c]pyridin-6-yl]oxy]phenyl]-4-[2-(4-morpholinyl)ethoxy]benzamide (GS 269962), 4~[4-(Trifluoromethyl)phenyl]-N-(6-Fluoro-1H-indazol-5-yl)-2-methyl-6-oxo-1,4,5,6-tetrahydro-3-pyridinecarboxamide (GSK 429286), (5)-(+)-2-Methyl-1-[(4-methyl-5-isoquinolinyl)sulfonyl]-hexahydro-1H-1,4-diazepine dihydrochloride (H 1 152 dihydrochloride), (5)-(+)-4-Glycyl-2-methyl-1-[(4-methyl-5-isoquinolinyl)sulfonyl]-hexahydro-1H-1,4-diazepine dihydrochloride (glycyl-M 1 152 dihydrochloride), N-[(3-Hydroxyphenyl)methyl]-V-[4-(4-pyridinyl)-2-thiazolyl]urea dihydrochloride (RKI 1447 dihydrochloride), (35)-1-[[2-(4-Amino-1,2,5-oxadiazol-3-yl)-1-ethyl-1H-imidazo[4,5-c]pyridin-7-yl]carbonyl]-3-pyrrolidinamine dihydrochloride (SB772077B dihydrochloride), N-[2-[2-(Dimethylamino)ethoxyJ-4-(1H-pyrazol-4-yl)phenyl-2,3-dihydro-1,4-benzodioxin-2-carboxamide dihydrochloride (SR 3677 dihydrochloride), and tra«5 · -4-[(1/?)-1-Aminoethyl]-N-4-pyridinylcyclohexanecarboxamide dihydrochloride (Y-27632 dihydrochloride), N-Benzyl-[2-(pyrimidin-4-yl)amino]thiazole-4-carboxamide (Thiazovivin), Rock Inhibitor, a isoquinolinesulfonamide compound (Rho Kinase Inhibitor), N-(4-Pyridyl)-N'-(2,4,6-trichlorophenyl)urea (Rho Kinase Inhibitor II), 3-(4-Pyridyl)-1H-indole (Rho Kinase Inhibitor III, Rockout), and 4-pyrazoleboronic acid pinacol ester; a Rock antibody commercially available from Santa Cruz Biotechnology selected from the group consisting of Rock-1 (B1), Rock-1 (C-19), Rock-1 (H-11), Rock-1 (G-6), Rock-1 (H-85), Rock-1 (K-18), Rock-2 (C-20), Rock-2 (D-2), Rock-2 (D-11), Rock-2 (N-19), Rock-2 (H-85), Rock-2 (30-J); a ROCK CRISPR/Cas9 knockout plasmid selected from the group consisting of Rock-1 CRISPR/Cas9 KO plasmid (h), Rock-2 CRISPR/Cas9 KO plasmid (h), Rock-1 CRISPR/Cas9 KO plasmid (m), Rock-2 CRISPR/Cas9 KO plasmid (m); a ROCK siRNA, shRNA plasmid and/or shRNA lentiviral particle gene silencer selected from the group consisting of Rock-1 siRNA (h): sc-29473, Rock-1 siRNA (m): sc-36432, Rock-1 siRNA (r): sc-72179, Rock-2 siRNA (h): sc-29474, Rock-2 siRNA (m): sc-36433, or Rock-2 siRNA (r): sc-108088.

In some embodiments, said growth factor from epidermal growth factor (EGF) family is betacellulin, heparin-binding EGF-like growth factor (HB-EGF), transforming growth factor-α (TGF-α), amphiregulin (AR), epiregulin (EPR), epigen, neuregulin-1 (NRG1), neuregulin-2 (NRG2), neuregulin-3 (NRG3), or neuregulin-4 (NRG4).

In some embodiments, said a broad kinase inhibitor is Staurosporine (SSP), an analog of staurosporine, such as Ro-31-8220, a bisindolylmaleimide (Bis) compound, 1 0'-{5"-[(methoxycarbonyl)amino]-2"-methyl}-phenylaminocarbonylstaurosporine, a staralog, or cgp41251.

In some embodiments, said a histone methylation inhibitor is 3-Deazaneplanocin A hydrochloride (DZNep-(1S,2R,5R)-5-(4-amino-1H-imidazo[4,5-c]pyridin-1-yl)-3-(hydroxymethyl)cyclopent-3-ene-1,2-diol); Bix-01294, UNC0638, BRDD4770, EPZ004777, AZ505, PDB4e47, alproic acid, vorinostat, romidepsin, entinostat abexinostat, givinostat, and mocetinostat, butyrate, or a serine protease inhibitor (serpin) family member.

In some embodiments, said MGLL inhibitor is JJKK048, KML29, NF1819, JW642, JZL184, JZL195, JZP361, pristimerin, or URB602.

In some embodiments, SC-β cells are packaged into a device and said device is implanted into a human for treatment of diabetes. In some embodiments, said SC-β cells are genetically modified. In some embodiments, said SC-pi cells comprise a genomic disruption in at least one gene sequence, wherein said disruption reduces or eliminates expression of a protein encoded by said gene sequence. In some embodiments, said at least one gene sequence encodes an MHC-Class I gene. In some embodiments, said MHC-Class I gene encodes beta-2 microglobulin (B2M), HLA-A, HLA-B, or HLA-C. In some embodiments, said cells comprise a genomic disruption in a natural killer cell activating ligand gene. In some embodiments, said natural killer cell activating ligand gene encodes intercellular adhesion molecule 1 (ICAM1), CD58, CD155, carcinoembryonic antigen-related cell adhesion molecule 1 (CEACAM1), cell adhesion molecule 1 (CADM1), MHC-Class I polypeptide-related sequence A (MICA), or MHC-Class I polypeptide-related sequence B (MICB).

Devices

Provided herein are devices suitable for implantation into a human subject comprising SC-β cells described herein or a precursor thereof, e.g., pancreatic endocrine progenitor cells; PDX1 expressing NKX6.1 expressing pancreatic progenitor cells; or PDX1 expressing pancreatic progenitor cells, or any combination thereof. In some embodiments, the device comprises SC-β cells that exhibit glucose stimulated insulin secretion (GSIS) in vitro or in vivo or both. In some embodiments, the device comprises pancreatic endocrine progenitor cells. In some embodiments, the device comprises PDX1 expressing NKX6.1 expressing pancreatic progenitor cells. In some embodiments, the device comprises PDX1 expressing pancreatic progenitor cells. In some embodiments, the device comprises pancreatic endocrine progenitor cells that are matured in vivo into β cells that exhibit glucose stimulated insulin secretion (GSIS) in vitro or in vivo or both. In some embodiments, the device comprises PDX1 expressing NKX6.1 expressing pancreatic progenitor cells that exhibit glucose stimulated insulin secretion (GSIS) in vitro or in vivo or both. In some embodiments, the device comprises PDX1 expressing pancreatic progenitor cells that exhibit glucose stimulated insulin secretion (GSIS) in vitro or in vivo or both.

Provided herein are compositions comprising insulin producing cells and a device housing said insulin producing cells, wherein said device upon implantation in an individual releases insulin while retaining the insulin producing cells in the device, and facilitates tissue vascularization in and around the device. In some embodiments, individual is not administered an immune suppression agent during the implantation or vascularization of the device. In some embodiments, the device comprises 1 million to 1 billion insulin producing cells. In some embodiments, the device has a thickness of at least about 300 µm. In some embodiments, the device comprises a membrane comprising a plurality of nodes interconnected by a plurality of fibrils.

In some embodiments, the device comprises a first membrane having a first surface comprising a plurality of channels, and a plurality of second surfaces opposing the first surface; and a second membrane opposite and attached to the plurality of second surfaces of the first membrane; wherein the first membrane and the second membrane form an enclosed compartment having a surface area to volume ratio of at least about 40 cm-1, and wherein the enclosed compartment provides a volume for housing a cell within the device.

In some embodiments, the compartment comprises a single continuous open chamber. In some embodiments, the volume is about 8 uL to about 1,000 uL. In some embodiments, the device has at least one of a length and a width of about 0.25 cm to about 3 cm. In some embodiments, the device has a thickness of at least about 300 µm. In some embodiments, the plurality of channels is generally perpendicular with respect to the first membrane. In some embodiments, the plurality of channels is arranged in a rectilinear array. In some embodiments, the plurality of channels is arranged in a polar array. In some embodiments, the channel has an average diameter of about 400 µm to about 3,000 µm. In some embodiments, the diameter is measured at a narrowest point in the channel. In some embodiments, a center of each channel is separated from the center of another channel by a distance of about 75 µm to about 500 µm. In some embodiments, the channel has a height to diameter ratio of at least about 0.2. In some embodiments, the device has a number of channels per area along a transverse plane, and in some cases the number is greater than about 50/cm2. In some embodiments, at least one of the first membrane and the second membrane comprise a plurality of nodes interconnected by a plurality of fibrils. In some embodiments, at least one of the first membrane and the second membrane comprise PVDF, PTFE, ePTFE, PCL, PE/PES, PP, PS, PMMA, PLGA, PLLA, or any combination thereof. In some embodiments, the device further comprises an opening through the first membrane and/or the second membrane within the channel. In some embodiments, the opening has a concentricity with respect to the channel of at most about 25% the diameter of the channel. In some embodiments is a frame configured to receive the device described herein. In some embodiments, the frame is configured to receive a plurality of cell housing devices. In some embodiments, the frame comprises a flexing mechanism configured to prevent buckling of the cell housing device. In some embodiments, the device further comprises a cell population. In some embodiments, the cell population is an insulin secreting cell population. In some embodiments, the cell population comprises at least one cell derived from a stem cell. In some embodiments, at least one cell is a genetically modified cell. In some cases, at least one cell is genetically engineered to reduce an immune response in a subject upon implantation of the device, as compared to comparable cells that are not genetically engineered. In some embodiments, the cell population is a stem cell derived cell that is capable of glucose-stimulated insulin secretion (GSIS). In some embodiments, the device further comprises a coating comprising a hydrophilic polymer. In some embodiments, the device has an insulin diffusion coefficient of about $2\times10^{\wedge}-6$ cm$^2$/s to about $1\times10^{\wedge}-5$ cm$^2$/s. In some embodiments, the device has a maximum insulin diffusion distance of less than about 150 μm. In some embodiments, the first membrane and the second membrane are fused with a fusion peel force of at least about 0.4 N.

In some embodiments, the device comprises apertures that allow for vascularization of the device in vivo. In some embodiments, the apertures have a diameter from about 100-500 microns, 100-400 microns, 100-350 microns, 100-300 microns, 100-200 microns, 200-500 microns, 200-400 microns, 200-350 microns, 200-300 microns, 300-500 microns, 300-400 microns, 300-350 microns, or 400-500 microns. In some embodiments, the apertures have a diameter of about 100 microns, 200 microns, 300 microns, 400 microns, or 500 microns. In some embodiments, the apertures have a diameter of at least 100 microns, 150 microns, 200 microns, 250 microns, 300 microns, 350 microns, 400 microns, 450 microns, or 500 microns. In some embodiments, the apertures have a diameter of no greater than 100 microns, 150 microns, 200 microns, 250 microns, 300 microns, 350 microns, 400 microns, 450 microns, or 500 microns. In some embodiments, the apertures have a diameter of about 320 microns.

In some embodiments, the apertures are spaces such that the distance from the center of one aperture to the center of the adjacent aperture is from about 300 μm-2,000 μm, 400 μm-2,000 μm, 500 μm-2,000 μm, 600 μm-2,000 μm, 700 μm-2,000 μm, 800 μm-2,000 μm, 900 μm-2,000 μm, 1000 μm-2,000 μm, 1100 μm-2,000 μm, 1200 μm-2,000 μm, 1300 μm-2,000 μm, 1400 μm-2,000 μm, 1500 μm-2,000 μm, 1600 μm-2,000 μm, 1700 μm-2,000 m, 1800 μm-2,000 μm, 1900 μm-2,000 μm, when the device does not contain cells. In some embodiments the apertures are spaces such that the distance from the center of one aperture to the center of the adjacent aperture is about 300 μm, 400 μm, 500 μm, 600 μm, 700 μm, 800 μm, 900 μm, 1000 μm, 1100 μm, 1200 μm, 1300 μm, 1400 μm, 1500 μm, 1600 μm, 1700 μm, 1800 μm, 1900 μm, 2000 μm, 2100 μm, 2200 μm, 2300 μm, 2400 μm, 2500 μm, 2600 μm, or 2700 μm, when the device does not contain cells. In some embodiments the apertures are spaces such that the distance from the center of one aperture to the center of the adjacent aperture is about 1200 μm, 1250 μm, 1270 μm, 1275 μm, or 1300 μm, wherein the device does not contain cells.

In some embodiments, the apertures are spaces such that the distance from the center of one aperture to the center of the adjacent aperture is from about 300 μm-2,000 μm, 400 μm-2,000 μm, 500 μm-2,000 μm, 600 μm-2,000 μm, 700 μm-2,000 μm, 800 μm-2,000 μm, 900 μm-2,000 μm, 1000 μm-2,000 μm, 1100 μm-2,000 μm, 1200 μm-2,000 μm, 1300 μm-2,000 μm, 1400 μm-2,000 μm, 1500 μm-2,000 μm, 1600 μm-2,000 μm, 1700 μm-2,000 μm, 1800 μm-2,000 μm, 1900 μm-2,000 μm, when the device contains cells. In some embodiments the apertures are spaces such that the distance from the center of one aperture to the center of the adjacent aperture is about 300 μm, 400 μm, 500 μm, 600 μm, 700 μm, 800 μm, 900 μm, 1000 μm, 1100 μm, 1200 μm, 1300 μm, 1400 μm, 1500 μm, 1600 μm, 1700 μm, 1800 μm, 1900 μm, 2000 μm, 2100 μm, 2200 μm, 2300 μm, 2400 μm, 2500 μm, 2600 μm, or 2700 μm, when the device contains cells. In some embodiments the apertures are spaces such that the distance from the center of one aperture to the center of the adjacent aperture is about 1200 μm, 1220 μm, 1250 μm, 1270 μm, 1275 μm, or 1300 μm, wherein the device contains cells.

In some embodiments, said device has a thickness from about 100 μm-1,200 μm, 100 μm-1,000 μm, 100 μm-900 μm, 100 μm-800 μm, 100 μm-700 μm, 100 μm-600 μm, 100 μm-500 μm, 100 μm-400 μm, 100 μm-300 μm, 100 μm-200 μm, 100 μm-250 μm, 200 μm-1,200 μm, 200 μm-900 μm, 200 μm-800 μm, 200 μm-700 μm, 200 μm-600 μm, 200 μm-500 μm, 200 μm-300 μm, or 200 μm-250 μm. In some embodiments, said device has a thickness of about 100 μm, 200 μm, 250 μm, 300 μm, 400 μm, 500 μm, 600 μm, 700 μm, 800 μm, 900 μm, 1000 μm, 1100 μm, or 1200 μm. In some embodiments, said device has a thickness of about 250 μm.

In some embodiments, said device comprises a membrane. In some embodiments, the membrane has a thickness of about 300 μm-2,000 μm, 400 μm-2,000 μm, 500 μm-2,000 μm, 600 μm-2.00 μm, 700 μm-2,000 μm, 800 μm-2,000 μm, 900 μm-2,000 μm, 1000 μm-2,000 μm, 1100 μm-2,000 μm, 1200 μm-2,000 μm, 1300 μm-2,000 μm, 1400 μm-2,000 μm, 1500 μm-2,000 μm, 1600 μm-2,000 μm, 1700 μm-2,000 μm, 1800 μm-2,000 μm, 1900 μm-2.00 μm.

Figure 40:
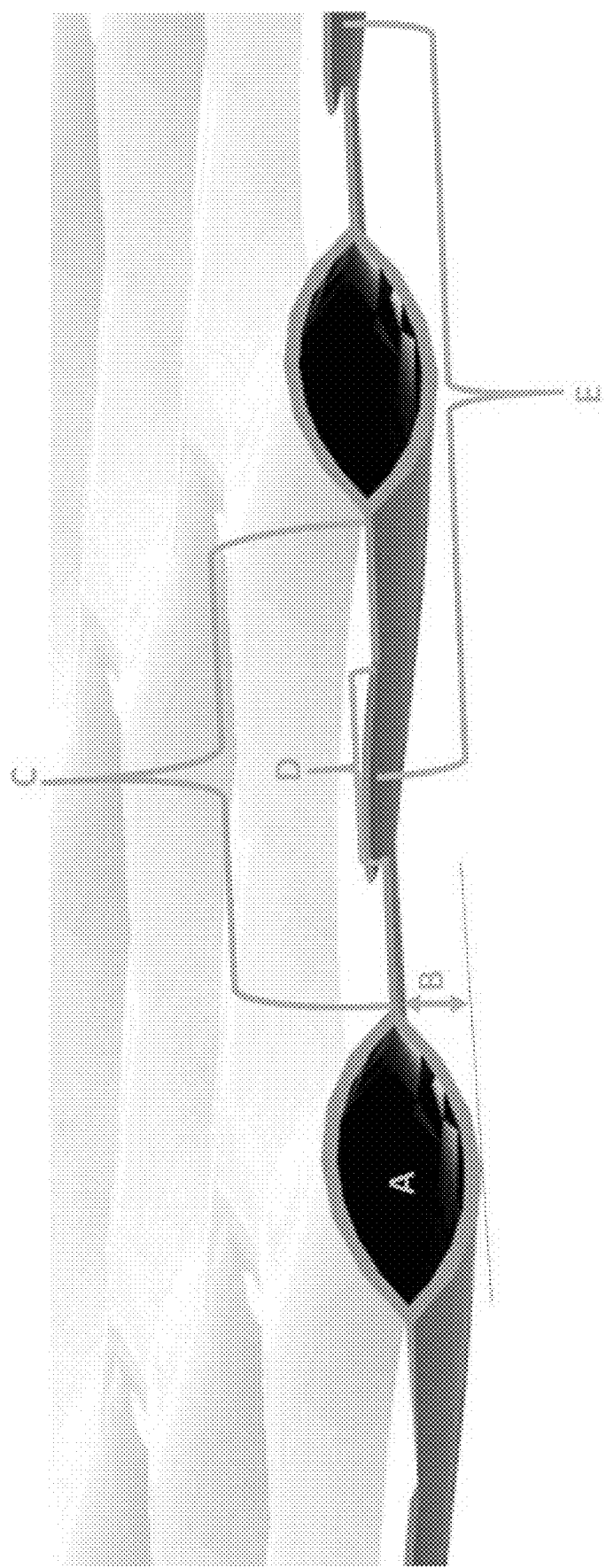
FIG. 40 shows an exemplary cell encapsulating device described herein.

FIG. 40 shows an exemplary device that comprises a series of channels. In some embodiments A is from about 100 μm-1,200 μm, 100 μm-1,000 μm, 100 μm-900 μm, 100 μm-800 μm, 100 μm-700 μm, 100 μm-600 μm, 100 μm-500 μm, 100 μm-400 μm, 100 μm-300 μm, 100 μm-200 μm, 100 μm-250 μm, 200 μm-1,200 μm, 200 μm-900 μm, 200 μm-800 μm, 200 μm-700 μm, 200 μm-600 μm, 200 μm-500 μm, 200 μm-300 μm, or 200 μm-250 μm. In some embodiments, A is about 100 μm, 200 μm, 250 μm, 300 μm, 400 μm, 500 μm, 600 μm, 700 μm, 800 μm, 900 μm, 1000 μm, 1100 μm, or 1200 μm. In some embodiments, said A is about 250 μm.

In some embodiments, B is from about 50 μm-1,000 μm, 50 μm-500 μm, 50 μm-200 μm, 50 μm-150 μm, 50 μm-100 μm, 100 μm-1,000 μm, 100 μm-500 μm, 100 μm-400 μm, 100 μm-300 μm, 100 μm-200 μm, or 100 μm-150 μm. In some embodiments, B is about 25 μm, 50 μm, 75 μm, 100 μm, 110 μm, 120 μm, 150 μm, 200 μm, 300 μm, 50 μm, 400 μm, 500 μm, 600 μm, 700 μm, 800 μm, 900 μm, or 1000 μm. In some embodiments, B is about 100 μm, 110 μm, or 120 μm.

In some embodiments, C is from about 300 μm-1,600 μm, 300 μm-1,500 μm, 300 μm-1,400 μm, 300 μm-1,300 μm, 300 μm-1,200 μm, 300 μm-1,100 μm, 300 μm-1,000 μm, 300 μm-900 μm, 300 μm-800 μm, 300 μm-750 μm, 500 μm-1000 μm, 500 μm-900 μm, 500 μm-800 μm, or 500 μm-750 μm. In some embodiments, C is about 300 μm, 400 μm, 500 μm, 600 μm, 700 μm, 730 μm, 740 μm, 750 μm, 760 μm, 800 μm, 900 μm, 1000 μm, 1100 μm, 1200 μm, 1300 μm, 1400 μm, 1500 μm, or 1600 μm. In some embodiments, B is about 700 μm, 730 μm, 740 μm, or 750 μm.

In some embodiments, β is from about 100 μm-600 μm, 100 μm-500 μm, 100 μm-400 μm, 100 μm-300 μm, 100 μm-200 μm, 200 μm-600 μm, 200 μm-500 μm, 200 μm-400

μm, or 200 μm-300 μm. In some embodiments, β is about 100 μm, 200 μm, 250 μm, 300 μm, 400 μm, 500 μm, or 600 μm. In some embodiments, β is about 300 μm, 310 μm, 320 μm, 330 μm, 340 μm, or 350 μm.

In some embodiments, E (unfilled) is about 300 μm-2,000 μm, 400 μm-2,000 μm, 500 μm-2,000 μm, 600 μm-2,000 μm, 700 μm-2,000 μm, 800 μm-2,000 μm, 900 μm-2,000 μm, 1000 μm-2,000 μm, 1100 μm-2,000 μm, 1200 μm-2,000 μm, 1300 μm-2,000 μm, 1400 μm-2,000 μm, 1500 μm-2,000 μm, 1600 μm-2,000 μm, 1700 μm-2,000 μm, 1800 μm-2,000 μm, or 1900 μm-2,000 μm. In some embodiments, E (unfilled) is about 300 μm, 400 μm, 500 μm, 600 μm, 700 μm, 800 μm, 900 μm, 1000 μm, 1100 μm, 1200 μm, 1300 μm, 1400 μm, 1500 μm, 1600 μm, 1700 μm, 1800 μm, 1900 μm, 2000 μm, 2100 μm, 2200 μm, 2300 μm, 2400 μm, 2500 μm, 2600 μm, or 2700 μm. In some embodiments, E (unfilled) is about 1200 μm, 1250 μm, 1270 μm, 1275 μm, or 1300 μm.

In some embodiments, E (filled) is about 300 μm-2,000 μm, 400 μm-2,000 μm, 500 μm-2,000 μm, 600 μm-2,000 μm, 700 μm-2,000 μm, 800 μm-2,000 μm, 900 μm-2,000 μm, 1000 μm-2,000 μm, 1100 μm-2,000 μm, 1200 μm-2,000 μm, 1300 μm-2,000 μm, 1400 μm-2,000 μm, 1500 μm-2,000 μm, 1600 μm-2,000 μm, 1700 μm-2,000 μm, 1800 μm-2,000 μm, or 1900 μm-2,000 μm. In some embodiments, E (filled) is about 300 μm, 400 μm, 500 μm, 600 μm, 700 μm, 800 μm, 900 μm, 1000 μm, 1100 μm, 1200 μm, 1300 μm, 1400 μm, 1500 μm, 1600 μm, 1700 μm, 1800 μm, 1900 μm, 2000 μm, 2100 μm, 2200 μm, 2300 μm, 2400 μm, 2500 μm, 2600 μm, or 2700 μm. In some embodiments, E (filled) is about 1200 μm, 1250 μm, 1270 μm, 1275 μm, or 1300 μm.

In some embodiments, A is about 100-300 μm, B is about 50-200 μm, C is about 600-800 μm, β is about 200-300 μm, E (unfilled) is about 1100-1300 μm, and E (filled) is about 100-1300 μm. In some embodiments, E (unfilled) is higher than E (filled). In some embodiments, A is about 250 μm, B is about 110 μm, C is about 740 μm, β is about 320 μm, E (unfilled) is about 1270 μm, and E (filled) is about 1120 μm.

Methods of Treatment

Disclosed herein are methods of treating a human subject with a disease characterized by high blood sugar levels over a prolonged period of time. In some embodiments said disease is diabetes. In some embodiments, said disease is type I diabetes. In some embodiments, said disease is type II diabetes. In some embodiments, cells described herein are administered to said subject with in a cell encapsulating device. In some embodiments, cells described herein are administered to said subject in the absence of a cell encapsulating device. In some embodiments, the subject is not administered a preparatory regimen that comprises at least one immunosuppressive agent. In some embodiments, the subject is administered a preparatory regimen that comprises at least one immunosuppressive agent. In some embodiments, pancreatic endocrine progenitor cells, PDX1 expressing NKX6.1 expressing pancreatic progenitor cells, PDX1 expressing pancreatic progenitor cells, or β cells, or any combination thereof, are administered to said subject. In some embodiments, pancreatic endocrine progenitor cells, PDX1 expressing NKX6.1 expressing pancreatic progenitor cells, or PDX1 expressing pancreatic progenitor cells are administered to said subject, wherein at least a portion of said cells mature in vivo into β cells exhibiting glucose stimulated insulin secretion. In some embodiments, stem cell derived β cells are administered to said subject, wherein said β cells exhibit glucose stimulated insulin secretion in vitro. In some embodiments, said stem cell derived β cells exhibit glucose stimulated insulin secretion to at least 2 (e.g., 3, 4, 5, 6, 7, 8, 9, 10, or more) glucose challenges in vitro. The method of any preceding claim, wherein said Pdx1 expressing pancreatic progenitor cells comprise a genomic disruption in at least one gene sequence, wherein said disruption reduces or eliminates expression of a protein encoded by said gene sequence.

In some embodiments, said Pdx1 expressing, NKX6.1 expressing pancreatic progenitor cells comprise a genomic disruption in at least one gene sequence, wherein said disruption reduces or eliminates expression of a protein encoded by said gene sequence. In some embodiments, said Pdx1 expressing, pancreatic progenitor cells comprise a genomic disruption in at least one gene sequence, wherein said disruption reduces or eliminates expression of a protein encoded by said gene sequence. In some embodiments, said pancreatic endocrine progenitor cells comprise a genomic disruption in at least one gene sequence, wherein said disruption reduces or eliminates expression of a protein encoded by said gene sequence. In some embodiments, said β cells comprise a genomic disruption in at least one gene sequence, wherein said disruption reduces or eliminates expression of a protein encoded by said gene sequence. In some embodiments, said at least one gene sequence encodes an MHC-Class I gene. In some embodiments, said MHC-Class I gene encodes beta-2 microglobulin (B2M), HLA-A, HLA-B, or HLA-C. In some embodiments, said cells comprise a genomic disruption in a natural killer cell activating ligand gene. In some embodiments, said natural killer cell activating ligand gene encodes intercellular adhesion molecule 1 (ICAM1), CD58, CD155, carcinoembryonic antigen-related cell adhesion molecule 1 (CEACAM1), cell adhesion molecule 1 (CADM1), MHC-Class I polypeptide-related sequence A (MICA), or MHC-Class I polypeptide-related sequence B (MICB).

EXAMPLES

The examples below further illustrate the described embodiments without limiting the scope of this disclosure.

Example 1. Identification of Modulators of Pancreatic Differentiation

As shown in FIG. 1, one exemplary screening process comprises a high-throughput primary screen using immunocytochemistry (ICC) followed by a secondary hit validation via flow cytometry. Top validated hits are then evaluated in scaled-up experimental settings, where S5 cells are further matured into S6 cells.

For a primary screen, PP2 (S4C) SEM01 cells derived from stem cell line D695, D696, and D706 were used. PP2 cells were produced in spinner flask and then plated on day 5 of Stage 4 (S4d5) into 96 well plate which were coated with Matrigel. Compound libraries (e.g., Wnt Pathway Library, Stem Cell Signaling Library, Epigenetics Library, GPCR, and Hormone Library) were screened through, and each compound was added at 1.0 or 10 μM concentration on day 1 and day 2 of Stage 5 (S5d1-S5d2). Expression percentage of Nkx6.1, ISL1, and both was examined by ICC and quantified using Image Express Micro 4 and Multiwavelength scoring algorithm as shown in FIG. 2. FIGS. 5-9 are exemplary quantification results.

Figure 11:
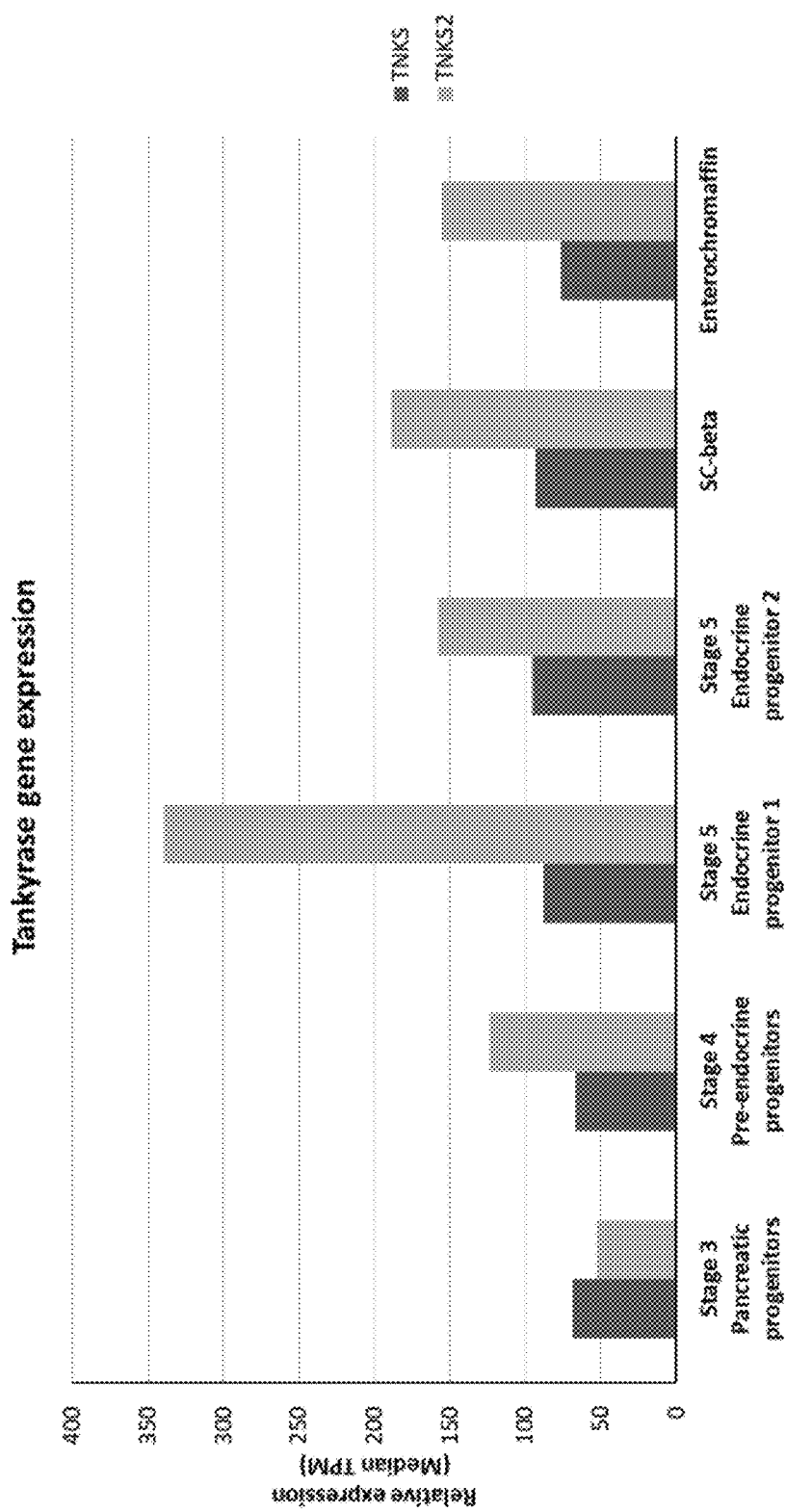
FIG. 11 is a graph summarizing expression level of Tankyrase 1 and 2 at different stages of pancreatic differentiation.
Figure 12:
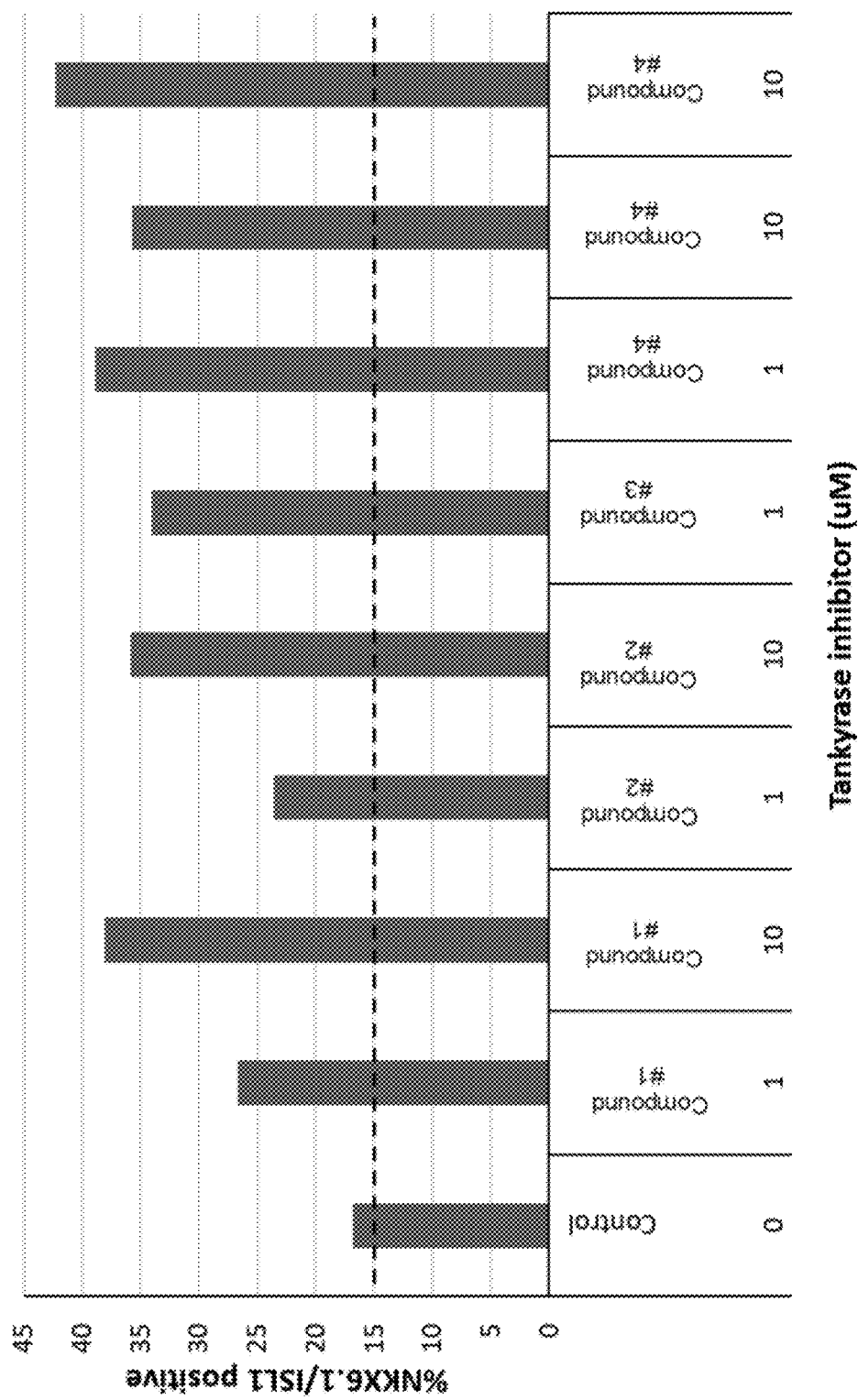
FIG. 12 is a graph summarizing dose-dependent effects of a number of different exemplary compounds that inhibits Tankyrase activity on level of NKX6.1+/ISL1+ cells in S5 cell population.
Figure 13:
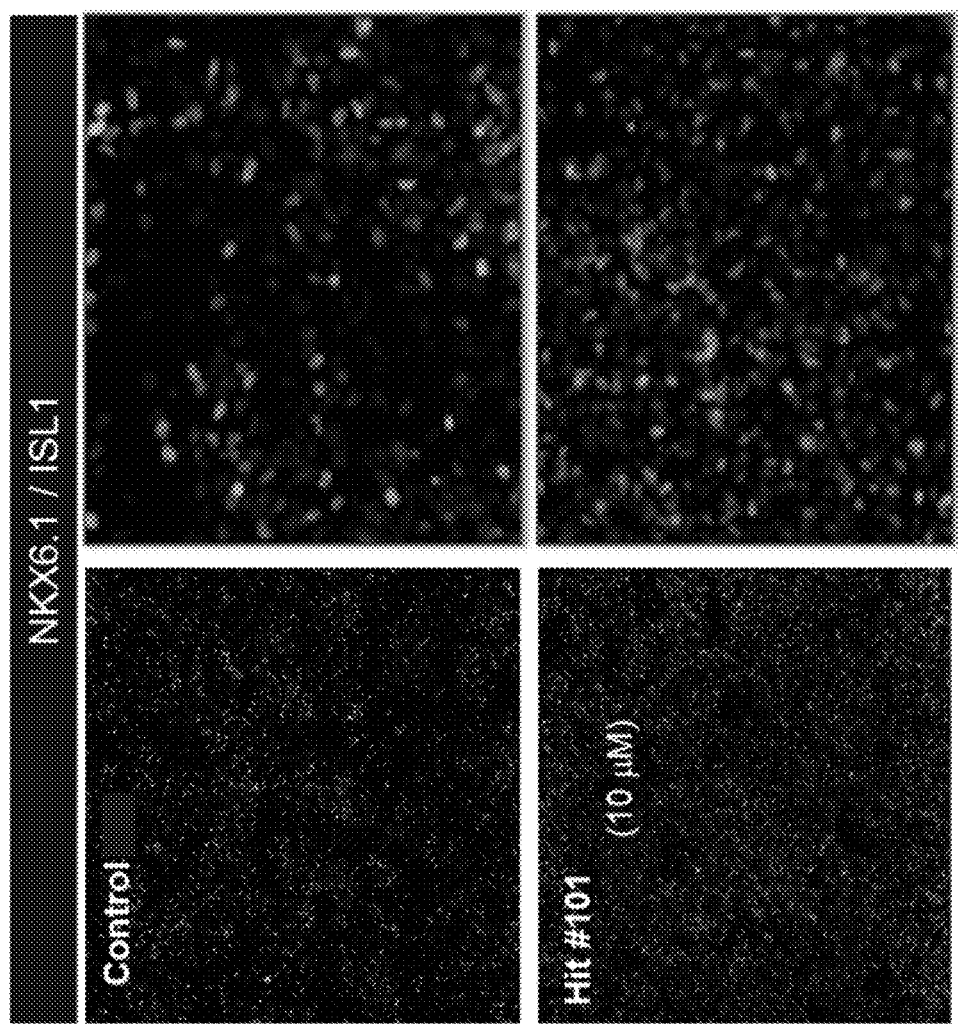
FIG. 13 shows exemplary images demonstrating that an exemplary compound increased level of NKX6.1+/ISL1+ cells in S5 cell population.

Example 2. Increase in NKX6.1+/ISL1+ Pancreatic β Cells Induced by Inhibitor of Tankyrase As shown in FIG. 11, Tankyrase 2 expression level changes at different stage of pancreatic stages. Inhibition of Tankyrase was shown to increase NKX6.1+/ISL1+ pancreatic D3 cells. As shown in FIG. 12, exemplary compounds that inhibit Tankyrase 2 were shown to induce increase in NKX6.1+/ISL1+ pancreatic β cells at Stage 5 and such increases exhibited dose-dependency.

Figure 14:
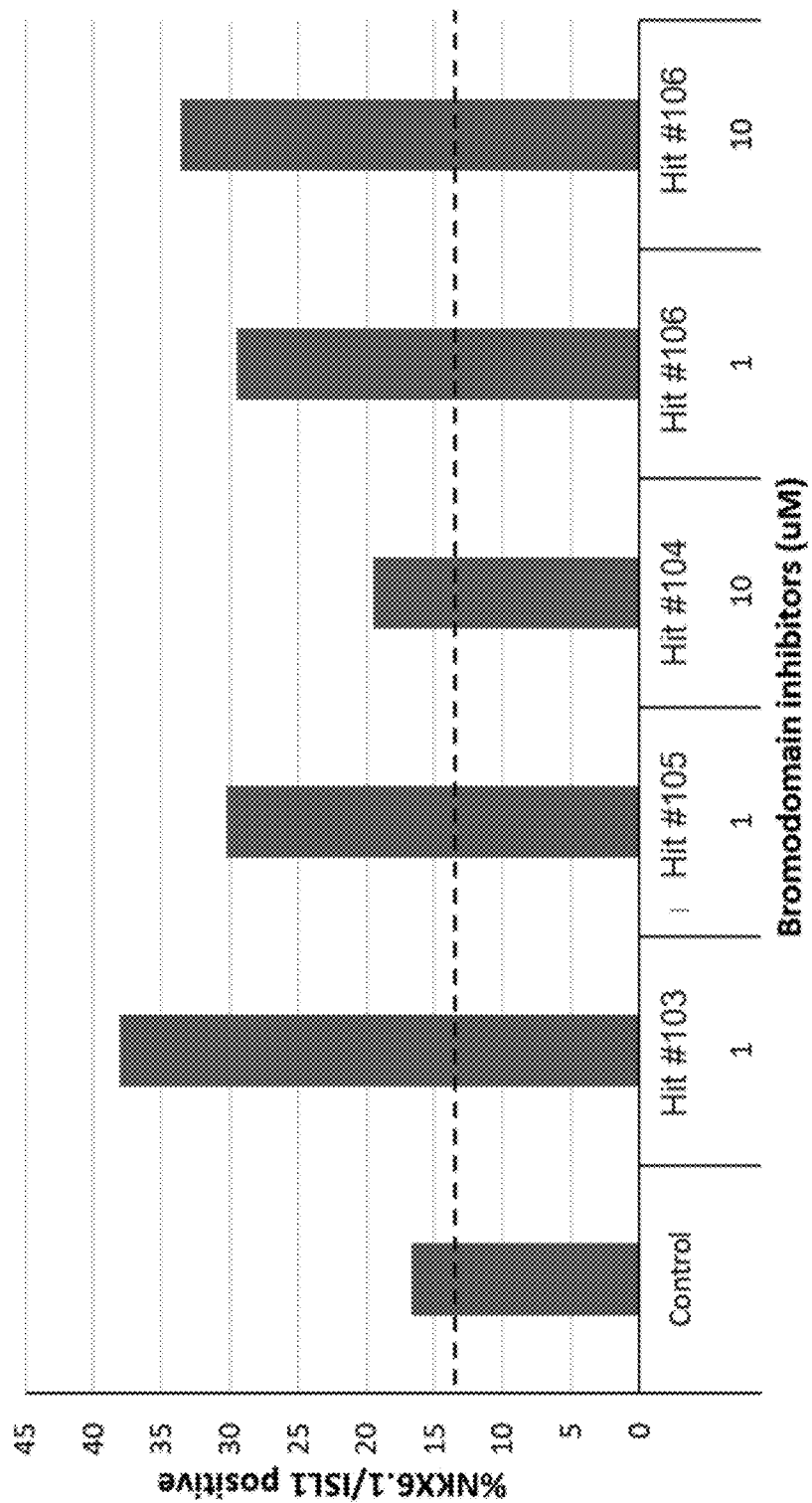
FIG. 14 is graph summarizing dose-dependent effects of a number of different exemplary compounds that inhibits bromodomain of Bromodomain and Extra-Terminal (BET) proteins on level of NKX6.1/ISL1 positive cells in S5 cell population.
Figure 15A:
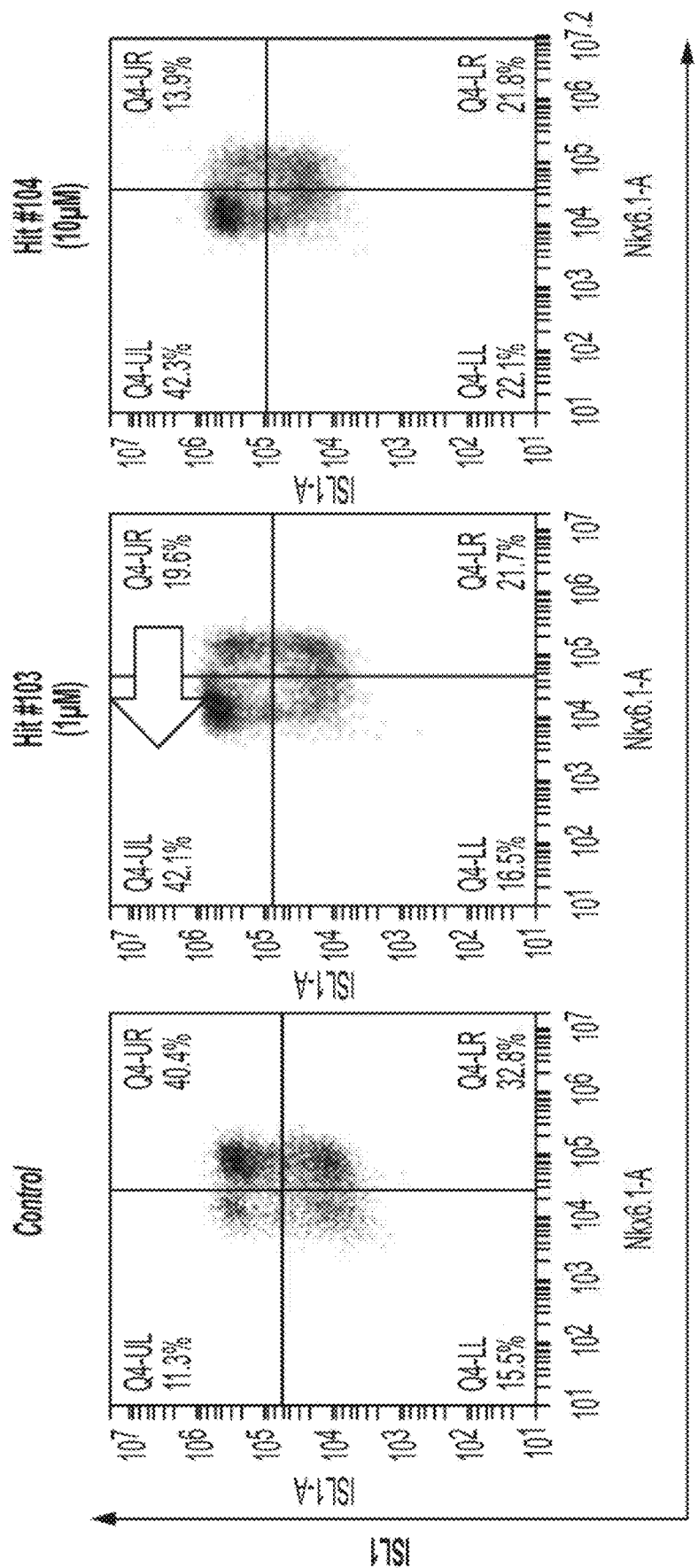
FIGS. 15A-15B show cell sorting results demonstrating effects of a number of different exemplary compounds that inhibits bromodomain of Bromodomain and Extra-Terminal (BET) proteins on level of NKK6.1 and ISL1 expression in a S5 cell population.
Figure 15B:
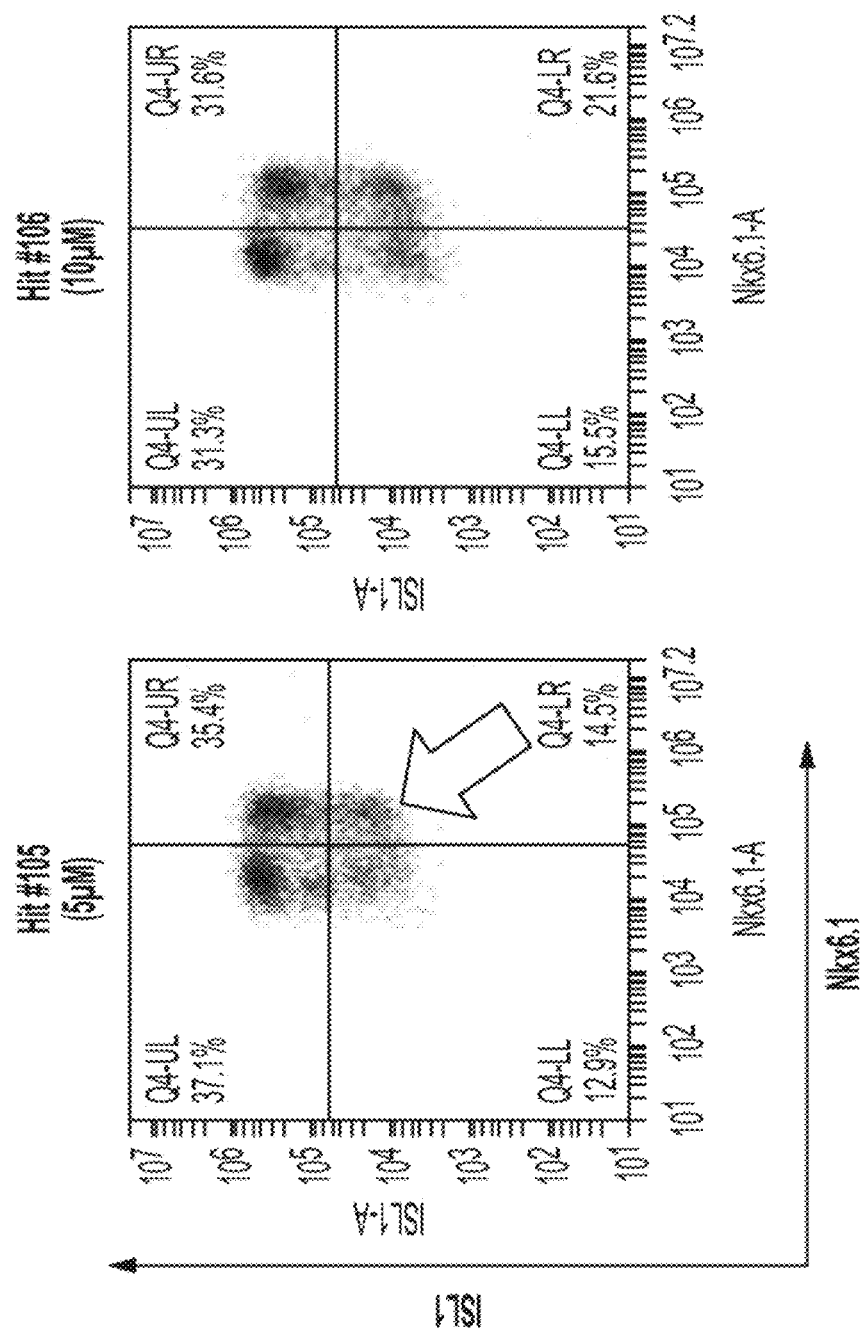
Figure 16:
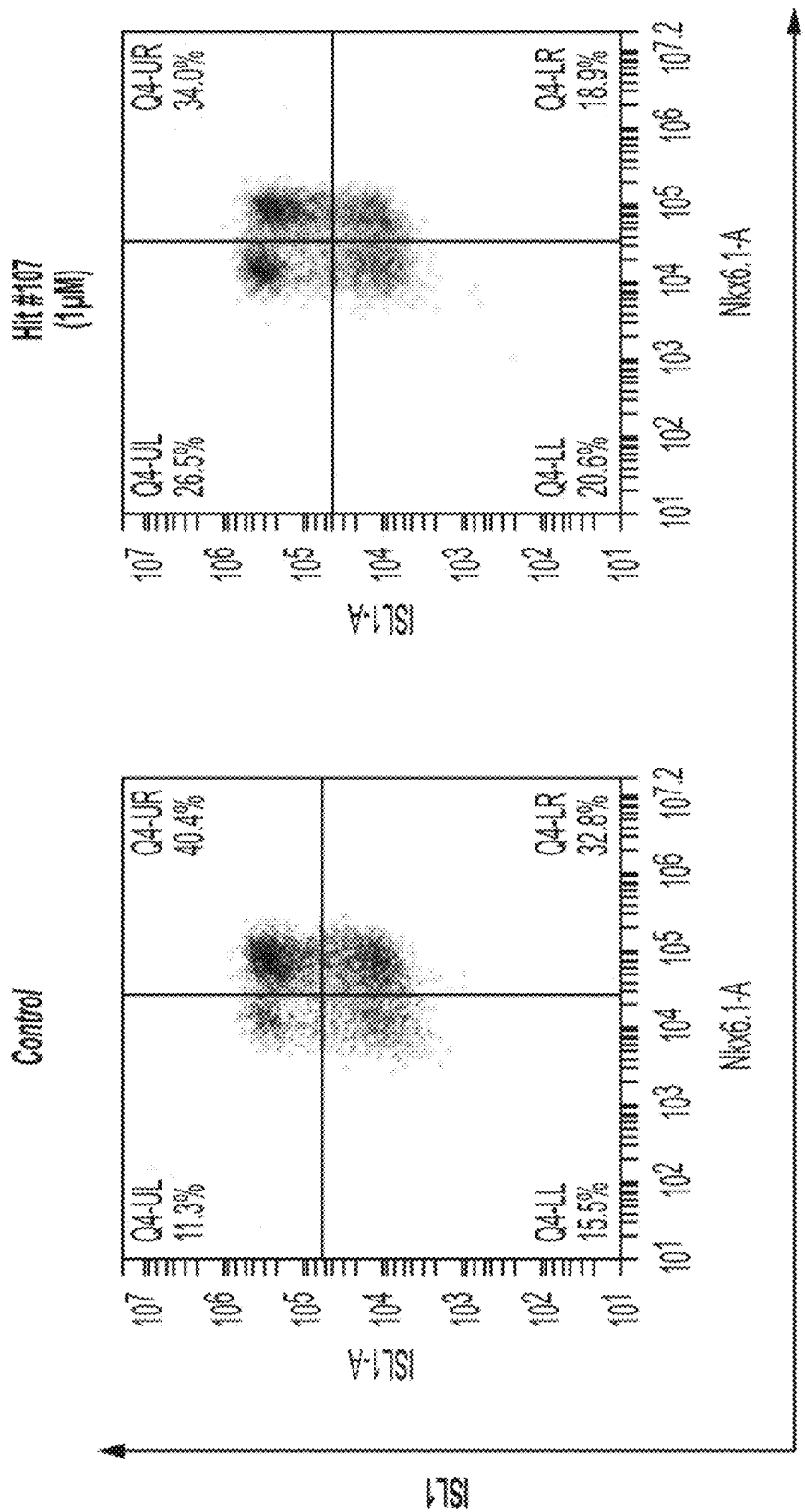
FIG. 16 shows cell sorting results demonstrating effects of an exemplary compound that inhibits HDAC on the level of NKK6.1 and ISL1 expression in a S5 cell population.
Figure 17A:
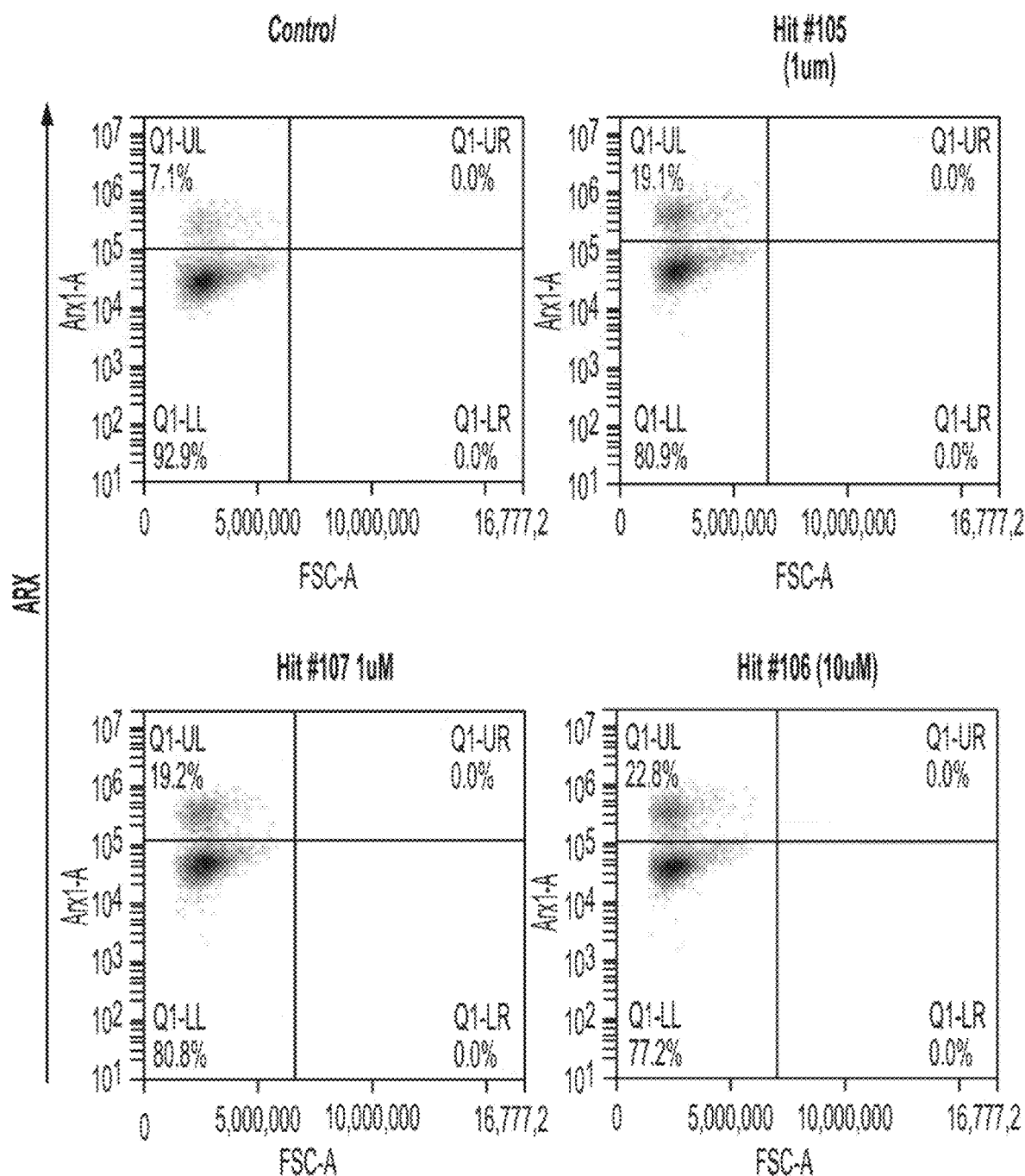
FIGS. 17A and 17B show cell sorting results demonstrating effects of a number of different exemplary compounds that inhibits bromodomain of Bromodomain and Extra-Terminal (BET) proteins on Arx expression level in a S5 cell population.
Figure 17B:
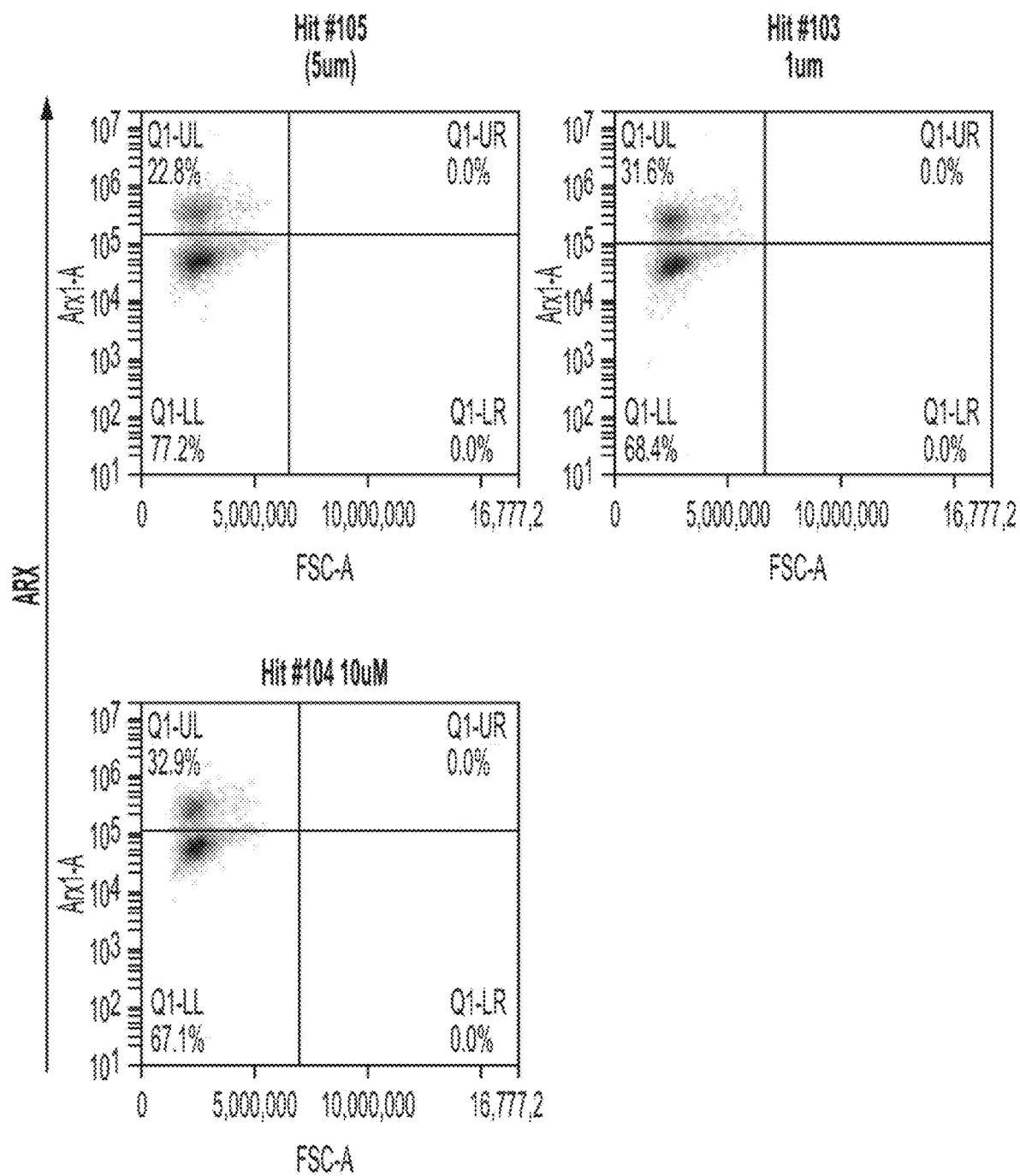
Figures 17C, 18A:
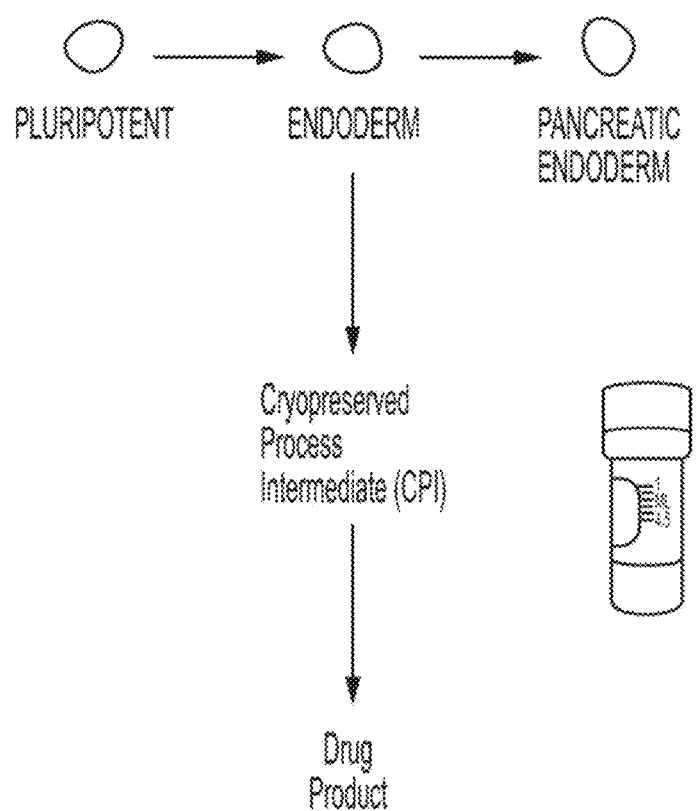
FIG. 17C summarizes level of Arx+, GCG+, and Arx+/GCG+ cells when treated with different exemplary compounds, respectively.
FIG. 18A shows a schematic of an exemplary protocol described herein, wherein pluripotent stem cells (e.g., induced pluripotent stem cells (iPSCs)) are differentiated into endoderm and subsequently into pancreatic endoderm (and in some embodiments subsequently into pancreatic endocrine progenitor cells) and cryopreserved as a cryopreserved process intermediate (CPI) before being further matured into SC-β cells for use in a drug product.

Example 3. Increase in Pancreatic α Cells Induced by Inhibitor BET Bromodomain or HDAC Inhibitor As shown in FIG. 14, exemplary compounds that inhibit BET bromodomain or HDAC enzyme were shown to induce increase in NKX6.1/ISL1 positive cells at Stage 5 and such increases exhibited dose-dependency. Further validation of these exemplary compounds revealed that, as shown in FIGS. 15A, 15B, and FIG. 16, these exemplary compounds induced increase in NKX6.1-/ISL1+ cells at Stage 5. Furthermore, as shown in FIGS. 17A-17C, these compounds induced increase in expression of Arx and Glucagon (GCG) at Stage 5, suggesting an increase in percentage of pancreatic α cells.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Figure 18B:
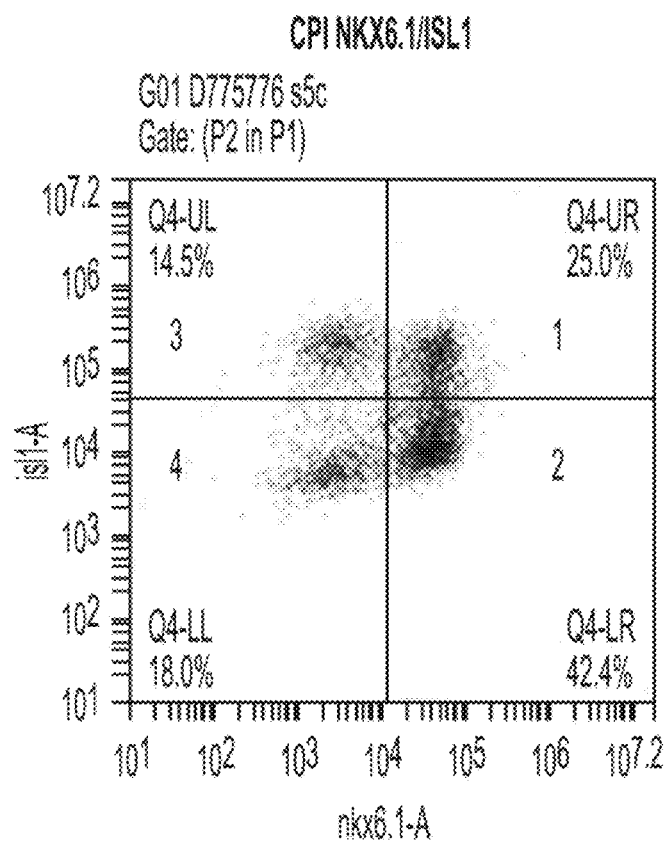
FIG. 18B shows a plot from a FACS analysis of the composition of cells in an exemplary control cryopreserved process intermediate (CPI). The CPI composition contains about 25% NKX6.1+/ISL1+SC-β cells, about 14.5% NKX6.1-/ISL1+ SC-α cells, about 42.4% NKX6.1-/ISL1-SC-double negative cells, and about 18.0% SC-enterochromaffin (EC) cells. Both SC-EC and NKX6.1-/ISL1-SC-double negative (DN) cells can be considered off target cell populations for certain applications described herein, in the production of SC-islets.
Figure 18C:
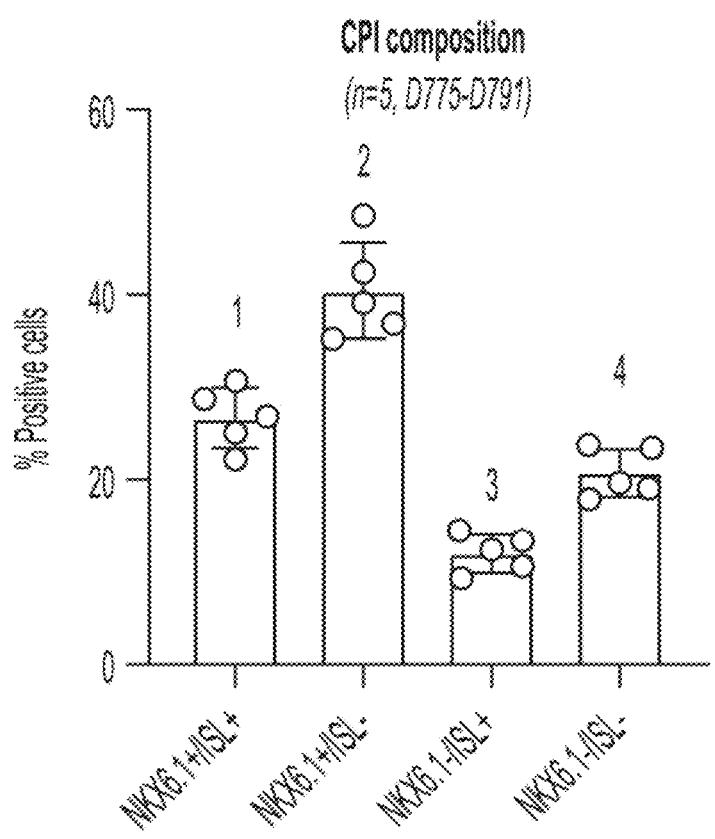
FIG. 18C shows a graphical depiction of the CPI composition data presented in FIG. 18B.
Figure 19:
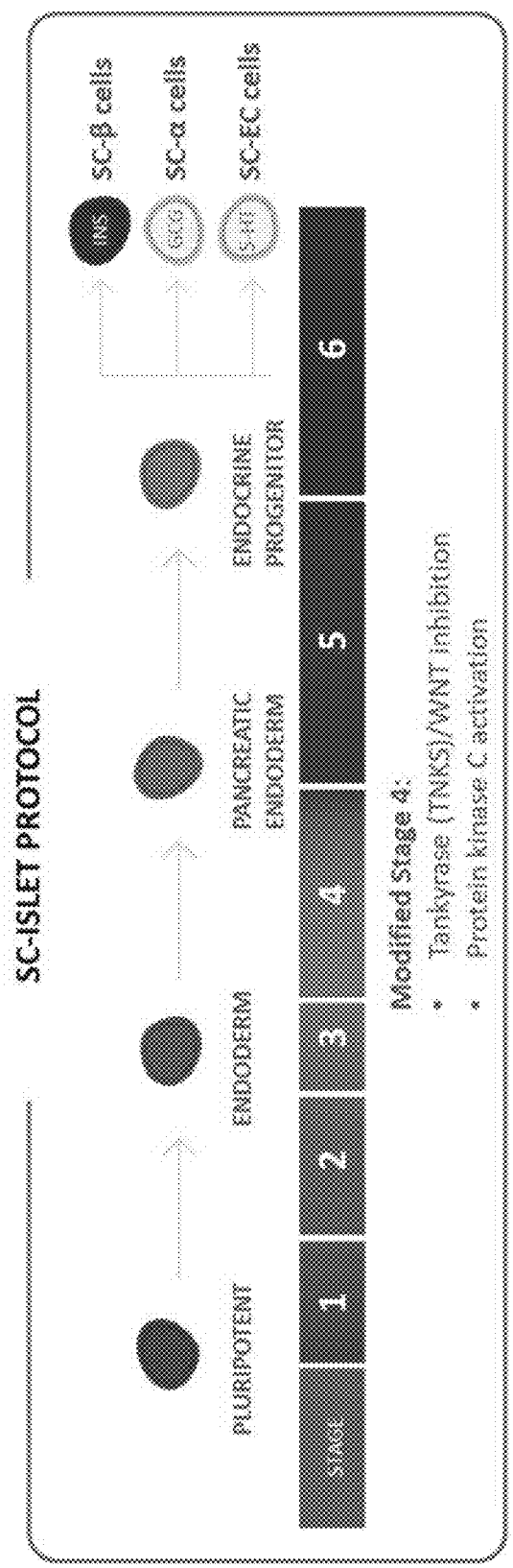
FIG. 19 shows an example of an embodiment of an SC-islet production protocol described herein, wherein stage 4 (differentiation of endoderm cells into pancreatic endoderm cells) medium is modified to include a tankyrase (TNKS) inhibitor and/or a protein kinase C activator (PKC), or both. As shown herein, the modifications to the stage 4 medium improve the CPI composition by increasing the percentage of SC-β cells (NKX6.1+/ISL1+), increasing the percentage of SC-α cells (GCG+; ARX+; NKX6.1-/ISL1+), reducing the percentage of SC-EC cells (VMAT1+; CDX2+; NKX6.1+/ISL1-), and reducing the percentage of DN cells (NKX6.1-/ISL1-).
Figure 39:
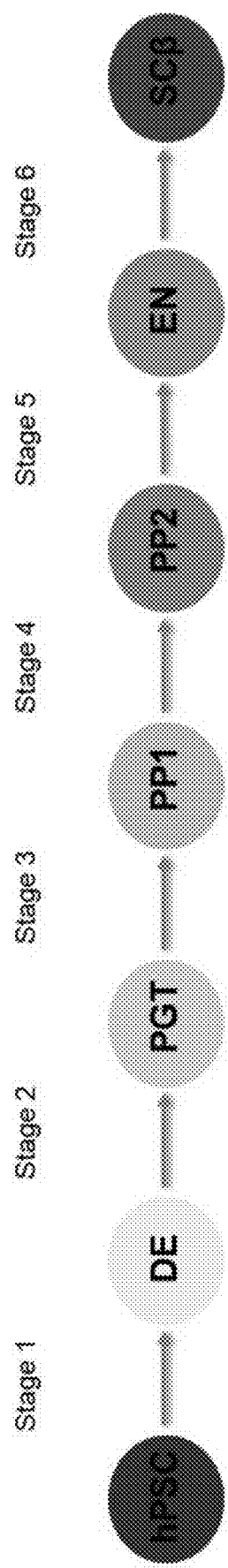
FIG. 39 shows a graphic depiction of an exemplary staged differentiation process described herein, wherein human pluripotent stem cells (e.g., human induced pluripotent stem cells) are differentiated into mature functional SC-β cells or a precursor thereof. hSPC: human pluripotent stem cell; DE: definitive endoderm; PGT: primitive gut tube cells; PP1: Pdx1-positive pancreatic progenitor cells; PP2: Pdx1-positive, NKX6-1-positive pancreatic progenitor cells; EN: endocrine progenitor cells; SC-β: insulin secreting stem cell derived β cell.

Example 4. Use of Tankyrase Inhibitors During Differentiation of Pancreatic Progenitor Cells In certain embodiments described herein, induced pluripotent stem cells are differentiated into SC-β cells or precursors thereof in vitro. An exemplary differentiation protocol is outlined in FIG. 39. Endocrine progenitor cells produced by Stage 5 can comprise a mixture of cell types. For example, the composition can include NKX6.1+/ISL1+β cells, NKX6.1-/ISL1+α cells, NKX6.1-/ISL1-double negative cells, and enterochromaffin (EC) cells (FIG. 18B and FIG. 18C). For example, FIG. 18B and FIG. 18C show a Stage 5 process intermediate cell composition that comprises about 25% NKX6.1+/ISL1+[β cells, about 14.5% NKX6.1-/ISL1+α cells, about 42.4% NKX6.1-/ISL1-double negative cells, and about 18.0% enterochromaffin (EC) cells. For certain applications described herein, such as the production of SC-islets, both NKX6.1-/ISL1-double negative (DN) SC-cells and SC-enterochromaffin (EC) cells are off target cell populations. To improve the Stage 5 cellular composition (e.g., increased percentage of NKX6.1+/ISL1+ SC-β cells and NKX6.1-/ISL1+SC-α cells; decreased percentage of NKX6.1-/ISL1-SC-β N cells and SC-EC cells), modifications to the Stage 4 and/or Stage 5 medium were evaluated (FIG. 19).

Figure 29:
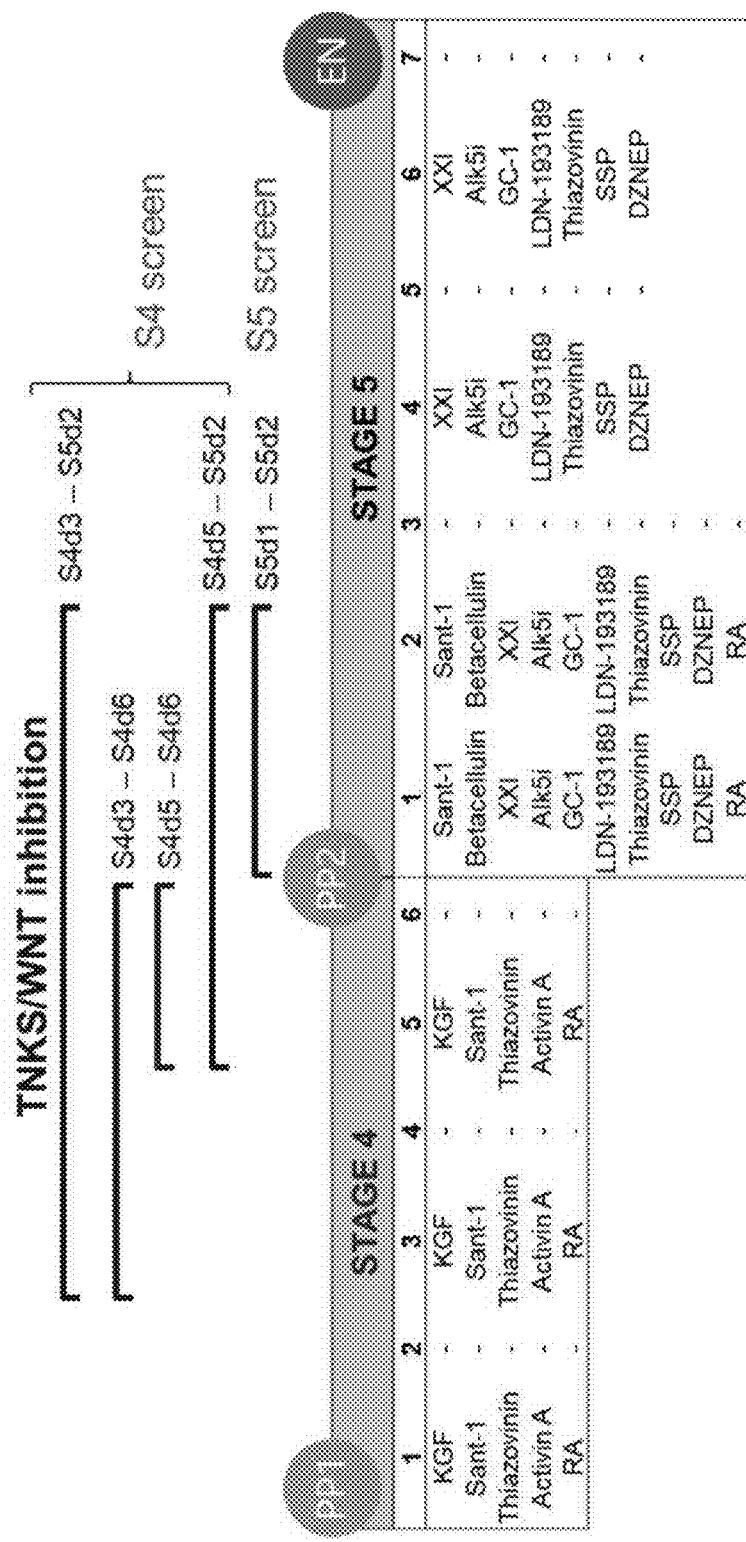
FIG. 29 shows a schematic depicting exemplary Stage 4 and Stage 5 differentiation protocols utilizing a TNKS/Wnt inhibitor, as described herein. For example, in some embodiments, a TNKS/Wnt inhibitor is utilized during days 3-6 of Stage 4 (S4d3-S4d6), days 5-6 of Stage 4 (S4d5-S4d6), day 5 of Stage 4 through day 2 of Stage 5 (S4d5-S5d2), days 1-2 of Stage 5 (S5d1-S5d2), or day 3 of Stage 4 through day 2 of Stage 5 (S4d3-S5d2).

FIG. 29 shows a schematic representation of experiments conducted using Tankyrase (TNKS)/Wnt inhibition during Stage 4 or during Stage 4 and Stage 5 to evaluate the effect of such inhibition on the composition of the cell population at the end of Stage 5.

Figure 20A:
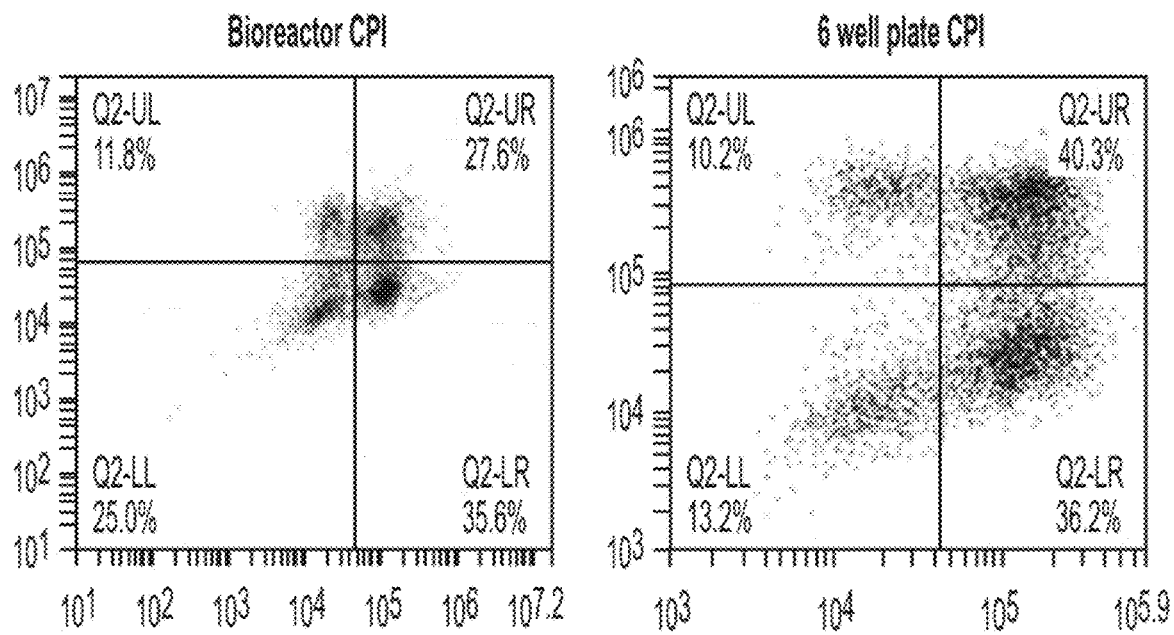
FIG. 20A shows a plot from a FACS analysis of cells at the end of stage 5 (differentiation of pancreatic endoderm cells into pancreatic endocrine progenitor cells) produced using a control stage 4 medium that did not contain a TNKS/WNT inhibitor or a PKC activator.
Figure 20B:
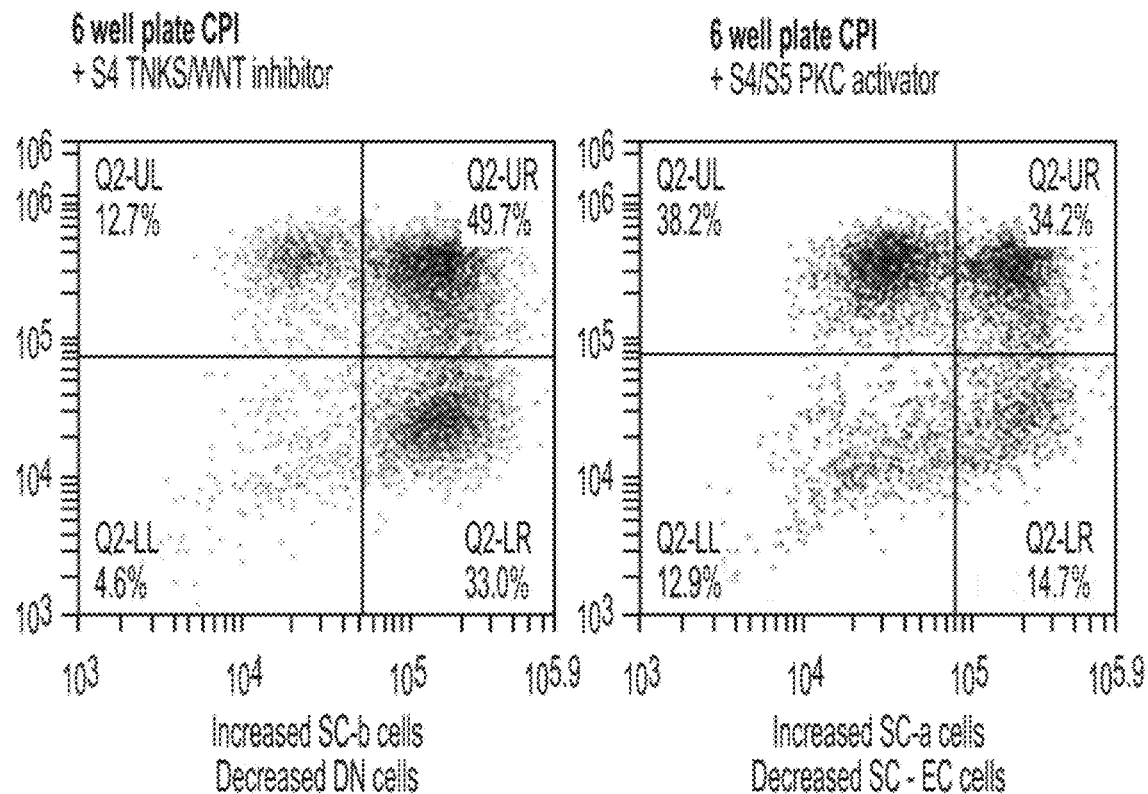
FIG. 20B shows a plot from a FACS analysis of cells at the end of stage 5 (differentiation of pancreatic endoderm cells into pancreatic endocrine progenitor cells) produced using a modified stage 4 medium that contained a TNKS/WNT inhibitor or a PKC activator. Inclusion of the TNKS/WNT inhibitor increased the percentage of SC-β cells and decreased the percentage of NKX6.1-/ISL1-double negative (DN) cells compared to control. Inclusion of the PKC activator increased the percentage of SC-α cells and decreased the percentage of SC-EC cells compared to control.
Figures 21A, 21B:
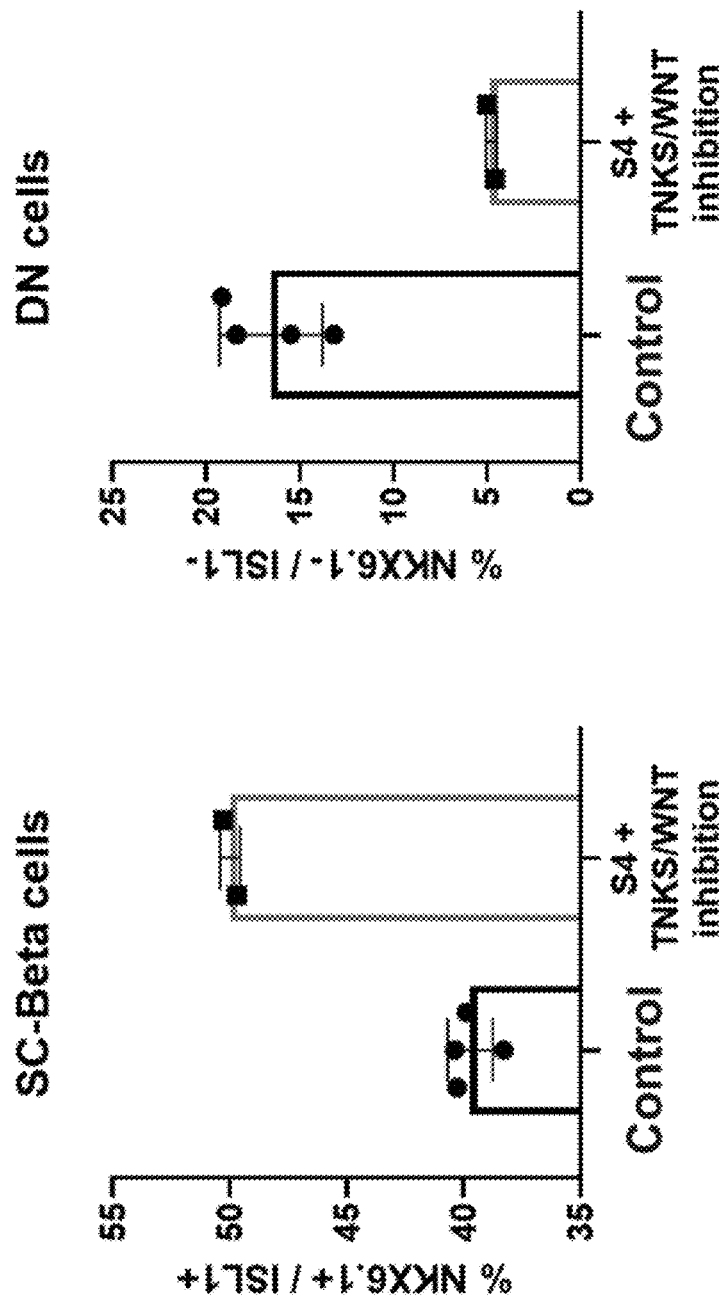
FIG. 21A shows a bar graph depicting the percentage of SC-β cells (NKX6.1+/ISL1+ cells) at the end of stage 5 produced using a control stage 4 medium (lacking a TNKS/Wnt inhibitor) (control) or a modified stage 4 medium containing a TNKS/Wnt inhibitor. Inclusion of the TNKS/WNT inhibitor increased the percentage of SC-β cells compared to control.
FIG. 21B shows a bar graph depicting the percentage of NKX6.1-/ISL1-double negative (DN) cells at the end of stage 5 produced using a control stage 4 medium (lacking a TNKS/Wnt inhibitor) (control) or a modified stage 4 medium containing a TNKS/Wnt inhibitor. Inclusion of the TNKS/WNT inhibitor decreased the percentage of NKX6.1-/ISL1-double negative (DN) cells compared to control.
Figure 28:
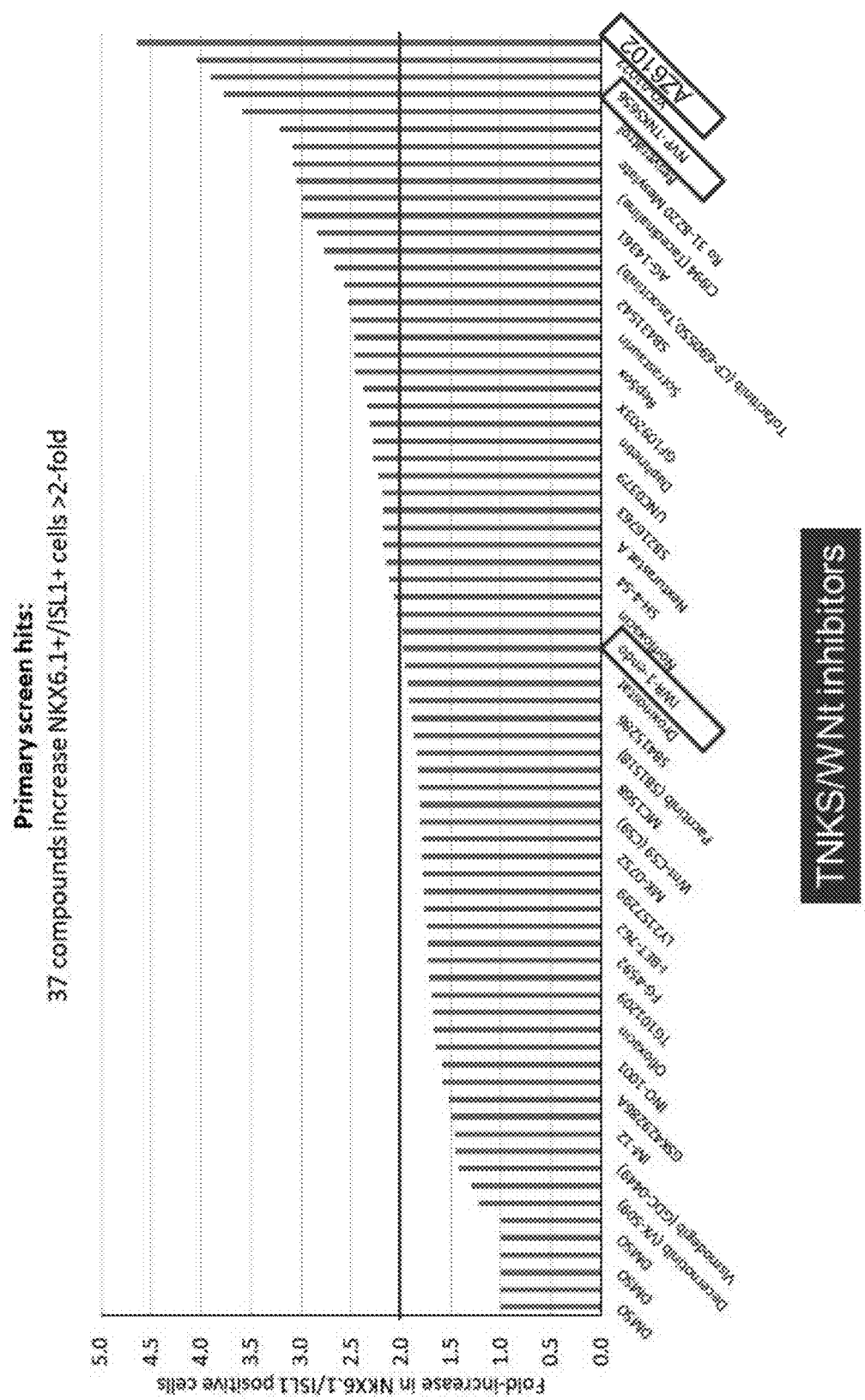
FIG. 28 shows a bar graph depicting results from a screen of TNKS/WNT inhibitors for the ability to increase the percentage of NKX6.1+/ISL1+SC-β cells at the end of stage 5 when included in stage 4 medium. The screen showed that 37 different compounds increase the percentage of NKX6.1+/ISL1+ cells at the end of Stage 5 more than two-fold compared to the control (DMSO).

As shown in FIGS. 20A-20B and FIGS. 21A-21B, TNKS/Wnt inhibition during Stage 4 increased the percentage of NKX6.1+/ISL1+β cells (FIG. 21A; FIGS. 20A-20B) and decreased the percentage of NKX6.1-/ISL1-double negative cells (FIG. 21B; FIGS. 20A-20B) at the end of stage 5. Multiple TNKS/Wnt inhibitors that increase the percentage of NKX6.1+/ISL1+β cells at the end of Stage 5 at least two-fold over the control were identified (FIG. 28).

Figure 30A:
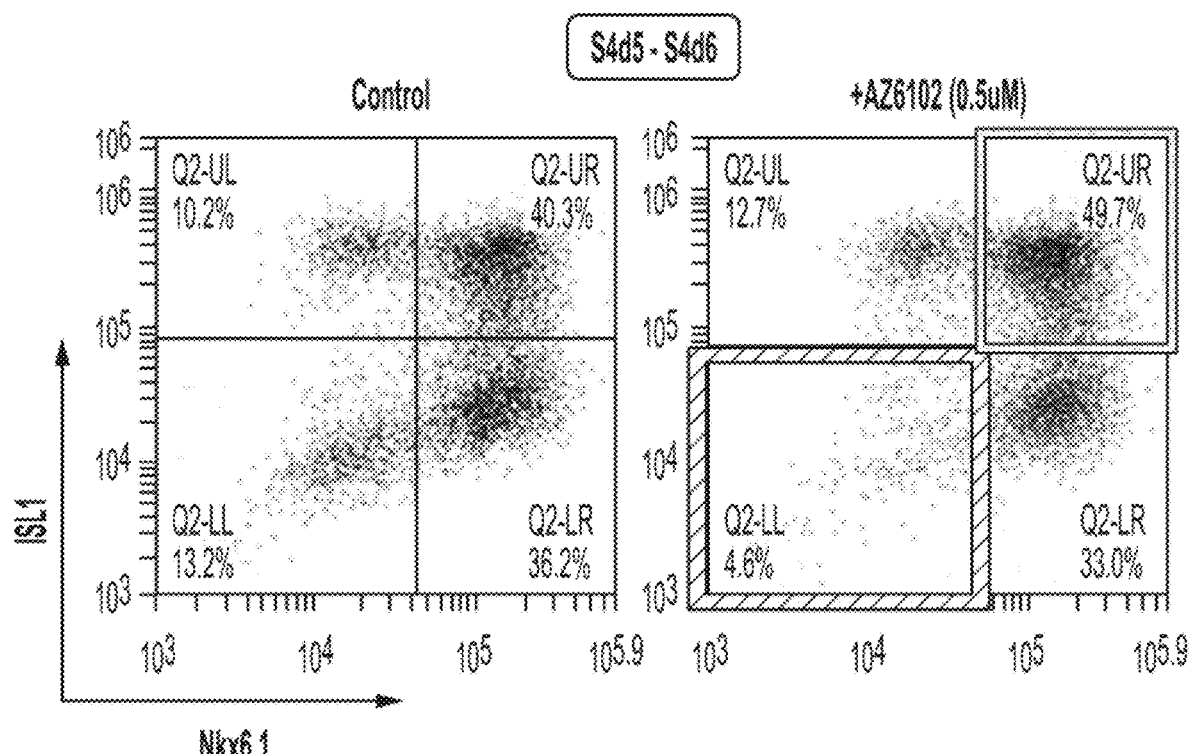
FIG. 30A a plot from a FACS analysis of the percentage of NKX6.1+/ISL1+SC-β cells at the end of stage 5 produced using a control stage 4 medium (did not contain a TNKS/Wnt inhibitor) or a modified stage 4 medium that contained a TNKS/Wnt inhibitor (0.5 μM AZ6102) during S4d5-S4d6. Inclusion of the TNKS/Wnt inhibitor (0.5 μM AZ6102) during S4d5-S4d6 increased the percentage of NKX6.1+/ISL1+SC-β cells at the end of stage 5.
Figure 30B:
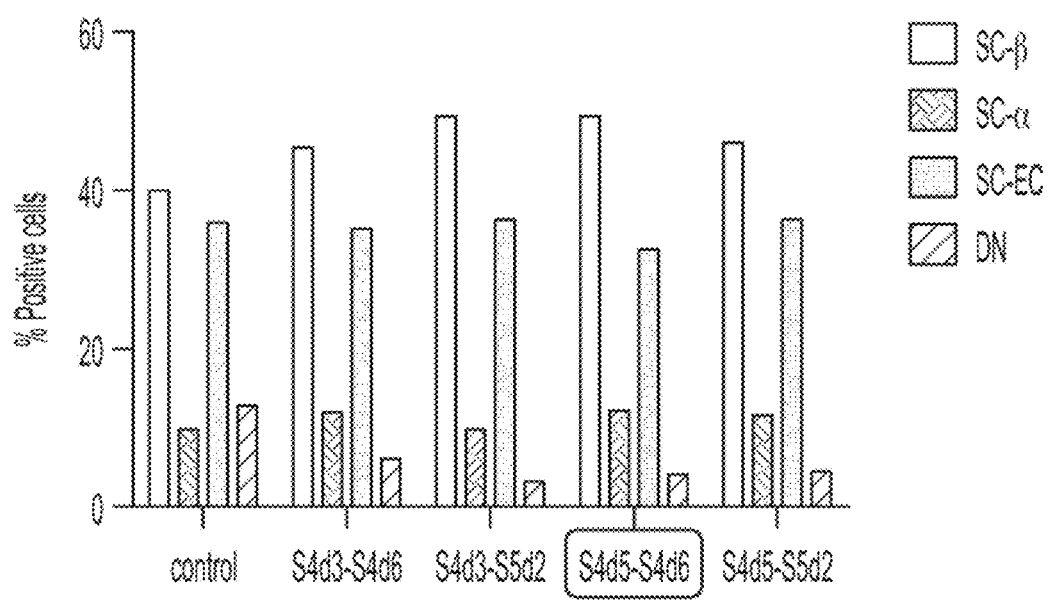
FIG. 30B shows a bar graph depicting the percent of NKX6.1+/ISL1+SC-β cells, SC-α cells, SC-EC cells, and NKX6.1-/ISL1-DN cells at the end of stage 5 produced using a control (stage 4 medium that did not contain a TNKS/Wnt inhibitor) or a modified stage 4 medium that contained a TNKS/Wnt inhibitor (0.5 μM AZ6102) during S4d3-S4d6, S4d3-S5d2, S4d5-S4d6, or S4d5-S5d62.
Figures 31A, 31B:
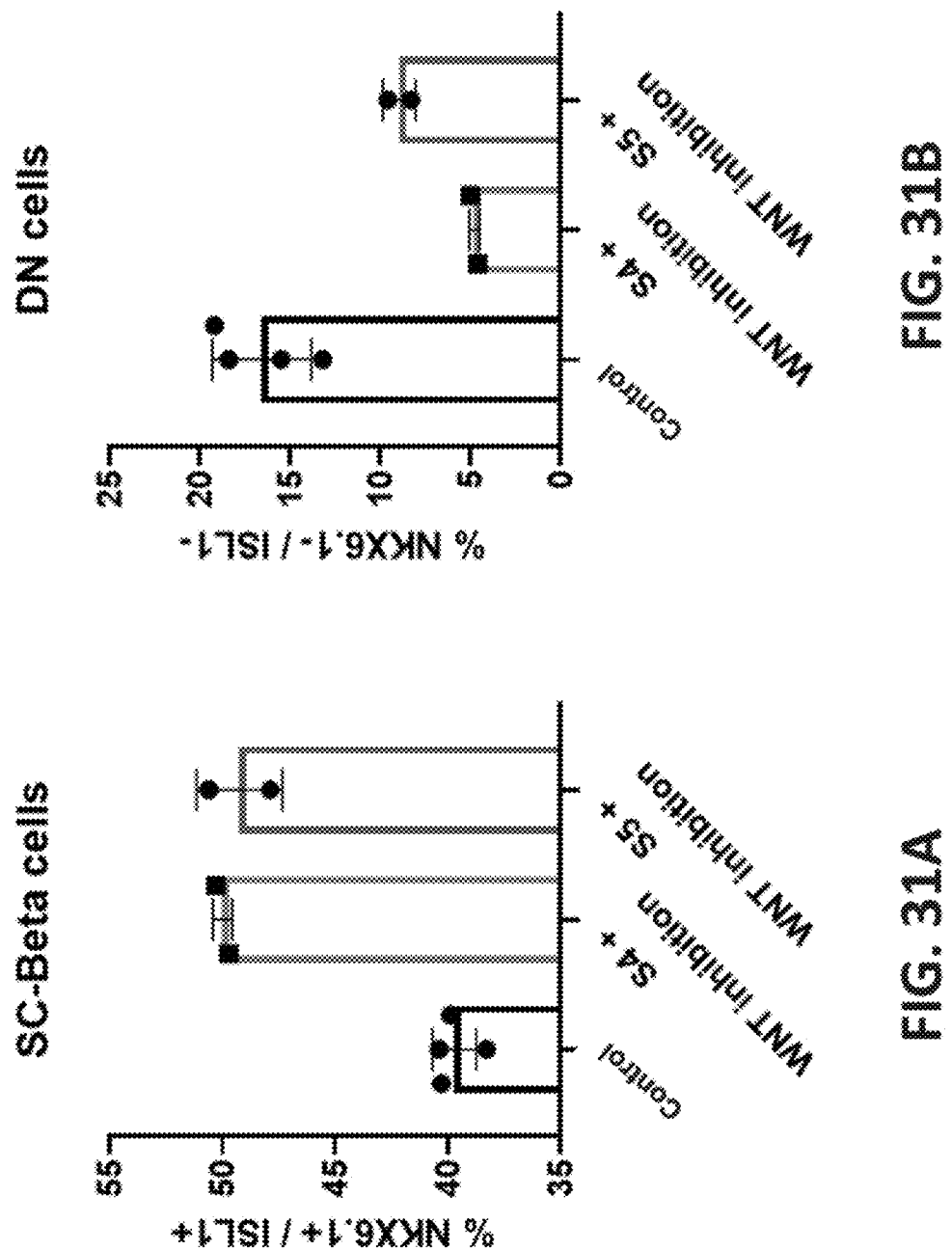
FIG. 31A shows a bar graph depicting the percentage of NKX6.1+/ISL1+SC-β cells at the end of stage 5 produced using a control stage 4 and stage 5 medium that did not contain a TNKS/Wnt inhibitor, a modified stage 4 medium that contained a TNKS/Wnt inhibitor (0.5 μM AZ6102), or a modified stage 5 medium that contained a TNKS/Wnt inhibitor (0.5 μM AZ6102). Inclusion of the TNKS/Wnt inhibitor (0.5 μM AZ6102) during Stage 4 or Stage 5 increased the percentage of NKX6.1+/ISL1+SC-β cells at the end of stage 5.
FIG. 31B shows a bar graph depicting the percentage of NKX6.1-/ISL1-SC-β N (double negative) cells at the end of stage 5 produced using a control stage 4 and stage 5 medium that did not contain a TNKS/Wnt inhibitor, a modified stage 4 medium that contained a TNKS/Wnt inhibitor (0.5 μM AZ6102), or a modified stage 5 medium that contained a TNKS/Wnt inhibitor (0.5 μM AZ6102). Inclusion of the TNKS/Wnt inhibitor (0.5 μM AZ6102) during Stage 4 or Stage 5 decreased the percentage of NKX6.1-/ISL1-SC-DN cells at the end of stage 5.

FIGS. 30A-30B show TNKS inhibition increases the percentage of NKX6.1+/ISL1+SC-β cells and decreases the percentage of NKX6.1-/ISL1-SC-β N cells at the end of Stage 5 when TNK inhibitor is used through several times points through Stage 4 or Stage 4 through Stage 5, including S4d3-S4d6, S4d3-S5d2, S4d5-S4d6, and S4d5-S5d2. FIGS. 31A-31B shows TNK inhibition increases the percentage of NKX6.1+/ISL1+SC-β cells and decreases the percentage of NKX6.1-/ISL1-SC-β N cells at the end of Stage 5 when TNK inhibitor is used during Stage 4 or Stage 5.

Figure 34:
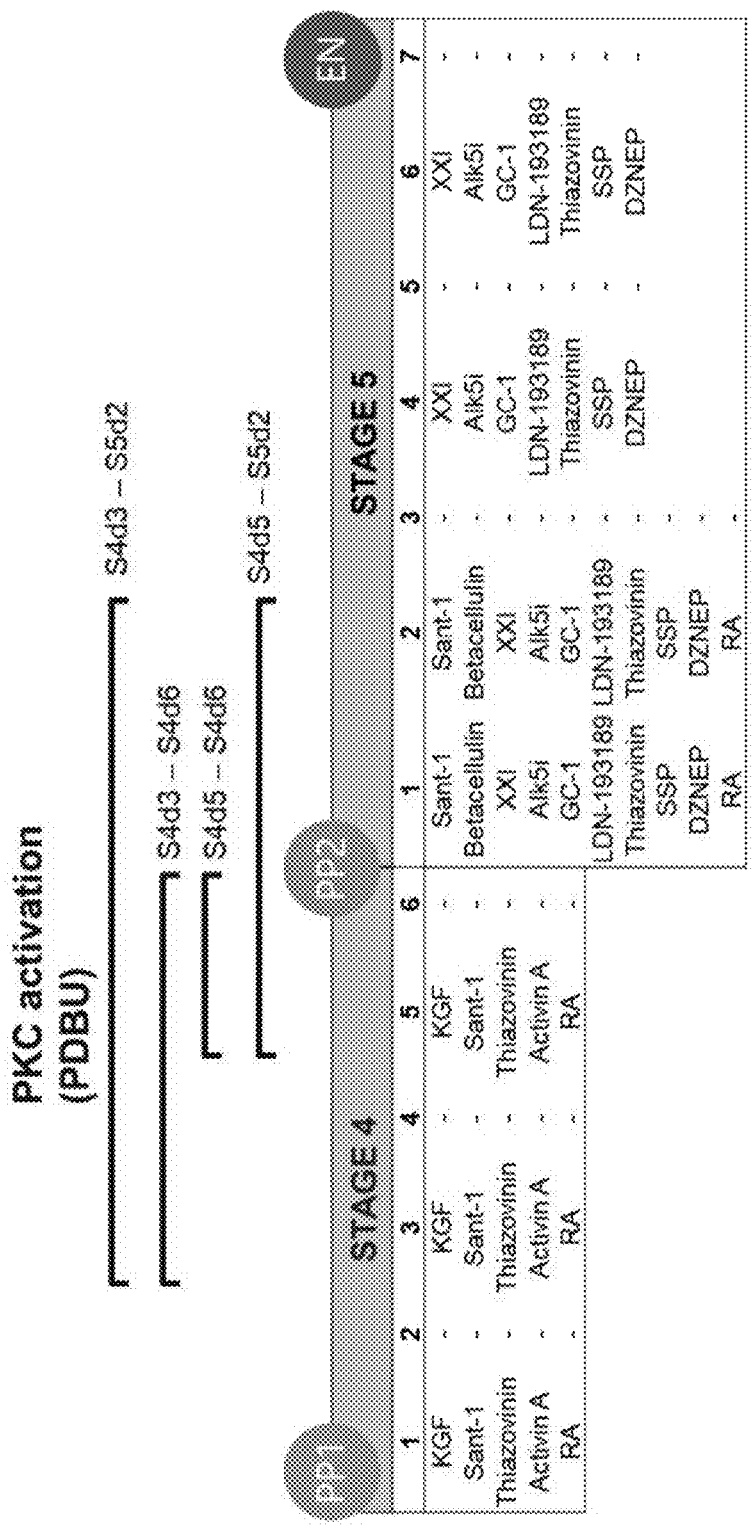
FIG. 34 shows a schematic depicting the exemplary stage 4 and stage 5 protocols utilizing a PKC activator, as described herein. For example, in some embodiments, a PKC activator is utilized during S4d3-S4d6, S4d5-S4d6, S4d5-S5d2, or S4d3-S5d2.

Example 5. Use of Protein Kinase C Activators During Differentiation of Pancreatic Progenitor Cells To further improve the Stage 5 cellular composition (e.g., increased percentage of NKX6.1+/ISL1+β cells and NKX6.1-/ISL1+α cells; decreased percentage of NKX6.1-/ISL1-double negative cells and enterochromaffin (EC) cells), further modifications to the Stage 4 and/or Stage 5 medium were evaluated (FIG. 19). FIG. 34 shows a schematic representation of experiments conducted using protein kinase C (PKC) activators during Stage 4 or during Stage 4 and Stage 5 to evaluate the effect of such activation on the composition of the cell population at the end of Stage 5.

Figure 22:
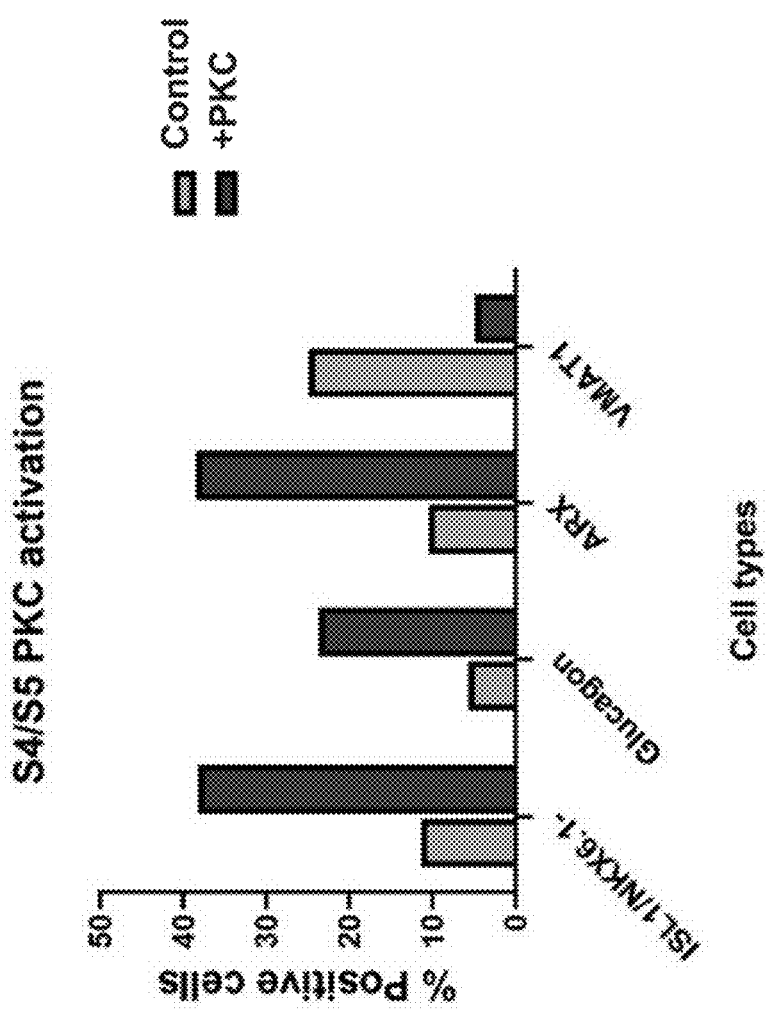
FIG. 22 shows a bar graph depicting the percentage of SC-α cells (glucagon+, ARX+, and NKX6.1-/ISL1+), and the percentage of SC-EC cells (VMAT+), at the end of stage 5 produced using a control stage 4 medium (lacking a PKC activator) (control) or a modified stage 4 medium containing a PKC activator. Inclusion of the PKC activator increased the percentage of SC-α cells (glucagon+, ARX+, and NKX6.1-/ISL1+) and decreased the percentage of SC-EC (VMAT+) cells compared to control.
Figures 23A, 23B:
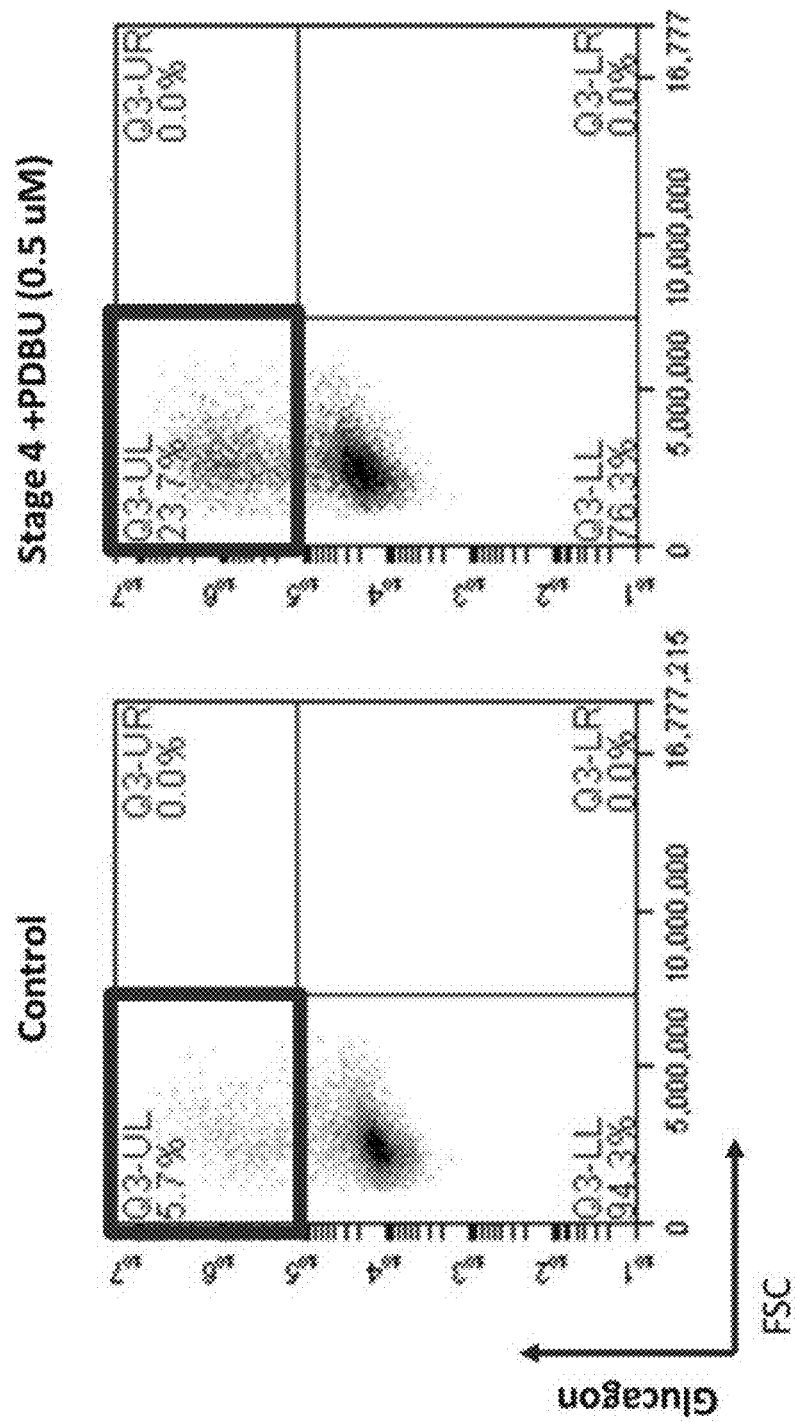
FIG. 23A shows a plot from a FACS analysis of the percentage of glucagon positive SC-α cells at the end of stage 5 produced using a control stage 4 medium that did not contain a PKC activator.
FIG. 23B shows a plot from a FACS analysis of the percentage of glucagon positive SC-α cells at the end of stage 5 produced using a modified stage 4 medium that contained a PKC activator (0.5 μM PDBU (phorbol dibutyrate)). Inclusion of the PKC activator (0.5 μM PDBU (phorbol dibutyrate)) during stage 4 increased the percentage of glucagon positive SC-α cells at the end of stage 5.
Figures 24A, 24B:
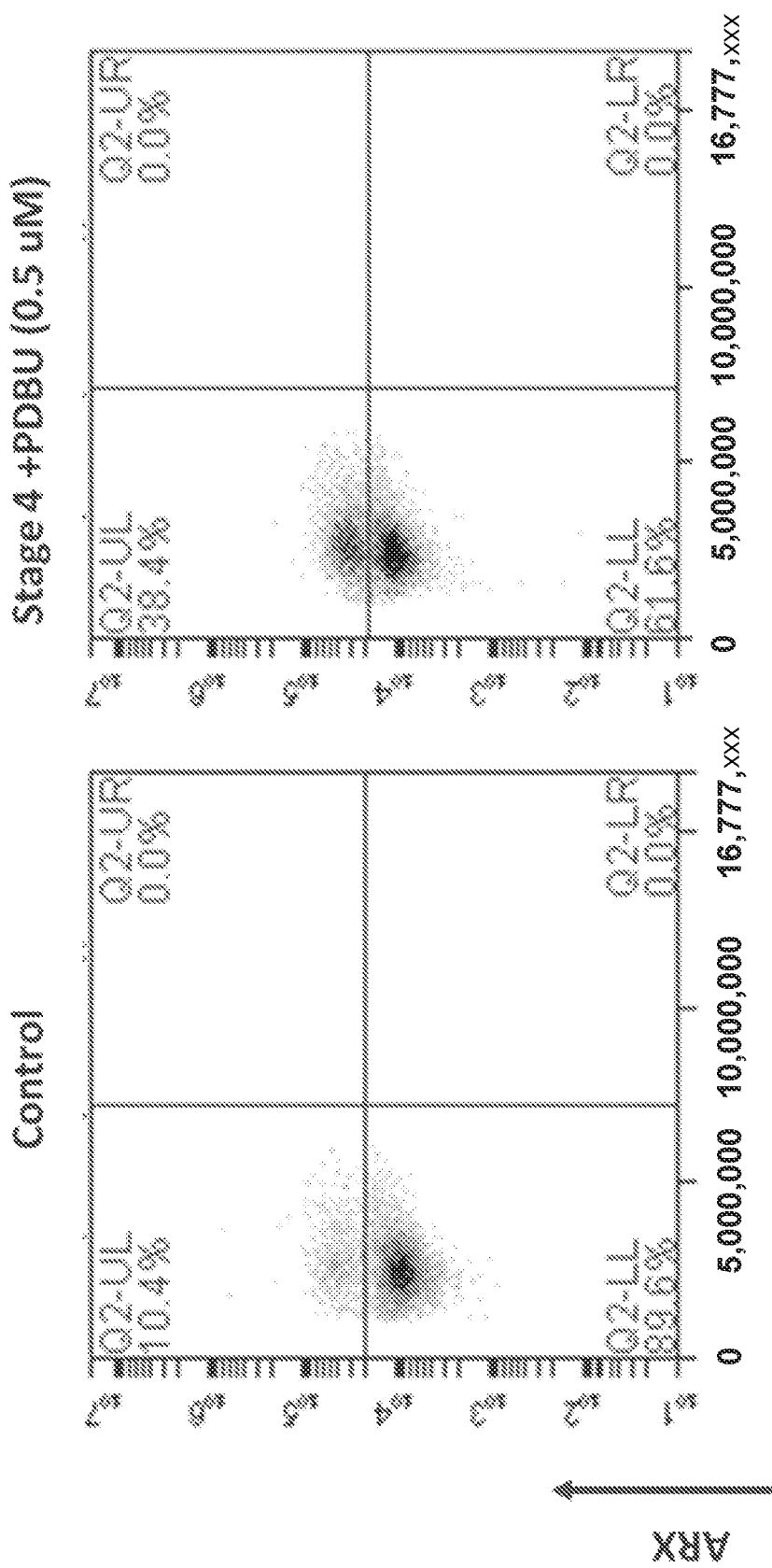
FIG. 24A shows a plot from a FACS analysis of the percentage of ARX positive SC-α cells at the end of stage 5 produced using a control stage 4 medium that did not contain a PKC activator.
FIG. 24B shows a plot from a FACS analysis of the percentage of ARX positive SC-α cells at the end of stage 5 produced using a modified stage 4 medium that contained a PKC activator (0.5 μM PDBU (phorbol dibutyrate)). Inclusion of the PKC activator (0.5 μM PDBU (phorbol dibutyrate)) during stage 4 increased the percentage of ARX positive SC-α cells at the end of stage 5.
Figures 26A, 26B:
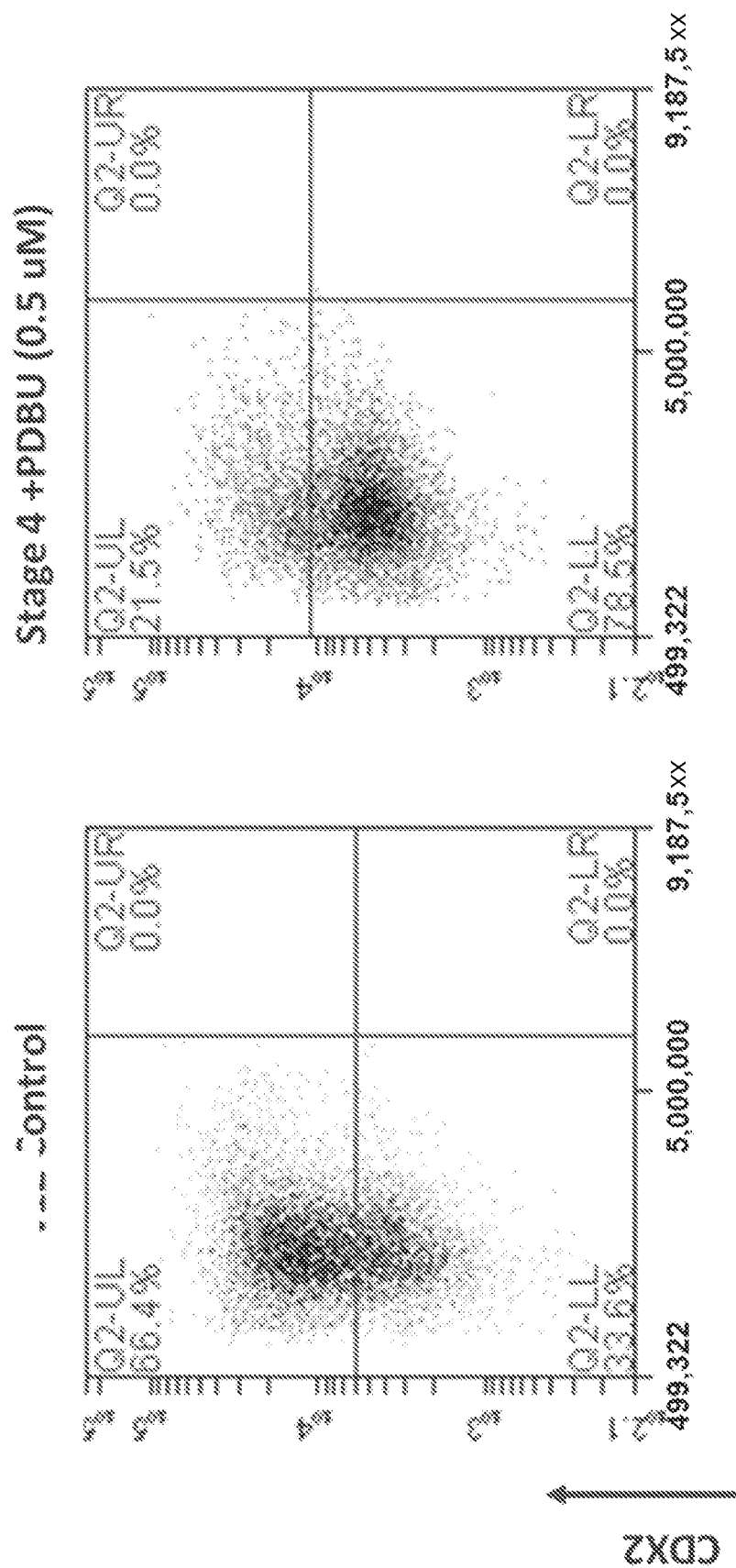
FIG. 26A shows a plot from a FACS analysis of the percentage of CDX2 positive SC-EC cells at the end of stage 5 produced using a control stage 4 medium that did not contain a PKC activator.
FIG. 26B shows a plot from a FACS analysis of the percentage of CDX2 positive SC-EC cells at the end of stage 5 produced using a modified stage 4 medium that contained a PKC activator (0.5 μM PDBU (phorbol dibutyrate)). Inclusion of the PKC activator (0.5 μM PDBU (phorbol dibutyrate)) during stage 4 decreased the percentage of CDCX2 positive SC-EC cells at the end of stage 5.
Figures 26A, 26B:
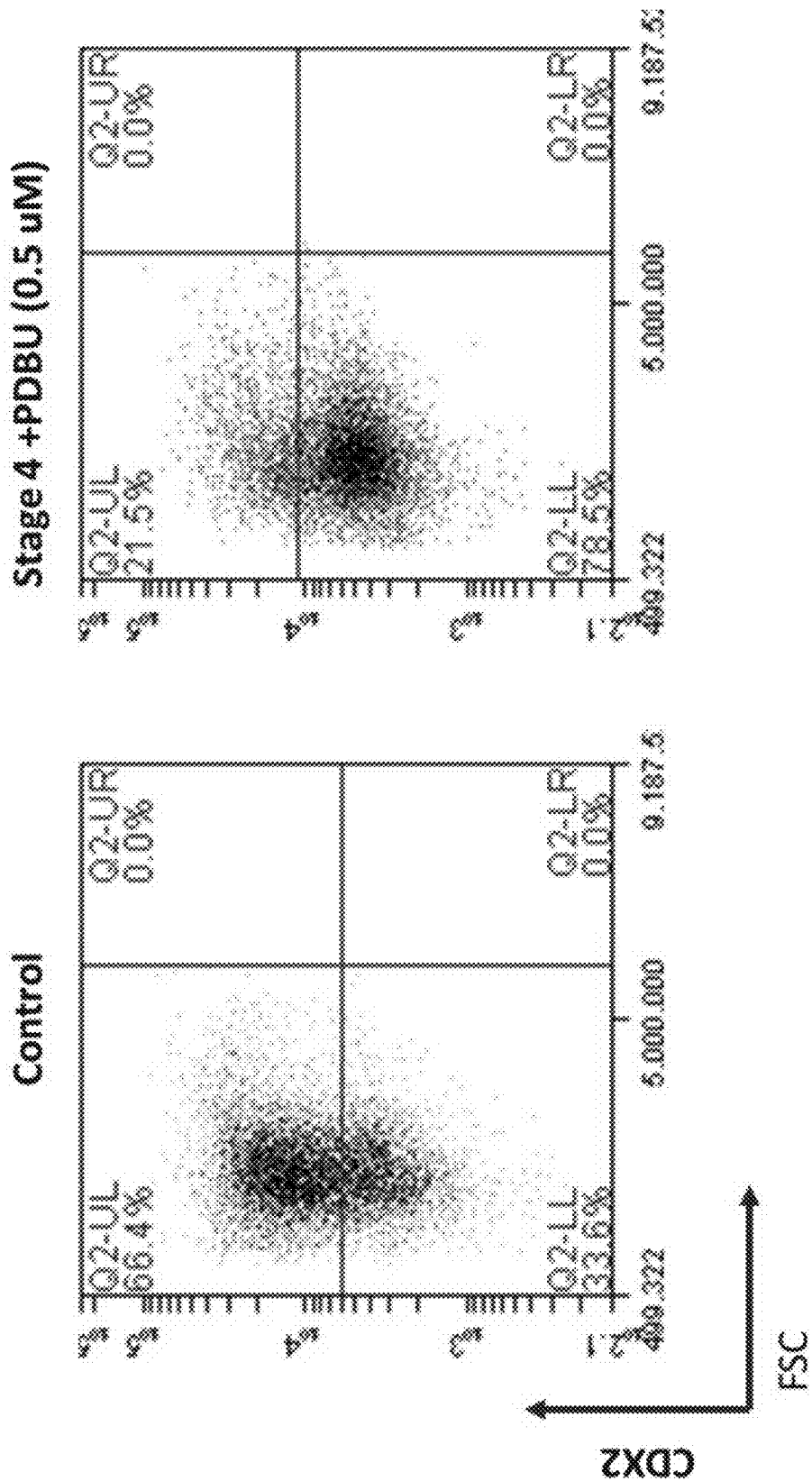
Figure 27:
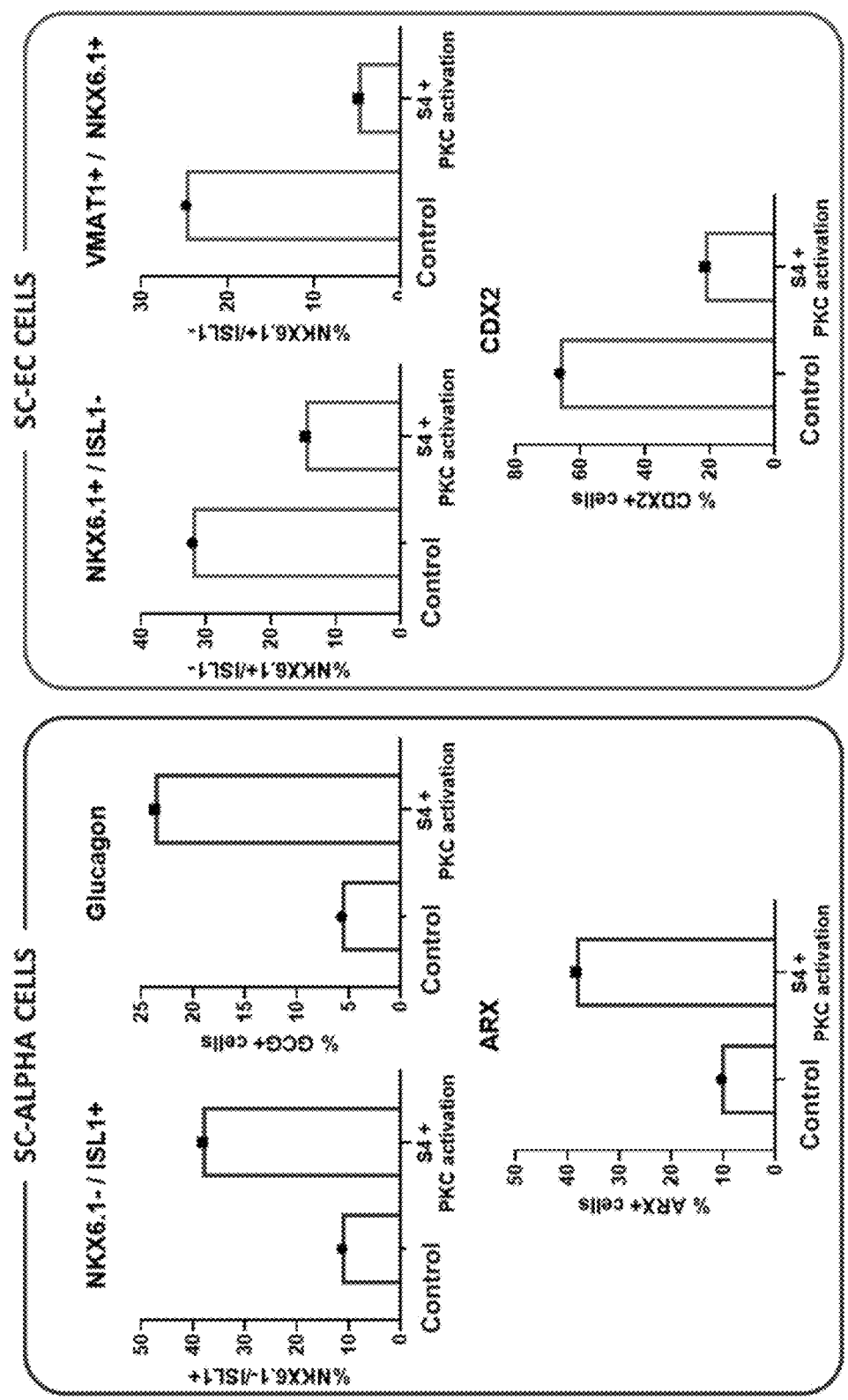
FIG. 27 shows a series of bar graphs depicting the effect of PKC activation during stage 4 of differentiation, wherein the percentage of NKX6.1-/ISL1+SC-α cells, glucagon positive SC-α cells, and ARX positive SC-α cells are increased at the end of Stage 5; and the percentage of NKX6.1+/ISL1-SC-EC cells, VMAT+/NKX6.1+SC-EC cells, and CDX2+SC-EC cells are decreased at the end of Stage 5.

As shown in FIG. 22, PKC activation during Stage 4 increases the percentage of glucagon+, ARX+, and NKX6.1-/ISL1+SC-α cells at the end of Stage 5; and decreases the percentage of VMAT+ enterochromaffin (EC) cells at the end of Stage 5. For example, as shown in FIGS. 23A-23B and FIG. 27, PKC activation (0.5 μM phorbol 12,13-dibutyrate) during Stage 4 increases the percentage of glucagon+SC-α cells at the end of Stage 5 from 5.7% to 23.7%. As shown in FIGS. 24A-24B and FIG. 27, PKC activation (0.5 μM phorbol 12,13-dibutyrate) during Stage 4 increases the percentage of ARX+SC-α cells at the end of Stage 5 from 10.4% to 38.4%. As shown in FIGS. 25A-25B and FIG. 27, PKC activation (0.5 μM phorbol 12,13-dibutyrate) during Stage 4 decreases the percentage of VMAT1+ SC-EC cells at the end of Stage 5 from 24.8% to 4.9%. As shown in FIGS. 26A-26B and FIG. 27, PKC activation (0.5 μM phorbol 12,13-dibutyrate) during Stage 4 decreases the percentage of CDX2+SC-EC cells at the end of Stage 5 from 66.4% to 21.5%.

Figure 35A:
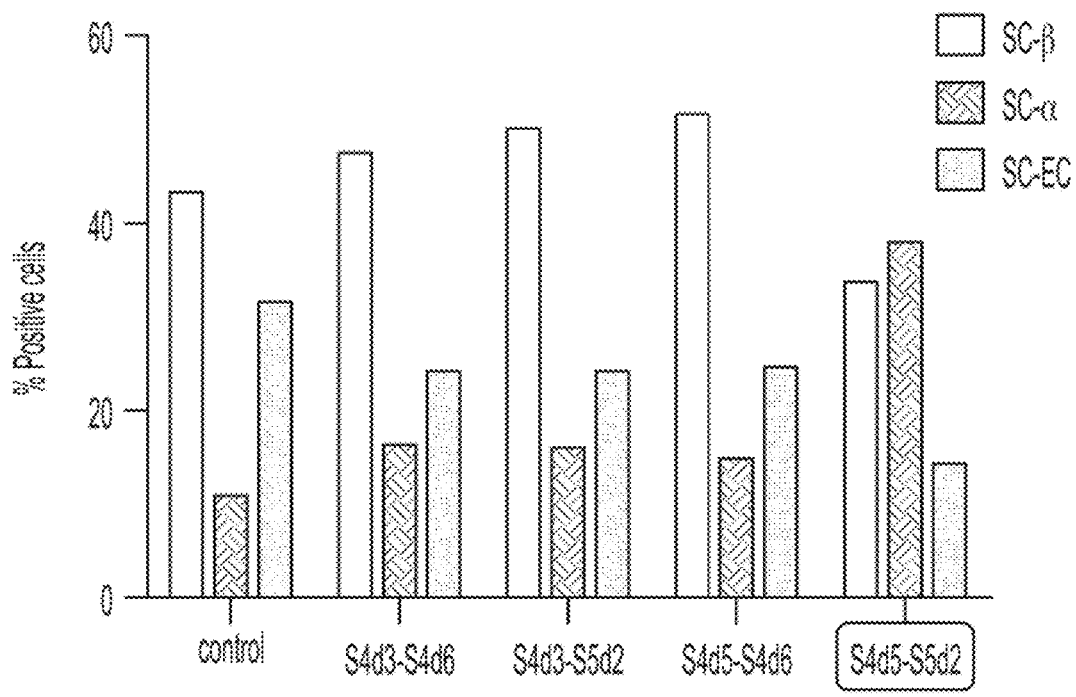
FIG. 35A shows a bar graph depicting the percentage of SC-β cells, SC-α cells, and SC-EC cells using a control stage 4 and stage 5 medium that did not contain a PKC activator or a modified stage 4 and/or 5 medium that contained a PKC activator (0.5 μM PDBU) during S4d3-
Figure 35B:
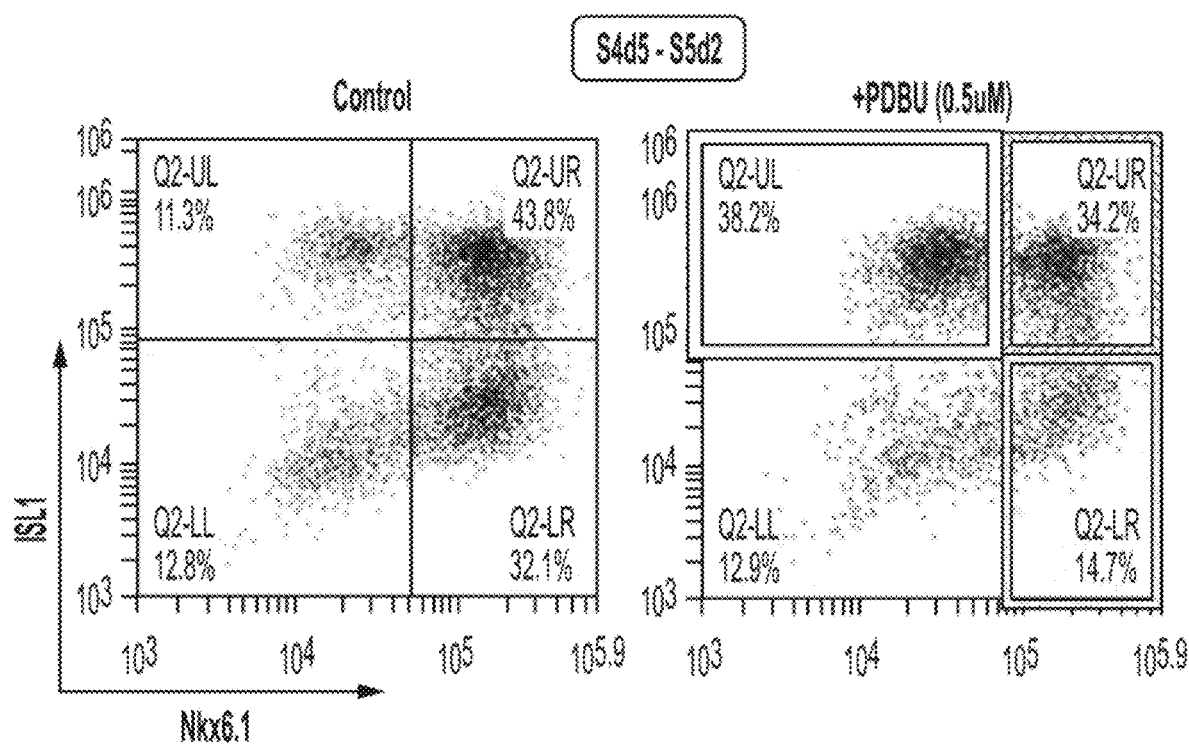
FIG. 35B shows a plot from a FACS analysis of the percentage of SC-β cells, SC-α cells, SC-EC cells, and NKX6.1-/ISL1-double negative cells at the end of stage 5, wherein the stage 4 and stage 5 medium were supplemented with a PKC activator (0.5 µM PDBU) during stage 4 day 5 through stage 5 day 2 (S4d5-S5d2).
Figure 36:
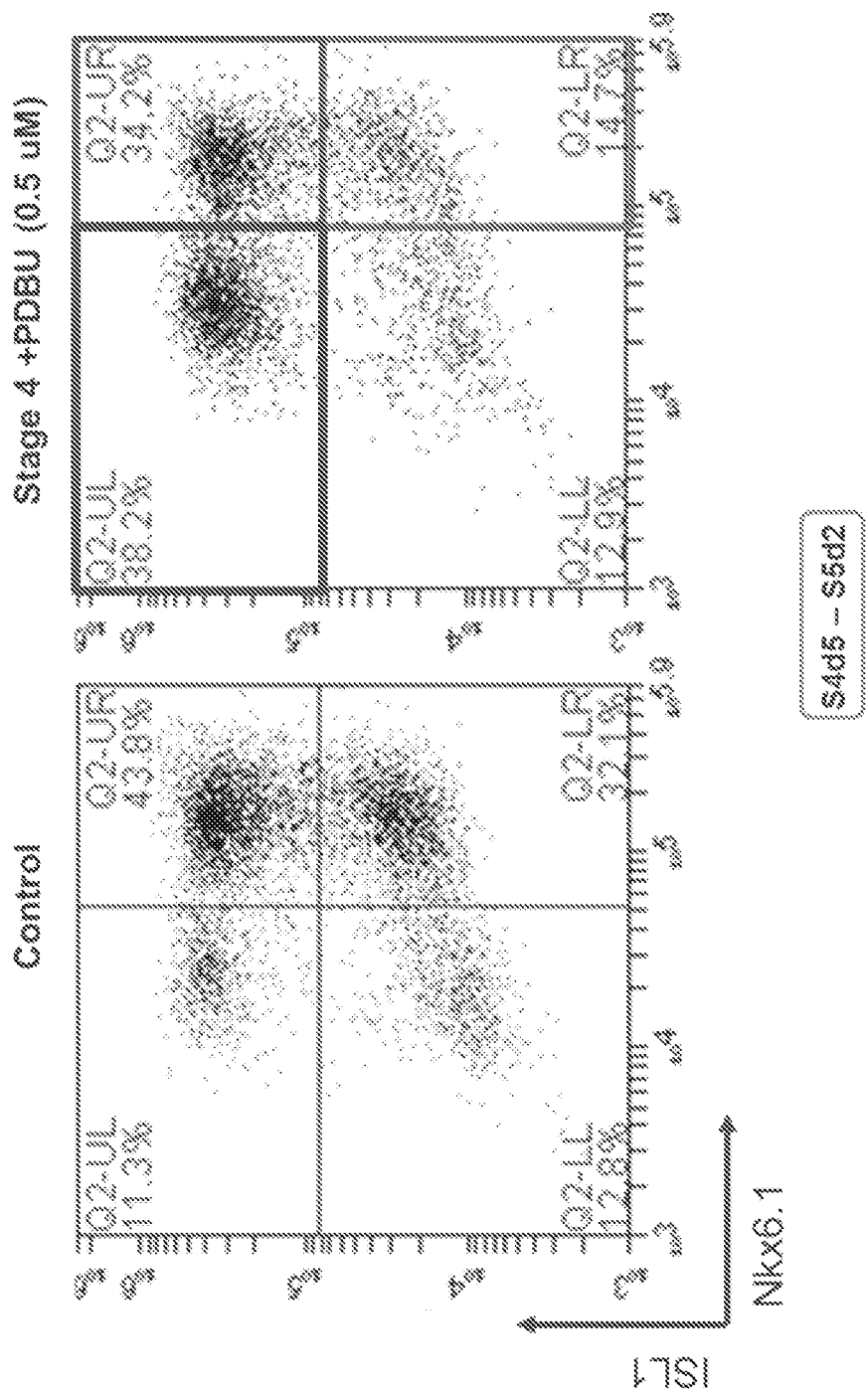
FIG. 36 shows a plot from a FACS analysis of the percentage of SC-β cells, SC-α cells, SC-EC cells, and NKX6.1-/ISL1-double negative cells at the end of stage 5, wherein the stage 4 and stage 5 medium were supplemented with a PKC activator (0.5µM PDBU) during stage 4 day 5 through stage 5 day 2 (S4d5-S5d2).
Figures 37A, 37B:
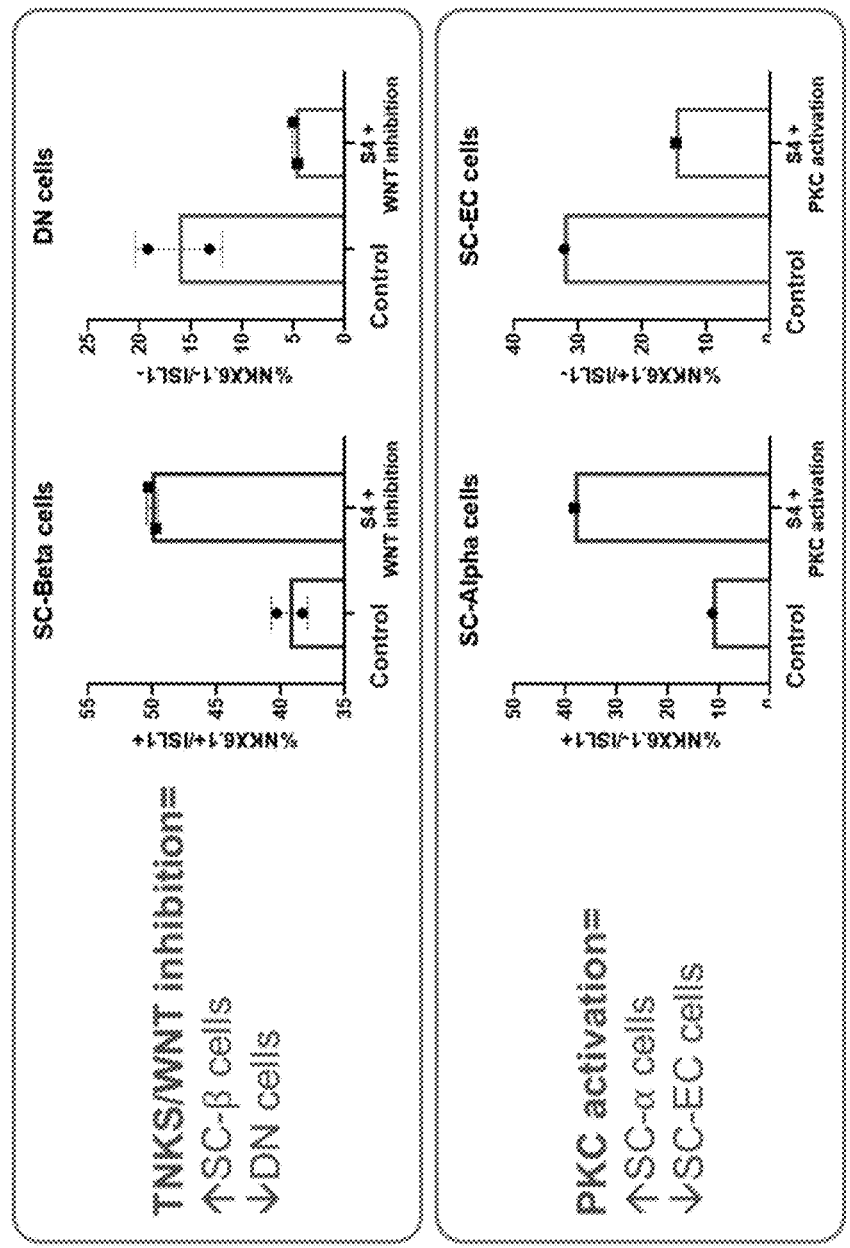
FIG. 37A shows a series of bar graphs depicting the effect of TNKS/WNT inhibition during stage 4 of differentiation, wherein the percentage of SC-β cells at the end of stage 5 is increased; and the percentage of NKX6.1-/ISL1-double negative cells at the end of stage 5 is decreased.
FIG. 37B shows a series of bar graphs depicting the effect of PKC activation during stage 4 of differentiation, wherein the percentage of NKX6.1-/ISL1+SC-α cells at the end of stage 5 is increased; and the percentage of NKX6.1+/ISL1-SC-EC cells at the end of stage 5 is decreased.

FIGS. 35A-35B show PKC activation increases the percentage of NKX6.1-/ISL1+SC-α cells and decreases the percentage of NKX6.1+/ISL1-SC-EC cells at the end of Stage 5 when a PKC activator is used through several times points through Stage 4 or Stage 4 through Stage 5, including S4d3-S4d6, S4d3-S5d2, S4d5-S4d6, and S4d5-S5d2. For example, as shown in FIG. 36 and FIGS. 37A-37B, PKC activation (0.5 µM phorbol 12,13-dibutyrate) during S4d5-S5d2 increases the percentage of NKX6.1-/ISL1+SC-α cells at the end of Stage 5 from 11.3% to 38.2%; and decreases the percentage of NKX6.1+/ISL1-SC-EC cells at the end of Stage 5 from 32.1% to 14.7%.

Figure 32:
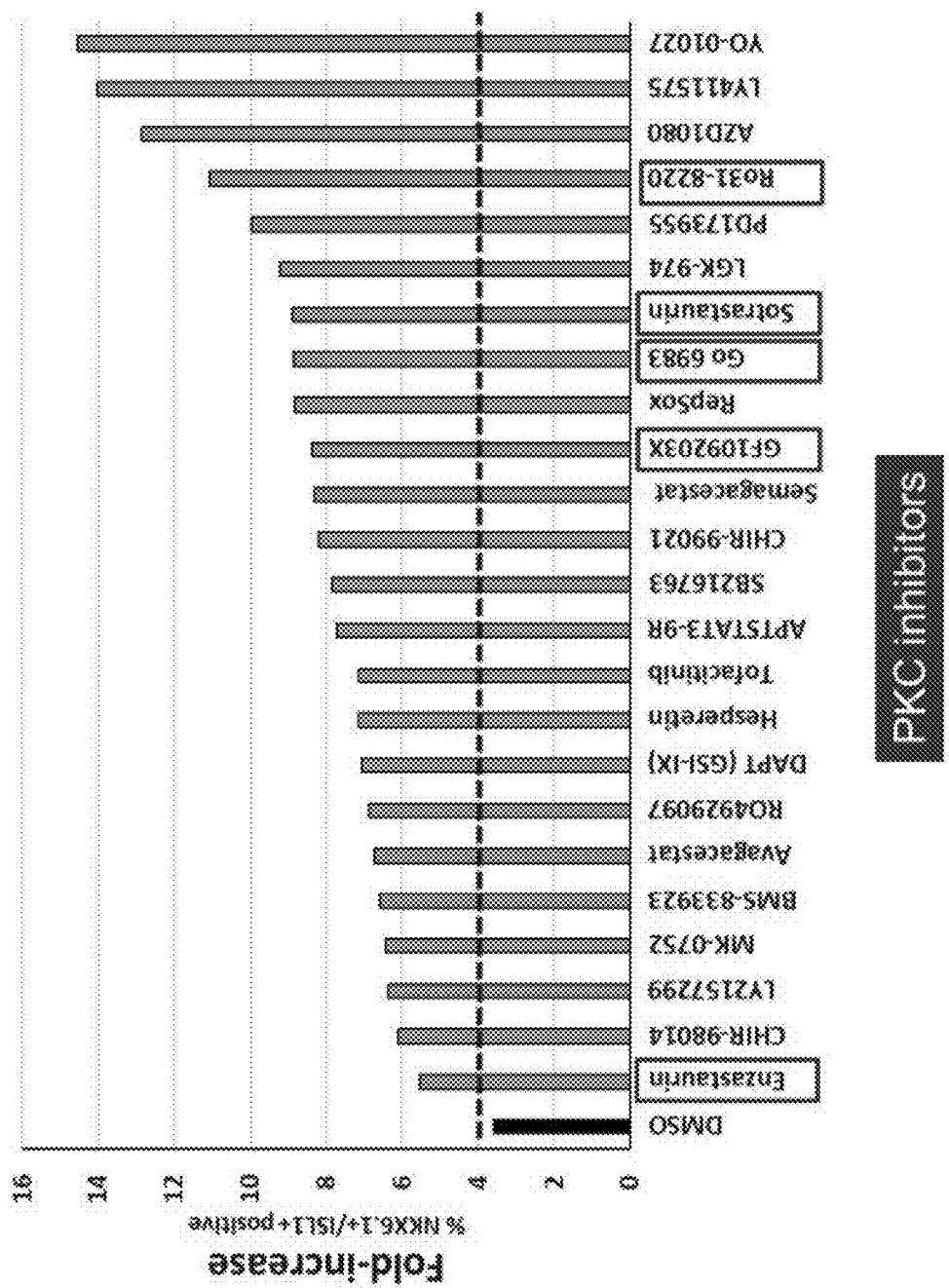
FIG. 32 shows a bar graph depicting results from a screen of PKC activators for the ability to increase the percentage of NKX6.1+/ISL1+SC-R cells at the end of stage 5 when included in stage 4 medium.
Figure 33:
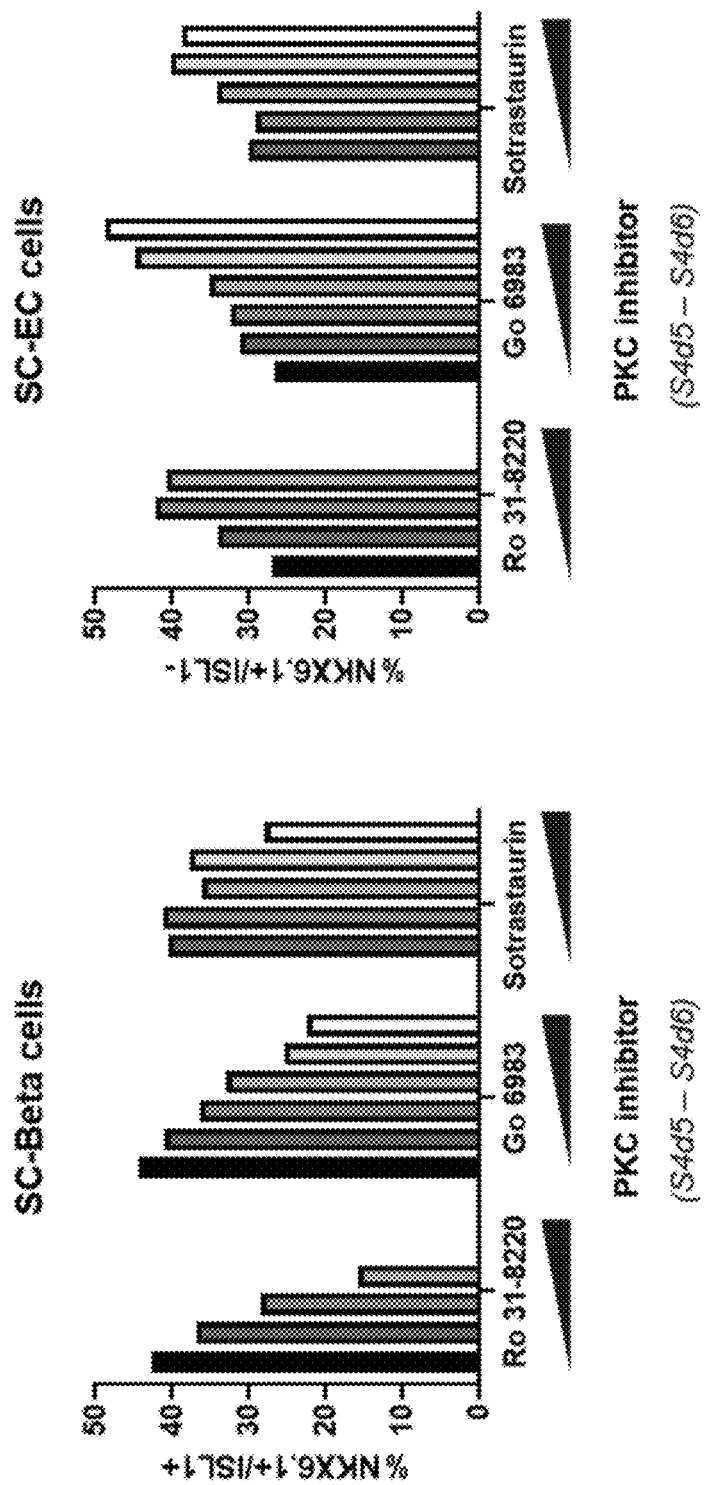
FIG. 33A shows a bar graph depicting the percentage of NKX6.1+/ISL1+SC-F cells at the end of stage 5 produced using a modified stage 4 medium during S4d5-S4d6 that contained a PKC inhibitor: Ro 31-8220, Go 6983, or Sotrastaurin.
FIG. 33B shows a bar graph depicting the percentage of NKX6.1+/ISL1-SC-EC cells at the end of stage 5 produced using a modified stage 4 medium during S4d5-S4d6 that contained a PKC inhibitor: Ro 31-8220, Go 6983, or Sotrastaurin.

Multiple PKC inhibitors were identified in a screen (FIG. 32) and several (Ro 31-8220, Go 6983, and Sotrastaurin) were shown to decrease the percentage of NKX6.1+/ISL1+β cells (FIG. 33A) and decrease the percentage of NKX6.1+/ISL1-SC-EC cells (FIG. 33B) at the end of Stage 5.

Figure 38:
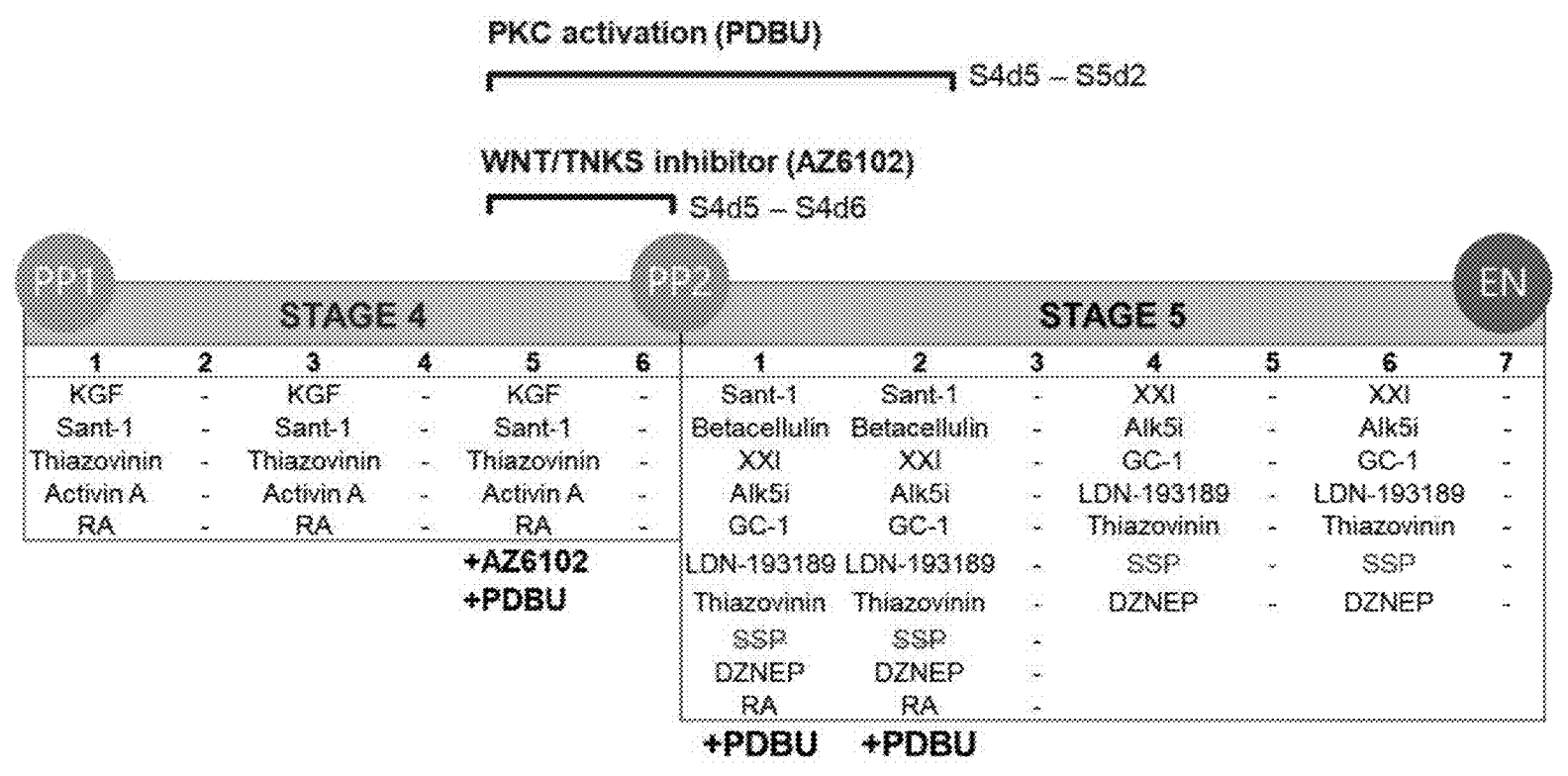

Example 6. Use of Tankyrase Inhibitors and PKC Activator During Differentiation of Pancreatic Progenitor Cells To further improve the Stage 5 cellular composition (e.g., increased percentage of NKX6.1+/ISL1+β cells and NKX6.1-/ISL1+α cells; decreased percentage of NKX6.1-/ISL1-double negative cells and enterochromaffin (EC) cells), further modifications to the Stage 4 and/or Stage 5 medium can be evaluated (FIG. 19). FIG. 38 shows a schematic representation of experiments that are conducted using a TNKS/Wnt inhibitor in combination with a protein kinase C (PKC) activator during Stage 4 or during Stage 4 and Stage 5 to evaluate the effect of such inhibition and activation on the composition of the cell population at the end of Stage 5.

What is claimed is:

1. An in vitro population of cells derived from stem cells in vitro, wherein:
   a) at least 30% of the cells in the population express NKX6.1 and ISL1;
   b) at least 30% of the cells in the population express ISL1 but do not express NKX6.1;
   c) the population comprises cells that express NKX6.1 but do not express ISL1, and less than 20% of the cells in the population express NKX6.1 but do not express ISL1; and
   d) the population comprises at least one cell that is genetically modified.

2. The population of cells of claim 1, wherein less than 15% of the cells in the population express NKX6.1 but do not express ISL1.

3. The population of cells of claim 1, wherein less than 20% of the cells in the population express NXK6.1 and VMAT1.

4. The population of cells of claim 1, wherein less than 10% of the cells in the population express NKX6.1 and VMAT1.

5. The population of cells of claim 1, wherein at least 20% of the cells in the population express ARX.

6. The population of cells of claim 1, wherein at least 30% of the cells in the population express ARX.

7. The population of cells of claim 1, wherein at least 10% of the cells in the population express glucagon.

8. The population of cells of claim 1, wherein at least 15% of the cells in the population express glucagon.

9. The population of cells of claim 1, wherein at least 20% of the cells in the population express glucagon.

10. The population of cells of claim 1, wherein at least 40% of the cells in the population express NKX6.1 and ISL1.

11. The population of cells of claim 1, wherein at least 35% of the cells in the population express ISL1 but do not express NKX6.1.

12. The population of cells of claim 1, wherein the population of cells are in one or more cell clusters.

13. The population of cells of claim 1, wherein the population comprises cells that express NKX6.1 and ISL1 and exhibit glucose stimulated insulin secretion (GSIS) in vitro.

14. The population of claim 1, wherein the at least one cell is genetically engineered to reduce an immune response.

15. The population of cells of claim 14, wherein the at least one cell contains a genetic disruption in beta-2-microglobulin.

16. The population of cells of claim 14, wherein the at least one cell contains a genetic disruption in HLA-A, HLA-B, or HLA-C.

17. The population of cells of claim 1, wherein the population is in a device suitable for implantation into a human subject.

18. The population of cells of claim 1, wherein the levels of NKX6.1 and ISL1 are determined utilizing immunocytochemistry.

19. The population of cells of claim 1, wherein the levels of NKX6.1 and ISL1 are determined utilizing flow cytometry.

20. The population of cells of claim 1, wherein the population is in a composition further comprising one or more of: a transforming growth factor beta (TGF-beta) signaling pathway inhibitor, a bone morphogenesis protein (BMP) inhibitor, a Rho-associated kinase (ROCK) inhibitor, a histone methylation inhibitor, a thyroid hormone signaling pathway activator, or a broad kinase inhibitor.

21. The population of cells of claim 1, wherein the population is in a composition further comprising one or more of: an Activin-like kinase 5 (ALK5) inhibitor, LDN193189, thiazovivin, staurosporine, GC-1, or 3-deazaneplanocin A (DZNEP).

22. A population of cells, wherein:
   a) at least 30% of the cells in the population express NKX6.1 and ISL1;
   b) at least 30% of the cells in the population express ISL1 but do not express NKX6.1; and
   c) the population comprises cells that express NKX6.1 but do not express ISL1, and less than 20% of the cells in the population express NKX6.1 but do not express ISL1,
   wherein the population is in a device, and
   wherein the device comprises:
   (i) a first membrane comprising (A) a first surface comprising a plurality of channels and (B) a second surface opposing the first surface; and
   (ii) a second membrane opposite and attached to the second surface of the first membrane.

23. The population of cells of claim 22, wherein the population comprises cells that express NKX6.1 and ISL1 and exhibited glucose stimulated insulin secretion (GSIS) in vitro.

24. The population of cells of claim 23, wherein the population comprises cells that express NKX6.1 and ISL1 and exhibit glucose stimulated insulin secretion (GSIS) in vitro and that further mature to beta cells if implanted in a patient.

25. The population of cells of claim 22, wherein the first membrane and the second membrane comprise polyvinylidene fluoride or polyvinylidene difluoride (PVDF), polytetrafluoroethylene (PTFE), expanded PTFE (ePTFE), polycaprolactone (PCL), polyethylene/polyethersulfone (PE/PES), polypropylene (PP), polystyrene (PS), poly(m- ethyl methacrylate) (PMMA), poly lactic-co-glycolic acid (PLGA), poly(lactic acid) (PLLA), or any combination thereof.

26. The population of cells of claim 22, wherein the device comprises apertures that allow for vascularization of the device when implanted in a subject.

27. The population of cells of claim 22, wherein less than 10% of the cells in the population express NKX6.1 and VMAT1.

28. The population of cells of claim 22, wherein at least 30% of the cells in the population express ARX.

29. The population of cells of claim 22, wherein at least 20% of the cells in the population express glucagon.

30. The population of cells of claim 22, wherein at least 40% of the cells in the population express NKX6.1 and ISL1.

* * * * *